United States Patent
Cai et al.

(10) Patent No.: US 10,000,501 B2
(45) Date of Patent: Jun. 19, 2018

(54) INHIBITORS OF HIF PROLYL HYDROXYLASE

(71) Applicants: MERCK SHARP & DOHME CORP., Rahway, NJ (US); MSD R&D (CHINA) CO., LTD., Shanghai (CN)

(72) Inventors: Jiaqiang Cai, Shanghai (CN); Vincent Colandrea, North Brunswick, NJ (US); Alejandro Crespo, Edison, NJ (US); John Debenham, Scotch Plains, NJ (US); Xiaoxing Du, Shanghai (CN); Deodialsingh Guiadeen, Chesterfield, NJ (US); Ping Liu, Westfield, NJ (US); Rongqiang Liu, Shanghai (CN); Christina B. Madsen-Duggan, Scotch Plains, NJ (US); Joshua G. McCoy, Washington, DC (US); Weiguo Quan, Shanghai (CN); Christopher Sinz, Middletown, NJ (US); Liping Wang, Cranbury, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 15/513,852

(22) PCT Filed: Sep. 23, 2015

(86) PCT No.: PCT/US2015/051568
§ 371 (c)(1),
(2) Date: Mar. 23, 2017

(87) PCT Pub. No.: WO2016/049097
PCT Pub. Date: Mar. 31, 2016

(65) Prior Publication Data
US 2017/0240555 A1 Aug. 24, 2017

(30) Foreign Application Priority Data
Sep. 28, 2014 (CN) .................. PCT/CN2014/087695

(51) Int. Cl.
| C07D 491/052 | (2006.01) |
| C07D 221/22 | (2006.01) |
| C07D 417/06 | (2006.01) |
| C07D 471/04 | (2006.01) |
| C07D 215/56 | (2006.01) |

(52) U.S. Cl.
CPC ....... *C07D 491/052* (2013.01); *C07D 215/56* (2013.01); *C07D 221/22* (2013.01); *C07D 417/06* (2013.01); *C07D 471/04* (2013.01)

(58) Field of Classification Search
CPC .............. C07D 491/052; C07D 215/56; C07D 221/22; C07D 417/06; C07D 471/04
USPC ...................................................... 546/112
See application file for complete search history.

(56) References Cited

U.S. PATENT DOCUMENTS

| 8,367,666 B2 | 2/2013 | Sasatani et al. |
| 2010/0056563 A1* | 3/2010 | Guiadeen ............. C07D 471/04 514/300 |
| 2011/0009406 A1* | 1/2011 | Clements ............. C07D 471/04 514/234.5 |
| 2014/0024676 A1 | 1/2014 | Witschi et al. |
| 2014/0163061 A1 | 6/2014 | Guenzler-Pukall et al. |
| 2017/0226120 A1* | 8/2017 | Cai .................... C07D 491/048 |

FOREIGN PATENT DOCUMENTS

| WO | WO 2007/038571 | * | 4/2007 |
| WO | WO2007136990 | | 11/2007 |
| WO | WO2009073669 | | 6/2009 |
| WO | WO2009108496 | | 9/2009 |
| WO | WO2009108497 | | 9/2009 |
| WO | WO2012106472 | | 8/2012 |
| WO | WO 2014021281 | * | 2/2014 |
| WO | WO2014102818 | | 7/2014 |
| WO | WO2016049097 | | 3/2016 |
| WO | WO2016049098 | | 3/2016 |
| WO | WO2016049099 | | 3/2016 |
| WO | WO2016049100 | | 3/2016 |

OTHER PUBLICATIONS

Yan; Expert Opinion on Therapeutic Patents, 2010 20, 1219-1245. (Year: 2010).*
Murray et al, Dipeptidyl-Quinolone Derivatives Inhibit Hypoxia Inducible Factor-1alpha Prolyl Hydroxylases-1, -2, and -3 With Altered Selectivity, J. Comb. Chem., 2010, 676-686, 12, American Chemical Society.
Rabinowitz, Inhibition of Hypdxia-Inducible Factor Prolyl Hydroxylase Domain Oxgen Sensors, Journal of Medicinal Chemistry, 2013, 9369-9402, vol. 56.

* cited by examiner

*Primary Examiner* — Daniel R Carcanague
(74) *Attorney, Agent, or Firm* — Matthew A. Leff; Gloria M. Fuentes

(57) ABSTRACT

The present invention concerns a compound of formula I or a pharmaceutically acceptable salt thereof, which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

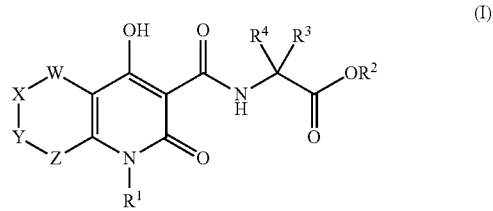

5 Claims, No Drawings

INHIBITORS OF HIF PROLYL HYDROXYLASE

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2), or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I

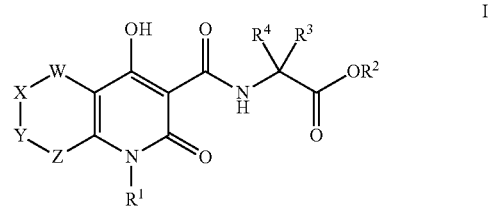

or a pharmaceutically acceptable salt thereof, which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides a compound of formula I or a pharmaceutically acceptable salt thereof:

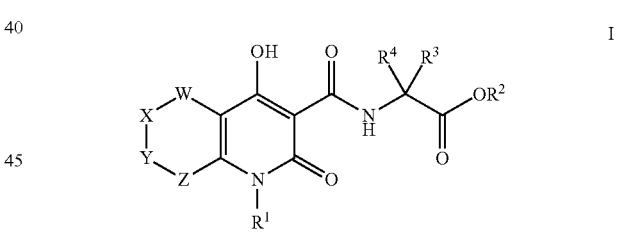

wherein,
W is $CH_2$ or $NR^5$;
X is $CH_2$, O, (C=O), or $NR^5$;
Y is $CH_2$, O, (C=O), or $NR^5$;
Z is $CH_2$ or $NR^5$; wherein when W is $CH_2$ and Z is $CH_2$ then W and Z may combine with another carbon atom to form a bridge;
$R^1$ is selected from hydrogen, $C_{1-4}$ alkyl, $C_{3-8}$ cycloalkyl, aryl, heterocyclyl, Me-aryl, Me-heterocyclyl, Me-cycloalkyl, said cycloalkyl, aryl and heterocyclyl are optionally substituted with 1, 2, or 3 substituents chosen from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN;
$R^2$ is hydrogen or $C_{1-4}$alkyl, wherein said alkyl is optionally substituted with OH;

R[3] and R[4] are each independently chosen from hydrogen or $C_{1-4}$alkyl, wherein said alkyl is optionally substituted with OH and wherein R[3] and R[4] can combine to form cyclopropyl, said cyclopropyl optionally substituted with OH;

R[5] is independently hydrogen, methyl or phenyl; and

R[b] is independently hydrogen or $C_{1-4}$ alkyl.

In another embodiment the present invention provides a compound of formula II or a pharmaceutically acceptable salt thereof:

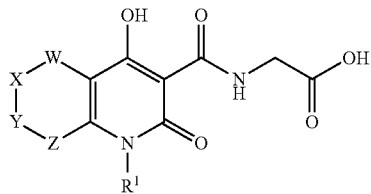

II wherein,

W is $CH_2$ or $NR^5$;

X is $CH_2$, O, (C=O), or $NR^5$;

Y is $CH_2$, O, (C=O), or $NR^5$;

Z is $CH_2$ or $NR^5$; wherein when W is $CH_2$ and Z is $CH_2$ then W and Z may combine with another carbon atom to form a bridge;

R[1] is selected from hydrogen, $C_{1-4}$ alkyl, $C_{3-8}$ cycloalkyl, aryl, heterocyclyl, Me-aryl, Me-heterocyclyl, Me-cycloalkyl, said cycloalkyl, aryl and heterocyclyl are optionally substituted with 1, 2, or 3 substituents chosen from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN;

R[5] is independently hydrogen, methyl or phenyl; and

R[b] is independently hydrogen or $C_{1-4}$ alkyl.

Illustrative but nonlimiting examples of compounds of the invention are the following:

2-(4-Hydroxy-2-oxo-1-(4-(trifluoromethyl)benzyl)-2,5,7,8-tetrahydro-1H-pyrano[4,3-b]pyridine-3-carboxamido)acetic acid;

2-(4-Hydroxy-2-oxo-1-(4-(trifluoromethyl)benzyl)-2,5,6,8-tetrahydro-1H-pyrano[3,4-b]pyridine-3-carboxamido)acetic acid;

2-(4-Hydroxy-7-methyl-2,6-dioxo-1-(4-(trifluoromethyl)benzyl)-1,2,5,6,7,8-hexahydro-1,7-naphthyridine-3-carboxamido)acetic acid;

2-(4-Hydroxy-2-oxo-2,5,7,8-tetrahydro-1H-pyrano[4,3-b]pyridine-3-carboxamido)acetic acid;

2-(1-(4-Cyanobenzyl)-4-hydroxy-2-oxo-2,5,7,8-tetrahydro-1H-pyrano[4,3-b]pyridine-3-carboxamido)acetic acid;

2-(4-hydroxy-1-(4-methoxybenzyl)-2-oxo-2,5,7,8-tetrahydro-1H-pyrano[4,3-b]pyridine-3-carboxamido)acetic acid;

2-(4-hydroxy-2-oxo-1-(4-(trifluoromethoxy)benzyl)-2,5,7,8-tetrahydro-1H-pyrano[4,3-b]pyridine-3-carboxamido)acetic acid;

2-(1-(4-(difluoromethoxy)benzyl)-4-hydroxy-2-oxo-2,5,7,8-tetrahydro-1H-pyrano[4,3-b]pyridine-3-carboxamido)acetic acid;

2-(1-(4-fluorobenzyl)-4-hydroxy-2-oxo-2,5,7,8-tetrahydro-1H-pyrano[4,3-b]pyridine-3-carboxamido)acetic acid;

2-(1-(4-chlorobenzyl)-4-hydroxy-2-oxo-2,5,7,8-tetrahydro-1H-pyrano[4,3-b]pyridine-3-carboxamido)acetic acid;

2-(4-hydroxy-1-(4-(methylsulfonyl)benzyl)-2-oxo-2,5,7,8-tetrahydro-1H-pyrano[4,3-b]pyridine-3-carboxamido)acetic acid;

2-(4-hydroxy-1-(4-isopropylbenzyl)-2-oxo-2,5,7,8-tetrahydro-1H-pyrano[4,3-b]pyridine-3-carboxamido)acetic acid;

2-(4-hydroxy-1-(4-isopropoxybenzyl)-2-oxo-2,5,7,8-tetrahydro-1H-pyrano[4,3-b]pyridine-3-carboxamido)acetic acid;

2-(1-(benzo[d]thiazol-2-ylmethyl)-4-hydroxy-2-oxo-2,5,7,8-tetrahydro-1H-pyrano[4,3-b]pyridine-3-carboxamido)acetic acid;

2-(1-(3,4-difluorobenzyl)-4-hydroxy-2-oxo-2,5,7,8-tetrahydro-1H-pyrano[4,3-b]pyridine-3-carboxamido)acetic acid;

2-(1-(2,4-difluorobenzyl)-4-hydroxy-2-oxo-2,5,7,8-tetrahydro-1H-pyrano[4,3-b]pyridine-3-carboxamido)acetic acid;

2-(1-(4-cyano-2-fluorobenzyl)-4-hydroxy-2-oxo-2,5,7,8-tetrahydro-1H-pyrano[4,3-b]pyridine-3-carboxamido)acetic acid;

2-(1-(4-chloro-2-fluorobenzyl)-4-hydroxy-2-oxo-2,5,7,8-tetrahydro-1H-pyrano[4,3-b]pyridine-3-carboxamido)acetic acid;

2-(1-ethyl-4-hydroxy-2-oxo-2,5,7,8-tetrahydro-1H-pyrano[4,3-b]pyridine-3-carboxamido)acetic acid;

2-(1-(cyclohexylmethyl)-4-hydroxy-2-oxo-2,5,7,8-tetrahydro-1H-pyrano[4,3-b]pyridine-3-carboxamido)acetic acid;

2-(4-hydroxy-1-(naphthalen-2-ylmethyl)-2-oxo-2,5,7,8-tetrahydro-1H-pyrano[4,3-b]pyridine-3-carboxamido)acetic acid;

2-(4-hydroxy-1-methyl-2-oxo-2,5,7,8-tetrahydro-1H-pyrano[4,3-b]pyridine-3-carboxamido)acetic acid;

2-(4-hydroxy-2-oxo-1-((5-(trifluoromethyl)pyrimidin-2-yl)methyl)-2,5,7,8-tetrahydro-1H-pyrano[4,3-b]pyridine-3-carboxamido)acetic acid;

2-(4-Hydroxy-2-oxo-1-(2,4,5-trifluorobenzyl)-2,5,7,8-tetrahydro-1H-pyrano[4,3-b]pyridine-3-carboxamido)acetic acid;

2-(4-Hydroxy-2-oxo-1-((6-(trifluoromethyl)pyridin-3-yl)methyl)-2,5,7,8-tetrahydro-1H-pyrano[4,3-b]pyridine-3-carboxamido)acetic acid;

2-(4-Hydroxy-1-(4-(methylcarbamoyl)benzyl)-2-oxo-2,5,7,8-tetrahydro-1H-pyrano[4,3-b]pyridine-3-carboxamido)acetic acid;

2-(4-Hydroxy-1-((1-methyl-1H-pyrazol-3-yl)methyl)-2-oxo-2,5,7,8-tetrahydro-1H-pyrano[4,3-b]pyridine-3-carboxamido)acetic acid;

2-(1-(4-Cyano-3-methylbenzyl)-4-hydroxy-2-oxo-2,5,7,8-tetrahydro-1H-pyrano[4,3-b]pyridine-3-carboxamido)acetic acid;

2-(1-(4-Cyano-3-fluorobenzyl)-4-hydroxy-2-oxo-2,5,7,8-tetrahydro-1H-pyrano[4,3-b]pyridine-3-carboxamido)acetic acid;

2-(4-Hydroxy-1-((6-methoxypyridin-3-yl)methyl)-2-oxo-2,5,7,8-tetrahydro-1H-pyrano[4,3-b]pyridine-3-carboxamido)acetic acid;

2-(4-Hydroxy-2-oxo-1-(thiazol-5-ylmethyl)-2,5,7,8-tetrahydro-1H-pyrano[4,3-b]pyridine-3-carboxamido)acetic acid;

2-(4-Hydroxy-2-oxo-1-((1-phenyl-1H-pyrazol-3-yl)methyl)-2,5,7,8-tetrahydro-1H-pyrano[4,3-b]pyridine-3-carboxamido)acetic acid;

2-(4-Hydroxy-1-(4-(2-hydroxypropan-2-yl)benzyl)-2-oxo-2,5,7,8-tetrahydro-1H-pyrano[4,3-b]pyridine-3-carboxamido)acetic acid;
2-(1-(4-Carbamoylbenzyl)-4-hydroxy-2-oxo-2,5,7,8-tetrahydro-1H-pyrano[4,3-b]pyridine-3-carboxamido)acetic acid;
2-(4-Hydroxy-2-oxo-1-((2-(trifluoromethyl)thiazol-4-yl)methyl)-2,5,7,8-tetrahydro-1H-pyrano[4,3-b]pyridine-3-carboxamido)acetic acid;
2-(4-Hydroxy-2-oxo-1-(4-(trifluoromethoxy)phenyl)-2,5,7,8-tetrahydro-1H-pyrano[4,3-b]pyridine-3-carboxamido)acetic acid;
2-(1-(4-Chlorobenzyl)-4-hydroxy-2-oxo-2,5,6,8-tetrahydro-1H-pyrano[3,4-b]pyridine-3-carboxamido)acetic acid;
2-(1-(2,4-difluorobenzyl)-4-hydroxy-2-oxo-2,5,6,8-tetrahydro-1H-pyrano[3,4-b]pyridine-3-carboxamido)acetic acid;
2-(4-hydroxy-1-(4-isopropylbenzyl)-2-oxo-2,5,6,8-tetrahydro-1H-pyrano[3,4-b]pyridine-3-carboxamido)acetic acid;
2-(1-(4-cyanobenzyl)-4-hydroxy-2-oxo-2,5,6,8-tetrahydro-1H-pyrano[3,4-b]pyridine-3-carboxamido)acetic acid;
2-(4-hydroxy-1-(4-(methylsulfonyl)benzyl)-2-oxo-2,5,6,8-tetrahydro-1H-pyrano[3,4-b]pyridine-3-carboxamido)acetic acid;
2-(4-hydroxy-2-oxo-1-((6-(trifluoromethyl)pyridin-3-yl)methyl)-2,5,6,8-tetrahydro-1H-pyrano[3,4-b]pyridine-3-carboxamido)acetic acid;
2-(4-hydroxy-2-oxo-1-(2,4,5-trifluorobenzyl)-2,5,6,8-tetrahydro-1H-pyrano[3,4-b]pyridine-3-carboxamido)acetic acid;
2-(1-(4-cyano-2-fluorobenzyl)-4-hydroxy-2-oxo-2,5,6,8-tetrahydro-1H-pyrano[3,4-b]pyridine-3-carboxamido)acetic acid;
2-(1-(4-cyano-3-methylbenzyl)-4-hydroxy-2-oxo-2,5,6,8-tetrahydro-1H-pyrano[3,4-b]pyridine-3-carboxamido)acetic acid;
2-(4-hydroxy-2-oxo-1-((5-(trifluoromethyl)pyrimidin-2-yl)methyl)-2,5,6,8-tetrahydro-1H-pyrano[3,4-b]pyridine-3-carboxamido)acetic acid;
2-(1-(4-chloro-2-fluorobenzyl)-4-hydroxy-2-oxo-2,5,6,8-tetrahydro-1H-pyrano[3,4-b]pyridine-3-carboxamido)acetic acid;
2-(1-(benzo[d]thiazol-2-ylmethyl)-4-hydroxy-2-oxo-2,5,6,8-tetrahydro-1H-pyrano[3,4-b]pyridine-3-carboxamido)acetic acid;
2-(1-(4-(difluoromethoxy)benzyl)-4-hydroxy-2-oxo-2,5,6,8-tetrahydro-1H-pyrano[3,4-b]pyridine-3-carboxamido)acetic acid;
2-(4-hydroxy-1-((1-methyl-1H-pyrazol-3-yl)methyl)-2-oxo-2,5,6,8-tetrahydro-1H-pyrano[3,4-b]pyridine-3-carboxamido)acetic acid;
2-(4-hydroxy-1-(4-methoxybenzyl)-2-oxo-2,5,6,8-tetrahydro-1H-pyrano[3,4-b]pyridine-3-carboxamido)acetic acid;
2-(4-hydroxy-2-oxo-1-(4-(trifluoromethoxy)benzyl)-2,5,6,8-tetrahydro-1H-pyrano[3,4-b]pyridine-3-carboxamido)acetic acid;
2-(1-(4-fluorobenzyl)-4-hydroxy-2-oxo-2,5,6,8-tetrahydro-1H-pyrano[3,4-b]pyridine-3-carboxamido)acetic acid;
2-(1-(3,4-difluorobenzyl)-4-hydroxy-2-oxo-2,5,6,8-tetrahydro-1H-pyrano[3,4-b]pyridine-3-carboxamido)acetic acid;
2-(4-hydroxy-1-(4-(methylcarbamoyl)benzyl)-2-oxo-2,5,6,8-tetrahydro-1H-pyrano[3,4-b]pyridine-3-carboxamido)acetic acid;
2-(4-hydroxy-1-(4-isopropoxybenzyl)-2-oxo-2,5,6,8-tetrahydro-1H-pyrano[3,4-b]pyridine-3-carboxamido)acetic acid;
2-(1-(3-cyanobenzyl)-4-hydroxy-2-oxo-2,5,6,8-tetrahydro-1H-pyrano[3,4-b]pyridine-3-carboxamido)acetic acid;
2-(1-(2-chlorobenzyl)-4-hydroxy-2-oxo-2,5,6,8-tetrahydro-1H-pyrano[3,4-b]pyridine-3-carboxamido)acetic acid;
2-(4-hydroxy-2-oxo-1-(pyridin-2-ylmethyl)-2,5,6,8-tetrahydro-1H-pyrano[3,4-b]pyridine-3-carboxamido)acetic acid;
2-(4-hydroxy-2-oxo-1-(pyridin-4-ylmethyl)-2,5,6,8-tetrahydro-1H-pyrano[3,4-b]pyridine-3-carboxamido)acetic acid;
2-(1-(4-cyano-3-fluorobenzyl)-4-hydroxy-2-oxo-2,5,6,8-tetrahydro-1H-pyrano[3,4-b]pyridine-3-carboxamido)acetic acid;
2-(4-hydroxy-2-oxo-1-(thiazol-5-ylmethyl)-2,5,6,8-tetrahydro-1H-pyrano[3,4-b]pyridine-3-carboxamido)acetic acid;
2-(4-Hydroxy-1-(4-(2-hydroxypropan-2-yl)benzyl)-2-oxo-2,5,6,8-tetrahydro-1H-pyrano[3,4-b]pyridine-3-carboxamido)acetic acid;
2-(1-(4-Carbamoylbenzyl)-4-hydroxy-2-oxo-2,5,6,8-tetrahydro-1H-pyrano[3,4-b]pyridine-3-carboxamido)acetic acid;
2-(4-Hydroxy-2-oxo-1-((4'-(trifluoromethyl)-[1,1'-biphenyl]-4-yl)methyl)-2,5,6,8-tetrahydro-1H-pyrano[3,4-b]pyridine-3-carboxamido)acetic acid;
2-(4-hydroxy-2-oxo-1-((4'-(trifluoromethoxy)-[1,1'-biphenyl]-4-yl)methyl)-2,5,6,8-tetrahydro-1H-pyrano[3,4-b]pyridine-3-carboxamido)acetic acid;
2-(1-((4'-chloro-[1,1'-biphenyl]-4-yl)methyl)-4-hydroxy-2-oxo-2,5,6,8-tetrahydro-1H-pyrano[3,4-b]pyridine-3-carboxamido)acetic acid;
2-(1-((4'-carbamoyl-[1,1'-biphenyl]-4-yl)methyl)-4-hydroxy-2-oxo-2,5,6,8-tetrahydro-1H-pyrano[3,4-b]pyridine-3-carboxamido)acetic acid;
2-(1-((4'-cyano-[1,1'-biphenyl]-4-yl)methyl)-4-hydroxy-2-oxo-2,5,6,8-tetrahydro-1H-pyrano[3,4-b]pyridine-3-carboxamido)acetic acid;
2-(1-(4-Cyano-2-fluorobenzyl)-4-hydroxy-7-methyl-2,6-dioxo-1,2,5,6,7,8-hexahydro-1,7-naphthyridine-3-carboxamido)acetic acid;
2-(4-hydroxy-7-methyl-1-(4-(methylsulfonyl)benzyl)-2,6-dioxo-1,2,5,6,7,8-hexahydro-1,7-naphthyridine-3-carboxamido)acetic acid;
2-(1-(2,4-difluorobenzyl)-4-hydroxy-7-methyl-2,6-dioxo-1,2,5,6,7,8-hexahydro-1,7-naphthyridine-3-carboxamido)acetic acid;
2-(1-(3-cyanobenzyl)-4-hydroxy-7-methyl-2,6-dioxo-1,2,5,6,7,8-hexahydro-1,7-naphthyridine-3-carboxamido)acetic acid;
2-(1-(4-cyanobenzyl)-4-hydroxy-7-methyl-2,6-dioxo-1,2,5,6,7,8-hexahydro-1,7-naphthyridine-3-carboxamido)acetic acid;
2-(1-(4-chlorobenzyl)-4-hydroxy-7-methyl-2,6-dioxo-1,2,5,6,7,8-hexahydro-1,7-naphthyridine-3-carboxamido)acetic acid;
2-(1-(2-chlorobenzyl)-4-hydroxy-7-methyl-2,6-dioxo-1,2,5,6,7,8-hexahydro-1,7-naphthyridine-3-carboxamido)acetic acid;
2-(4-Hydroxy-2-oxo-1-(4-(trifluoromethyl)benzyl)-1,2,5,6,7,8-hexahydroquinoline-3-carboxamido)acetic acid;
2-(4-Hydroxy-2-oxo-1-(4-(trifluoromethyl)benzyl)-1,2,5,6,7,8-hexahydro-1,8-naphthyridine-3-carboxamido)acetic acid;

2-(4-Hydroxy-2-oxo-1-(4-(trifluoromethyl)benzyl)-1,2,5,6,7,8-hexahydro-1,6-naphthyridine-3-carboxamido)acetic acid;

2-(7-Benzyl-4-hydroxy-2-oxo-1-(4-(trifluoromethyl)benzyl)-1,2,5,6,7,8-hexahydro-1,7-naphthyridine-3-carboxamido)acetic acid;

2-(4-Hydroxy-6-methyl-2-oxo-1-(4-(trifluoromethyl)benzyl)-1,2,5,6,7,8-hexahydro-1,6-naphthyridine-3-carboxamido)acetic acid;

2-((5S,8R)-1-(benzo[d]thiazol-2-ylmethyl)-4-hydroxy-2-oxo-1,2,5,6,7,8-hexahydro-5,8-methanoquinoline-3-carboxamido)acetic acid;

2-(−4-hydroxy-2-oxo-1-(4-(trifluoromethyl)benzyl)-1,2,5,6,7,8-hexahydro-5,8-methanoquinoline-3-carboxamido)acetic acid;

2-(−4-hydroxy-2-oxo-1-((2-phenylthiazol-5-yl)methyl)-1,2,5,6,7,8-hexahydro-5,8-methanoquinoline-3-carboxamido)acetic acid; or 2-(−4-hydroxy-2-oxo-1-((4-phenylthiazol-2-yl)methyl)-1,2,5,6,7,8-hexahydro-5,8-methanoquinoline-3-carboxamido)acetic acid;

or a pharmaceutically acceptable salt thereof.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. "$C_{1-4}$ alkyl" includes n-, iso-, sec- and t-butyl, n- and isopropyl, ethyl and methyl.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

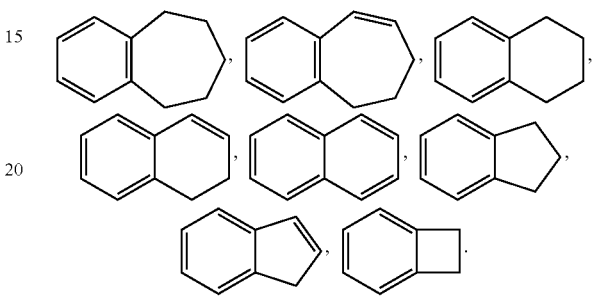

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azepanyl, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isooxazolinyl, oxetanyl, pyranyl, pyrazinyl, pyrazolidinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrahydroisoquinolinyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuryl, 2,3-dihydrobenzo-1,4-dioxinyl (i.e.,

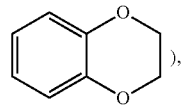), imidazo(2,1-b)(1,3)thiazole, (i.e.,

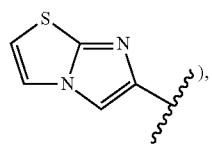 [SMILES: *c1cn2ccsc2n1]), and benzo-1,3-dioxolyl (i.e.,

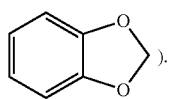).

In certain contexts herein,

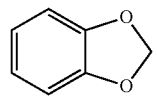

is alternatively referred to as phenyl having as a substituent methylenedioxy attached to two adjacent carbon atoms.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

When any variable (e.g., $R^a$, etc.) occurs more than one time in any substituent or in formulas I-II, its definition in each occurrence is independent of its definition at every other occurrence. Also, combinations of substituents and/or variables are permissible only if such combinations result in stable compounds.

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In another embodiment of the invention is a compound of formulas I and II and pharmaceutically acceptable salts thereof wherein:
W is $CH_2$ or $NR^5$;
X is $CH_2$, O, (C=O), or $NR^5$;
Y is $CH_2$, O, (C=O), or $NR^5$;
Z is $CH_2$ or $NR^5$; wherein when W is $CH_2$ and Z is $CH_2$ then W and Z may combine with another carbon atom to form a bridge;

R¹ is selected from hydrogen, $C_{1-4}$ alkyl, $C_{3-8}$ cycloalkyl, aryl, heterocyclyl, Me-aryl, Me-heterocyclyl, Me-cycloalkyl, said cycloalkyl, aryl and heterocyclyl are optionally substituted with 1, 2, or 3 substituents chosen from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN;

R² is hydrogen or methyl;

R³ and R⁴ are each independently chosen from hydrogen and methyl;

R⁵ is independently hydrogen, methyl or phenyl.

In another embodiment of the invention, W is $CH_2$.
In another embodiment of the invention, W is $NR^5$.
In another embodiment of the invention, X is $CH_2$.
In another embodiment of the invention, X is O.
In another embodiment of the invention, X is (C=O).
In another embodiment of the invention, X is $NR^5$.
In another embodiment of the invention, Y is $CH_2$.
In another embodiment of the invention, Y is O.
In another embodiment of the invention, Y is (C=O).
In another embodiment of the invention, Y is $NR^5$.
In another embodiment of the invention, Z is $CH_2$.
In another embodiment of the invention, W is $CH_2$ and Z is $CH_2$ wherein W and Z are combined with another carbon atom to form a bridge.

In another embodiment of the invention, R¹ is selected from hydrogen, $C_{1-4}$ alkyl, $C_{3-8}$ cycloalkyl, aryl, heterocyclyl, Me-aryl, Me-heterocyclyl, Me-cycloalkyl, said cycloalkyl, aryl and heterocyclyl are optionally substituted with 1, 2, or 3 substituents chosen from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN.

In another embodiment of the invention, R¹ is selected from hydrogen, $C_{1-4}$ alkyl, $C_{3-8}$ cycloalkyl, aryl, heterocyclyl, Me-aryl, Me-heterocyclyl, Me-cycloalkyl, said cycloalkyl, aryl and heterocyclyl are optionally substituted with 1, 2, or 3 substituents chosen from: Cl, F, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, Cl, F, $C(O)N(R^b)_2$, and CN.

In another embodiment of the invention, when R¹ is cycloalkyl, Me-cycloalkyl, aryl, Me-aryl, heterocyclyl and Me-hetercyclyl said cycloalkyl, Me-cycloalkyl, aryl, Me-aryl, heterocyclyl and Me-hetercyclyl is selected from:

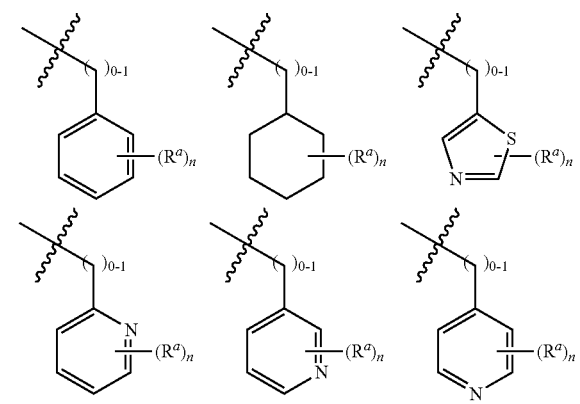

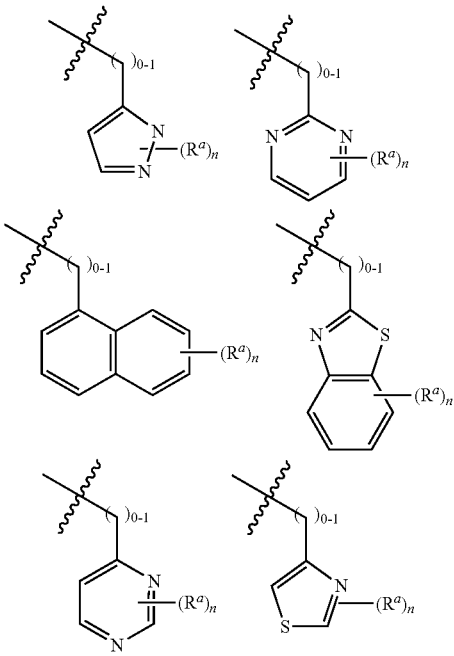

wherein $R^a$ is independently selected from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN; and wherein n is 0, 1, 2 or 3.

Or, wherein $R^a$ is independently selected from: Cl, F, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, Cl, F, $C(O)N(R^b)_2$, and CN; and wherein n is 0, 1, 2 or 3.

In another embodiment of the invention, when R¹ is aryl or heterocyclyl said R¹ is selected from: phenyl, pyrazole, thiazole, pyrimidine, pyridine, pyrazine, biphenyl, oxazole, isooxazole, imidazole, oxadiazole, thiadiazole, triazole, tetrazole, pyridazine, benzothiazole, benzoxaxole, benzoimidazole, optionally substituted with 1-3 substituents independently selected from halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN.

Or, optionally substituted with 1-3 substituents independently selected from Cl, F, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, Cl, F, $C(O)N(R^b)_2$, and CN.

In another embodiment of the invention, W is $CH_2$.
In another embodiment of the invention, X is $CH_2$ or O.
In another embodiment of the invention, Y is $CH_2$ or O.
In another embodiment of the invention, Z is $CH_2$.
In another embodiment of the invention, n is 0, 1, 2 or 3.
In another embodiment of the invention, n is 0, 1 or 2.
In another embodiment of the invention, n is 0 or 1.
In another embodiment of the invention, R² is hydrogen.
In another embodiment of the invention, R³ is hydrogen.

In another embodiment of the invention, $R^4$ is hydrogen.
In another embodiment of the invention, $R^2$ is methyl.
In another embodiment of the invention, $R^3$ is methyl.
In another embodiment of the invention, $R^4$ is methyl.
In another embodiment of the invention, $R^5$ is hydrogen, methyl or phenyl.
In another embodiment of the invention, $R^5$ is hydrogen.
In another embodiment of the invention, $R^5$ is methyl.
In another embodiment of the invention, $R^5$ is phenyl.
In another embodiment of the invention, $R^b$ is independently selected from hydrogen or methyl.

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxy—$CH=C(OH)$— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, dicyclohexylamine, lysine, methyl-glucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methane-sulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

Abbreviations Used in the Description of the Preparation of the Compounds of the Present Invention:

~ Approximately
AcOH Acetic acid
$Ag_2O$ Silver oxide
AIBN 2,2'-azobis(2-methylpropionitrile)
Aq Aqueous
Bn Benzyl
BnBr Benzylbromide
BnCl Benzylchloride
BnOH Benzylalcohol
$Boc_2O$ or di-tert-butyl dicarbonate
$BOC_2O$
Brine Saturated aqueous sodium chloride solution
BuLi n-butyl lithium
CDI Carbonyl diimidazole
DBU 1,8-diazabicyclo[5.4.0]undec-7-ene
DCC N,N'-dicyclohexylcarbodiimide
DEAD diethylazodicarboxylate
DCM Dichloromethane
DIPEA N,N-diisopropylethylaime
DMAP 4-N,N-dimethylaminopyridine
DMF N,N-dimethylformamide
DMSO Dimethyl sulfoxide
DPPA Diphenyl phosphoryl azide
EDC or EDCI 1-(3-dimethylaminopropyl)-3-ethylcarboiimide hydrogenchloride salt
EtOAc or EA Ethyl acetate
Et (et) Ethyl
EtOH Ethanol
$Et_2O$ or ether Diethyl ether
$Et_3N$ Triethylamine
g Gram
h or hr Hour
HATU O-(7-Azabenzotriazol-1-yl)-N,N,N',N'-tetramethyluronium hexafluorophosphate
HCl Hydrochloric acid
HOBt 1-hydroxybenzatriazole
HPLC High-performance liquid chromatography
i-propanol Isopropyl alcohol
i-PrOH or IPA Isopropyl alcohol
$K_2CO_3$ Potassium carbonate
KOH Potassium hydroxide
LAH Lithium aluminium hydride
LiOH Lithium hydroxide
Mg Milligrams
mL Milliliters
mmol Millimole MeCN Acetonitrile
MeOH Methanol
min Minutes
ms or MS Mass spectrum
MTBE Methyl tert-butyl ether
μg Microgram(s)
μL Microliters
NaOEt Sodium ethoxide
NaOMe Sodium methoxide
$Na_2SO_4$ Sodium sulfate
NBS N-bromosuccinimide
NHAc Acetamido
NHCbz Benzyloxycarboxamido
NaOH Sodium hydroxide
$NaN_3$ Sodium azide
$NH_4OH$ ammonium hydroxide
NMP N-methylpyrrolidone
Pd/C Palladium on carbon
$Pd(OH)_2$ Palladium hydroxide
$Pd(PPh_3)_4$ Palladium tetrakis(triphenylphosphine)
PhLi Phenyl lithium
PG Protecting group
Ph Phenyl group
PMB Para-methoxybenzyl
PPTS Pyridinium Para-toluenesulfonate
$PPh_3$ Triphenyphosphine
Rt Retention time
RT or rt Room temperature
$SOCl_2$ Thionyl chloride
TEA Triethylamine
TFA Trifluoroacetic acid
THF Tetrahydrofuran
TBTU O-(Benzotriazol-1-yl)-N,N,N',N'-tetramethyluronium tetrafluoroborate
TMS Trimethylsilyl
TMSBr Trimethylsilyl bromide
TMSCN Trimethylsilyl cyanide
$TMSCHN_2$ (trimethylsilyl)diazomethane
TsCl Para-toluenesulfonyl chloride The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

General Experimental Comments

Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 3.0×50 mm column with gradient 10:90-100 v/v $CH_3CN/H_2O$+v 0.05 TFA over 3.75 min then hold at 100 $CH_3CN$+v 0.05 TFA for 1.75 min; flow rate 1.0 mL/min, UV wavelength 254 nm). Concentration of solutions was carried out on a rotary evaporator under reduced pressure. Flash chromatography was performed using a Biotage Flash Chromatography apparatus (Dyax Corp.) on silica gel (32-63 mM, 60 Å pore size) in pre-packed cartridges. $^1$H-NMR spectra were obtained on a 400 or 500 MHz VARIAN Spectrometer in $CDCl_3$ or $CD_3OD$ or other solvents as indicated and chemical shifts are reported as δ using the solvent peak as reference and coupling constants are reported in hertz (Hz).

Scheme 1 outlines the general synthetic sequence for compounds of Formula I. Ketoester 1 was converted to enamine 2 by ammonium chloride. Upon acylation with malonyl monochloride, compound 3 was obtained which cyclized in the presence of a base to give hydroxypyridone 4. Amide formation with glycine 5 provided 6. $S_{N2}$ type reaction or C—N coupling between compound 6 and $R^1$-LG 7 (LG: leaving group such as I, Br, Cl or OTf) gave compounds of general Formula I. $R^2$ ester of formula I can then be hydrolized to the corresponding carboxylic acid of general Formula Ia ($R^2$=H).

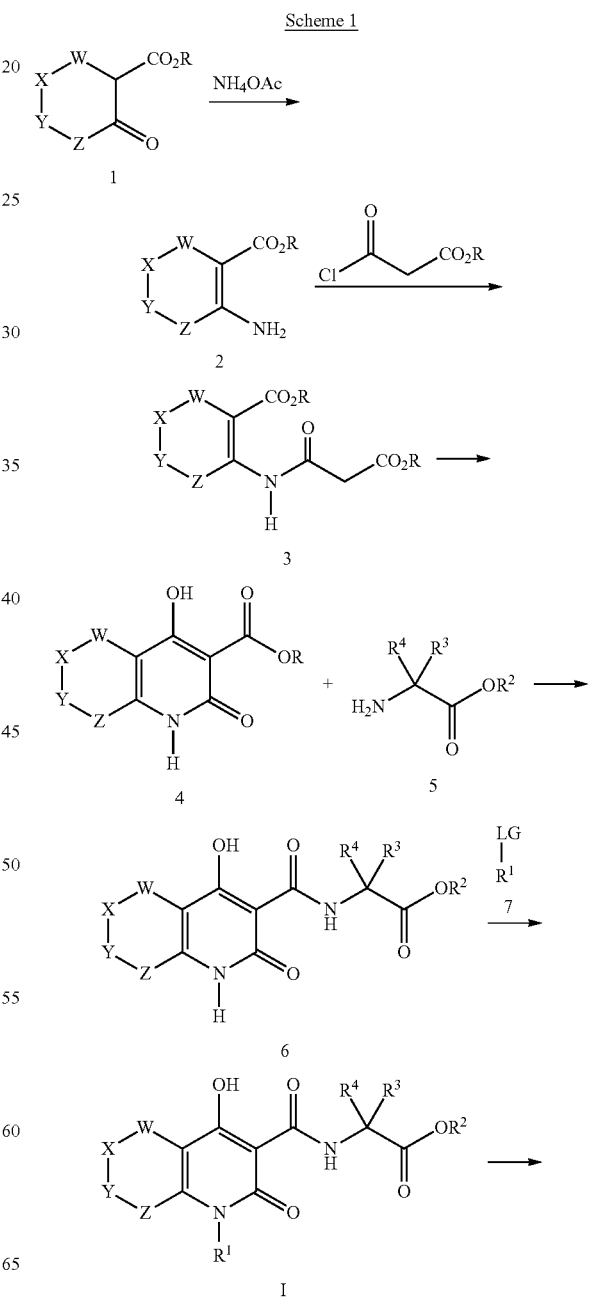

Scheme 1

-continued

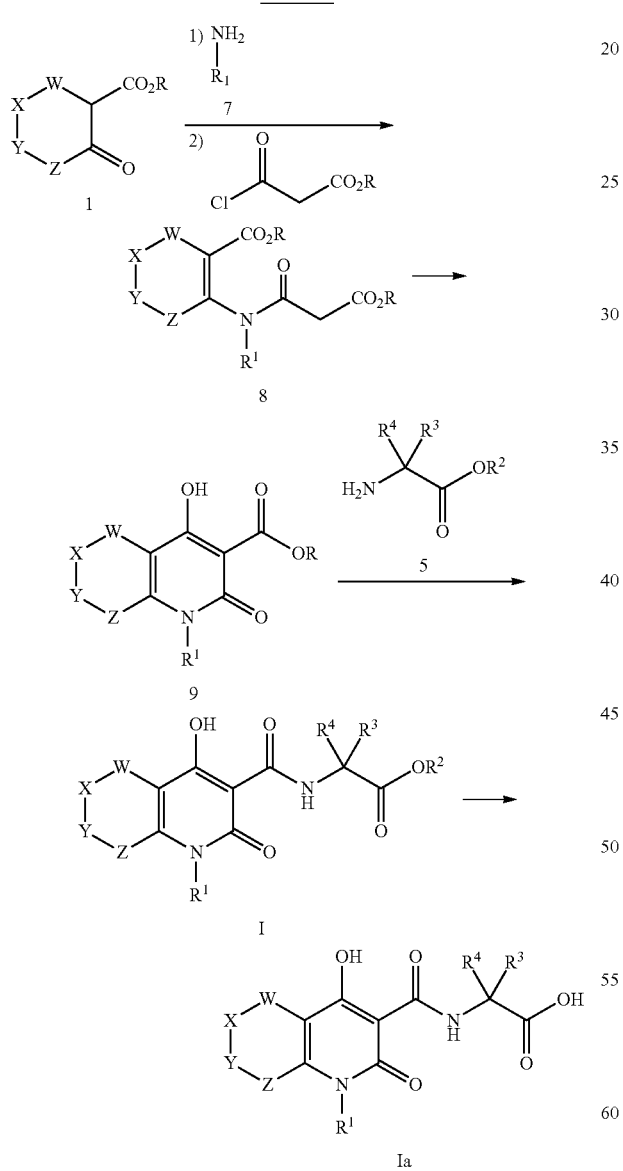

Ia

Alternatively, the compounds of Formula I can be prepared according to Scheme 2 where R¹ group was introduced in the early stage of the synthesis. The remaining transformations are similar to those illustrated in Scheme 1.

Scheme 2

Starting materials useful for the preparation of the compounds in the present invention are known in the art or may be prepared using chemical methodologies known to those skilled in the art.

Intermediate 1 tert-Butyl 2-(4-hydroxy-2-oxo-2,5,7,8-tetrahydro-1H-pyrano[4,3-b]pyridine-3-carboxamido)acetate

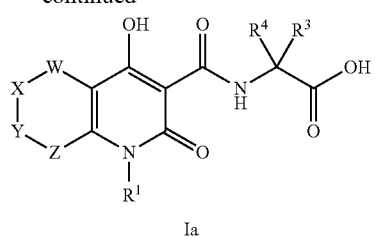

Scheme

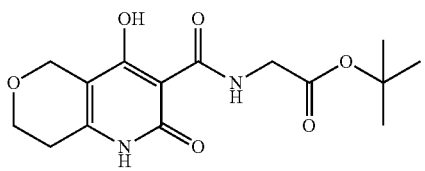 [SMILES: CC(C)(C)OC(=O)CNC(=O)c1c(O)c2c([nH]c1=O)CCOC2]

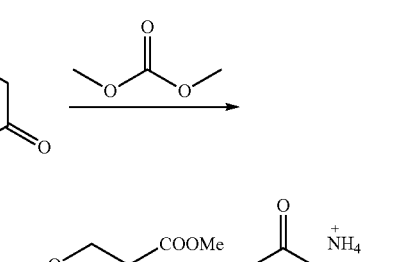

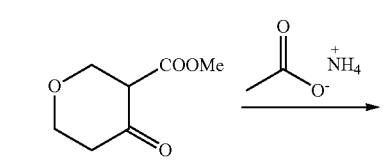

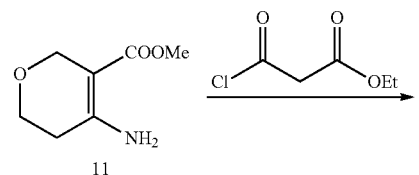

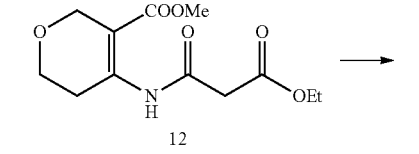

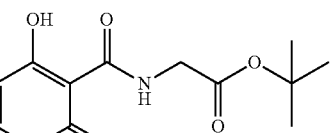

Intermediate 1

Step A: Methyl 4-oxotetrahydro-2H-pyran-3-carboxylate (10)

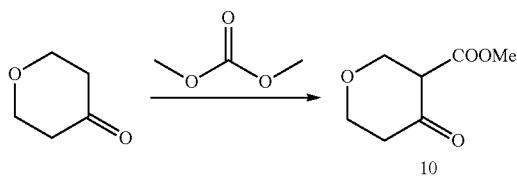

To a solution of dihydro-2H-pyran-4(3H)-one (16.7 g, 167 mmol) and dimethyl carbonate (15.03 g, 167 mmol) in tetrahydrofuran (167 ml) was added potassium tert-butoxide (22.46 g, 200 mmol) portionwise over 30 min at −10° C. After the addition, the reaction mixture was allowed to warm up to room temperature and stirred for 18 hours. Then the reaction mixture was poured into aq. hydrochloric acid (1M, 200 mL) and extracted with MTBE (300 mL). The organic layer was washed with H$_2$O (300 mL) and brine (300 mL), dried over Na$_2$SO$_4$ and concentrated under reduced pressure to afford a yellow oil, which was purified by column chromatography on silica gel (eluted with petroleum ether/EtOAc=3:1) to afford methyl 4-oxotetrahydro-2H-pyran-3-carboxylate (10) as an oil. $^1$H NMR (400 MHz, CDCl$_3$) δ: 11.76 (s, 1H), 4.26 (t, J=1.5 Hz, 2H), 3.84 (t, J=5.7 Hz, 2H), 3.74 (s, 3H), 2.38 (tt, J=5.7, 1.3 Hz, 2H).

Step B: Methyl 4-amino-5,6-dihydro-2H-pyran-3-carboxylate (11)

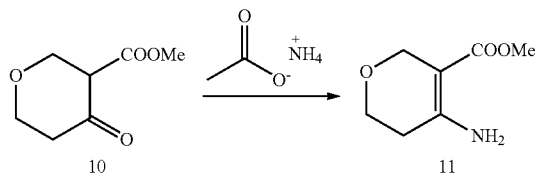

A solution of Step A product (1.3 g, 8.22 mmol) and ammonium acetate (3.17 g, 41.1 mmol) in MeOH (50 ml) was stirred at room temperature for 3 hours. When TLC showed that the reaction was completed, the reaction mixture was concentrated under reduced pressure to remove most of the solvent. The residue was re-dissolved in DCM (150 mL), washed with H$_2$O (100 mL) and brine (100 mL), dried over Na$_2$SO$_4$ and concentrated under reduced pressure to afford methyl 4-amino-5,6-dihydro-2H-pyran-3-carboxylate (11) as a solid. $^1$H NMR (400 MHz, CDCl$_3$) δ: 4.28-4.26 (m, 2H), 3.78 (t, J=5.7 Hz, 2H), 3.66 (s, 3H), 2.28 (t, J=5.7 Hz, 2H).

Step C: Methyl 4-(3-ethoxy-3-oxo-N-(4-(trifluoromethyl)benzyl)propanamido)-2,5-dihydrofuran-3-carboxylate (12)

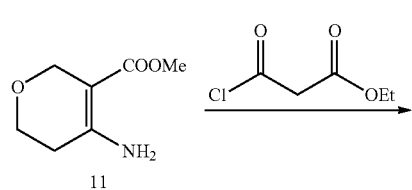

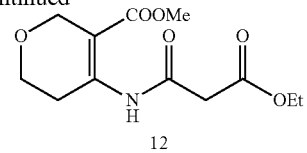

To a solution of Step B product (1.2 g, 7.64 mmol) and DIPEA (4.00 ml, 22.91 mmol) in DCM (20 ml) was added ethyl 3-chloro-3-oxopropanoate (1.724 g, 11.45 mmol) at 0° C., and the reaction mixture was stirred at room temperature for 16 hours. The reaction mixture was diluted with DCM (150 mL), and the organic layer was washed with sat. aq. NaHCO$_3$ (150 mL), H$_2$O (150 mL) and brine (150 mL), dried over Na$_2$SO$_4$ and concentrated under reduced pressure to afford methyl 4-(3-ethoxy-3-oxopropanamido)-5,6-dihydro-2H-pyran-3-carboxylate (12) as an oil, which was used in next step without further purification. LC/MS (m/z): 272 (M+H)$^+$.

Step D: Ethyl 4-hydroxy-2-oxo-2,5,7,8-tetrahydro-1H-pyrano[4,3-b]pyridine-3-carboxylate (13)

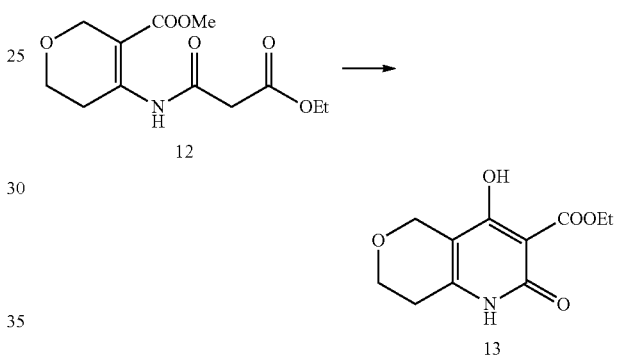

To a solution of Step C product (2.1 g, 3.87 mmol) in toluene (30 ml) was added NaH (0.310 g, 7.74 mmol), followed by EtOH (0.023 ml, 0.387 mmol). Then the reaction mixture was stirred at room temperature for 1 hour. When LCMS showed that the reaction was completed, the reaction mixture was poured to aq. citric acid (1M, 50 mL), extracted with EtOAc (150 mL). The org. phase was washed with water (100 mL) and brine (100 mL), dried over Na$_2$SO$_4$ and concentrated under reduced pressure to afford a brown solid. The solid was triturated with MTBE (20 mL), and the desired ethyl 4-hydroxy-2-oxo-2,5,7,8-tetrahydro-1H-pyrano[4,3-b]pyridine-3-carboxylate (13) was collected by suction as a white solid. $^1$H NMR (DMSO-d$_6$, 400 MHz) δ: 11.41 (br s, 1H), 4.34 (s, 2H), 4.27 (q, J=7.1 Hz, 2H), 3.78 (t, J=5.5 Hz, 2H), 2.53-2.49 (m, 2H), 1.25 (t, J=7.1 Hz, 3H). LC/MS (m/z): 240 (M+H)$^+$.

Step E: tert-Butyl 2-(4-hydroxy-2-oxo-2,5,7,8-tetrahydro-1H-pyrano[4,3-b]pyridine-3-carboxamido)acetate (Intermediate 1)

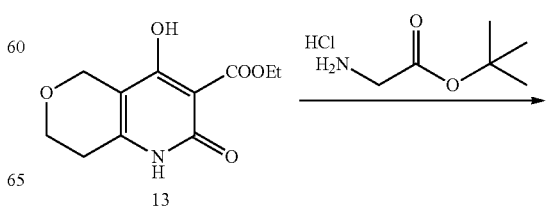

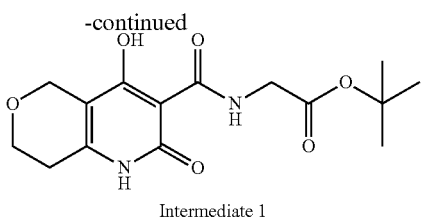

Intermediate 1

To a suspension of Step D product (0.1 g, 0.418 mmol) and DIPEA (0.219 ml, 1.254 mmol) in toluene (2 ml) was added tert-butyl 2-aminoacetate hydrochloride (0.140 g, 0.836 mmol). Then the reaction mixture was heated to 120° C. and stirred for 3 hours. After cooling to room temperature, the reaction mixture was diluted with EtOAc (50 mL), washed with H$_2$O (50 mL×2) and brine (50 mL), dried over Na$_2$SO$_4$ and concentrated under reduced pressure to afford a yellow solid. The crude product was triturated with MTBE (10 mL) and the desired tert-butyl 2-(4-hydroxy-2-oxo-2,5,7,8-tetrahydro-1H-pyrano[4,3-b]pyridine-3-carboxamido) acetate (Intermediate 1) was collected by suction. $^1$H NMR (DMSO-d$_6$, 400 MHz) δ: 11.79 (br s, $^1$H), 10.31 (t, J=5.5 Hz, 1H), 4.36 (s, 2H), 4.00 (d, J=5.6 Hz, 2H), 3.80 (t, J=5.4 Hz, 2H), 2.54 (t, J=5.1 Hz, 2H). LC/MS (m/z): 347 (M+H)$^+$.

Intermediate 2 tert-Butyl 2-(4-hydroxy-2-oxo-2,5,6,8-tetrahydro-1H-pyrano[3,4-b]pyridine-3-carboxamido)acetate

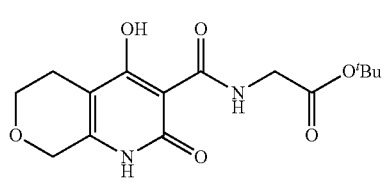 [SMILES: CC(C)(C)OC(=O)CNC(=O)c1c(O)c2c([nH]c1=O)COCC2]

Scheme

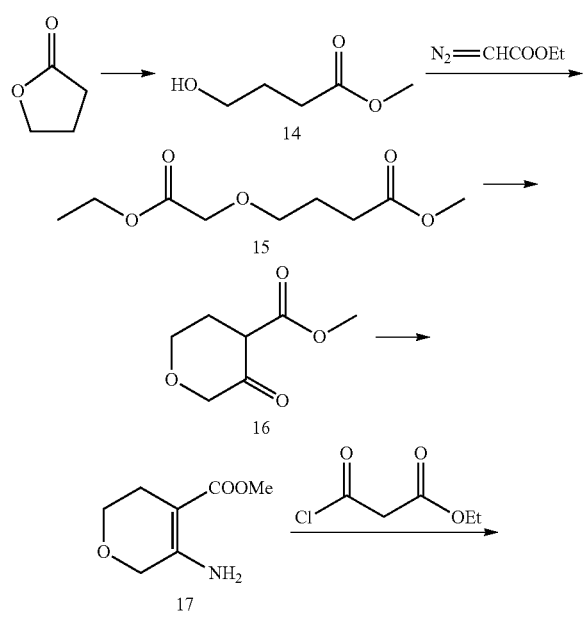

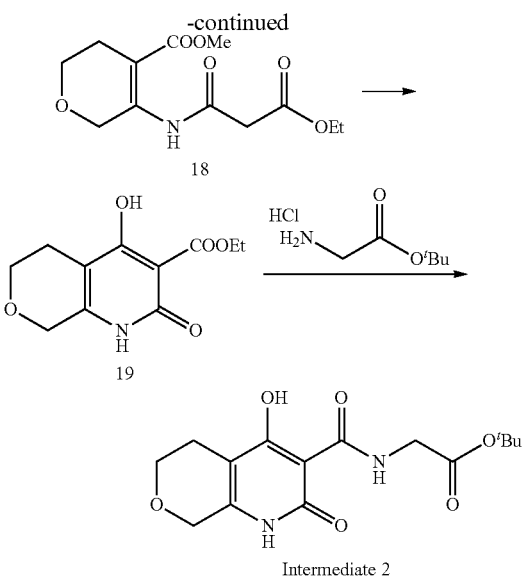

Step A: Methyl 4-hydroxybutanoate (14)

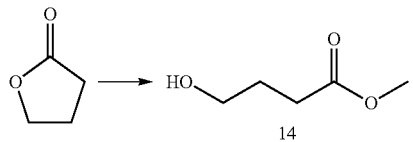

A solution of dihydrofuran-2(3H)-one (20 g, 232 mmol) and TEA (194 ml, 1394 mmol) in MeOH (500 ml) was heated to 60° C. and stirred for 18 hours. After concentration under reduced pressure, the residue was partitioned between EtOAc (300 mL) and brine (200 mL), and the org. phase was dried over Na$_2$SO$_4$ and concentrated to afford methyl 4-hydroxybutanoate (14) as an oil, which was used in next step without further purification. $^1$H NMR (400 MHz, CDCl$_3$) δ: 4.33 (t, J=7.2 Hz, 1H), 3.65-3.60 (m, 5H), 2.40 (t, J=7.2 Hz, 2H), 1.87-1.80 (m, 2H).

Step B: Methyl 4-(2-ethoxy-2-oxoethoxy)butanoate (15)

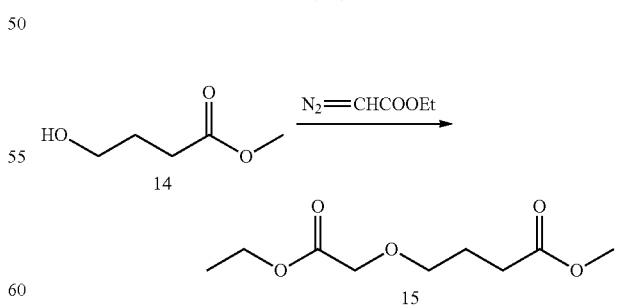

To an ice-salt cooled suspension of methyl 4-hydroxybutanoate (Step A product, 13 g, 110 mmol) and rhodium(II) acetate dimer (0.5 g, 1.131 mmol) in DCM (100 ml) was added ethyl diazoacetate (13.95 g, 110 mmol) dropwise over 20 min to keep the reaction temperature below 0° C. After addition, the reaction mixture was allowed to warm up to room temperature and the mixture stirred for 2 hours. When TLC showed the reaction was completed, the reaction mixture was concentrated under reduced pressure, and the green residue was purified by column chromatography on silica gel (eluted with petroleum ether/EtOAc=4:1) to afford methyl 4-(2-ethoxy-2-oxoethoxy)butanoate (15) as an oil. $^1$H NMR (400 MHz, CDCl$_3$) δ: 4.21-4.14 (q, J=7.2 Hz, 2H), 4.03 (s, 2H), 3.65 (s, 3H), 3.55 (t, J=6.2 Hz, 2H), 2.43 (t, J=7.4 Hz, 2H), 1.96-1.86 (m, 2H), 1.25 (t, J=7.2 Hz, 3H).

Step C: Methyl 5-hydroxy-3,6-dihydro-2H-pyran-4-carboxylate (16)

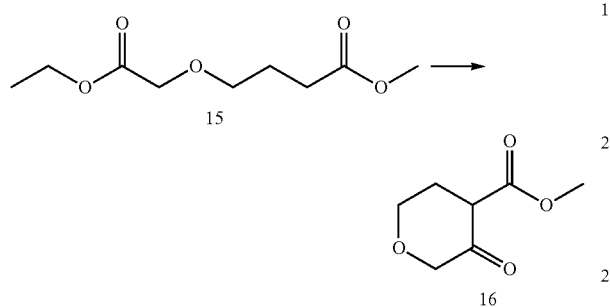

To a solution of methyl 4-(2-ethoxy-2-oxoethoxy)butanoate (Step B product, 18 g, 88 mmol) in toluene (300 ml) was added a solution of tBuOK in THF (106 mL, 106 mmol, 1M in THF) dropwise over 30 min. Then the reaction mixture was stirred at room temperature for 18 hours. When TLC showed that the reaction was completed, the reaction mixture was poured into 1M HCl (300 mL). The organic layer was separated, and the aqueous layer was extracted with EtOAc (200 mL×2). The combined organic layers were washed with brine (300 mL), dried over Na$_2$SO$_4$ and concentrated under reduced pressure to afford a brown oil, which was purified by column chromatography on silica gel (eluted with petroleum ether/EtOAc=19:1) to afford methyl 5-hydroxy-3,6-dihydro-2H-pyran-4-carboxylate (16) as an oil (about 1:1 mixture of methyl 3-oxotetrahydro-2H-pyran-4-carboxylate and ethyl 5-hydroxy-3,6-dihydro-2H-pyran-4-carboxylate by $^1$HNMR). $^1$H NMR (400 MHz, CDCl$_3$) δ: 11.75 (s, 1H), 4.12 (s, 2H), 3.79-3.76 (m, 5H), 2.34-2.37 (m, 2H). LC/MS (m/z): 376 (M+H)$^+$.

Step D: Methyl 5-amino-3,6-dihydro-2H-pyran-4-carboxylate (17)

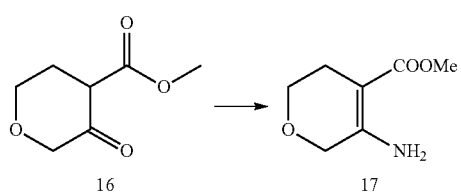

To a solution of methyl 5-hydroxy-3,6-dihydro-2H-pyran-4-carboxylate (Step C product, 6.0 g, 37.9 mmol) in methanol (150 ml) was added ammonium acetate (2.92 g, 37.9 mmol). The reaction mixture was then stirred at room temperature for 5 hours. When TLC showed that the reaction was completed, the reaction mixture was concentrated under reduced pressure to remove most of the solvent. The colorless residue was re-dissolved in DCM (150 mL), washed with H$_2$O (100 mL) and brine (100 mL), dried over Na$_2$SO$_4$ and concentrated under reduced pressure to afford methyl 5-amino-3,6-dihydro-2H-pyran-4-carboxylate (17) as a solid ($^1$H NMR showed that about 1:1 mixture of methyl 5-amino-3,6-dihydro-2H-pyran-4-carboxylate and ethyl 5-amino-3,6-dihydro-2H-pyran-4-carboxylate). $^1$H NMR (CDCl$_3$, 400 MHz) δ: 4.10 (s, 2H), 3.78 (t, J=5.7 Hz, 2H), 3.69 (s, 3H), 2.33 (t, J=5.7 Hz, 2H).

Step E: Methyl 5-(3-ethoxy-3-oxopropanamido)-3,6-dihydro-2H-pyran-4-carboxylate (18)

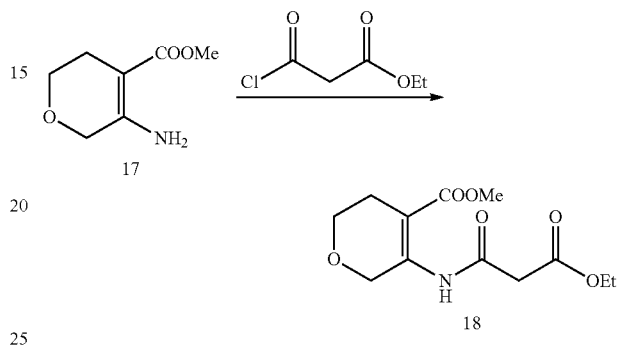

To a solution of methyl 5-amino-3,6-dihydro-2H-pyran-4-carboxylate (Step D product, 5.2 g, 33.1 mmol) in MeCN (100 ml) was added ethyl 3-chloro-3-oxopropanoate (7.47 g, 49.6 mmol). Then the reaction mixture was heated to 70° C. and stirred for 1 hour. When LCMS showed that the reaction was completed, the reaction mixture was concentrated under reduced pressure to remove most of the solvent. The brown residue was re-dissolved in EtOAc (200 mL), washed with sat. aq. NaHCO$_3$ (200 mL), H$_2$O (200 mL) and brine (200 mL), dried over Na$_2$SO$_4$ and concentrated under reduced pressure to afford methyl 5-(3-ethoxy-3-oxopropanamido)-3,6-dihydro-2H-pyran-4-carboxylate (18) as an oil (as a mixture of methyl 5-(3-ethoxy-3-oxopropanamido)-3,6-dihydro-2H-pyran-4-carboxylate and ethyl 5-(3-ethoxy-3-oxopropanamido)-3,6-dihydro-2H-pyran-4-carboxylate). LC/MS (m/z): 272 (M+H)$^+$.

Step F: Ethyl 4-hydroxy-2-oxo-2,5,6,8-tetrahydro-1H-pyrano[3,4-b]pyridine-3-carboxylate (19)

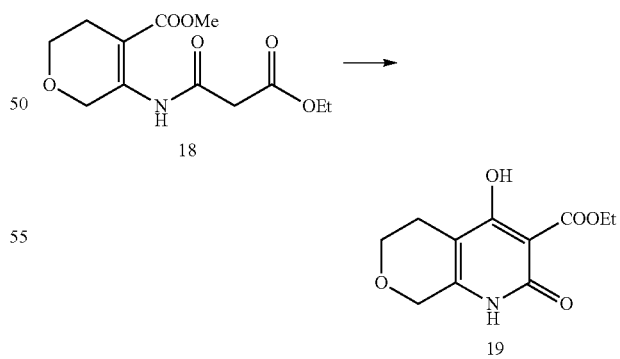

To a solution of methyl 5-(3-ethoxy-3-oxopropanamido)-3,6-dihydro-2H-pyran-4-carboxylate (Step E product, 7.5 g, 22.1 mmol) in toluene (200 ml) was added NaH (1.77 g, 44.2 mmol), followed by EtOH (0.2 ml, 2.21 mmol). Then the reaction mixture was stirred at room temperature for 1 hour. When LCMS showed the reaction was completed, the reaction mixture was poured to sat. aq. citric acid (250 mL), extracted with EtOAc (300 mL), washed with H₂O (250 mL) and brine (250 mL), dried over Na₂SO₄ and concentrated under reduced pressure to afford a brown solid, which was triturated with MTBE (50 mL). The desired ethyl 4-hydroxy-2-oxo-2,5,6,8-tetrahydro-1H-pyrano[3,4-b]pyridine-3-carboxylate (19) was collected by suction as a powder. ¹H NMR (DMSO-d₆, 400 MHz) δ: 13.41 (br s, 1H), 11.30 (br s, 1H), 4.31 (s, 2H), 4.27 (q, J=7.1 Hz, 2H), 3.79 (t, J=5.5 Hz, 2H), 2.35 (t, J=5.5 Hz, 2H), 1.24 (t, J=7.1 Hz, 3H). LC/MS (m/z): 240 (M+H)⁺.

Step G: tert-Butyl 2-(4-hydroxy-2-oxo-2,5,6,8-tetrahydro-1H-pyrano[3,4-b]pyridine-3-carboxamido) acetate (Intermediate 2)

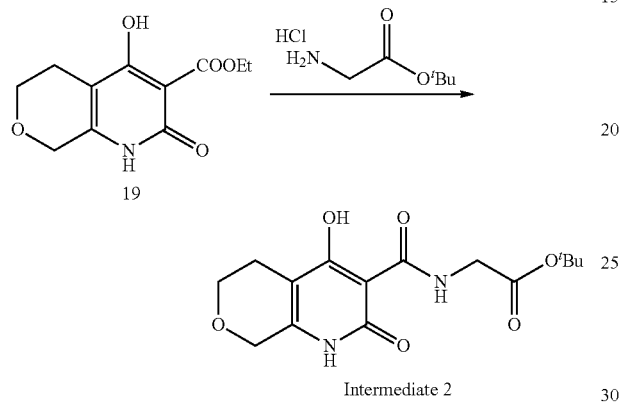

Intermediate 2

To a suspension of ethyl 4-hydroxy-2-oxo-2,5,6,8-tetrahydro-1H-pyrano[3,4-b]pyridine-3-carboxylate (Step F product, 2.0 g, 8.36 mmol) and DIPEA (4.38 ml, 25.08 mmol) in toluene (60 ml) was added tert-butyl 2-aminoacetate hydrochloride (2.80 g, 16.72 mmol). Then the reaction mixture was heated to 120° C. and stirred for 5 hours. After cooling to room temperature, the reaction mixture was diluted with EtOAc (150 mL), washed with H₂O (100 mL) and brine (100 mL), dried over Na₂SO₄ and concentrated under reduced pressure to afford a yellow solid. The crude yellow solid was triturated with MTBE (20 mL), and the desired tert-Butyl 2-(4-hydroxy-2-oxo-2,5,6,8-tetrahydro-1H-pyrano[3,4-b]pyridine-3-carboxamido) acetate (Intermediate 2) was collected by suction as a powder. ¹H NMR (DMSO-d₆, 400 MHz) δ: 11.68 (br s, 1H), 10.33 (t, J=5.6 Hz, 1H), 4.37 (s, 2H), 4.00 (d, J=5.6 Hz, 2H), 3.81 (t, J=5.4 Hz, 2H), 2.37 (t, J=5.4 Hz, 2H). LC/MS (m/z): 347 (M+Na)⁺.

Intermediate 3 tert-Butyl 2-(1-(4-bromobenzyl)-4-hydroxy-2-oxo-2,5,6,8-tetrahydro-1H-pyrano[3,4-b]pyridine-3-carboxamido)acetate

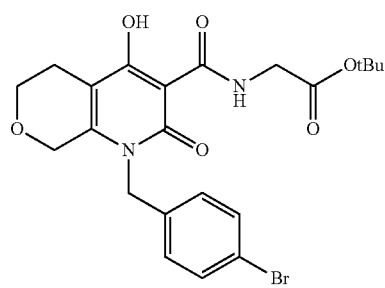 [SMILES: CC(C)(C)OC(=O)CNC(=O)c1c(O)c2c(n(Cc3ccc(Br)cc3)c1=O)COCC2]

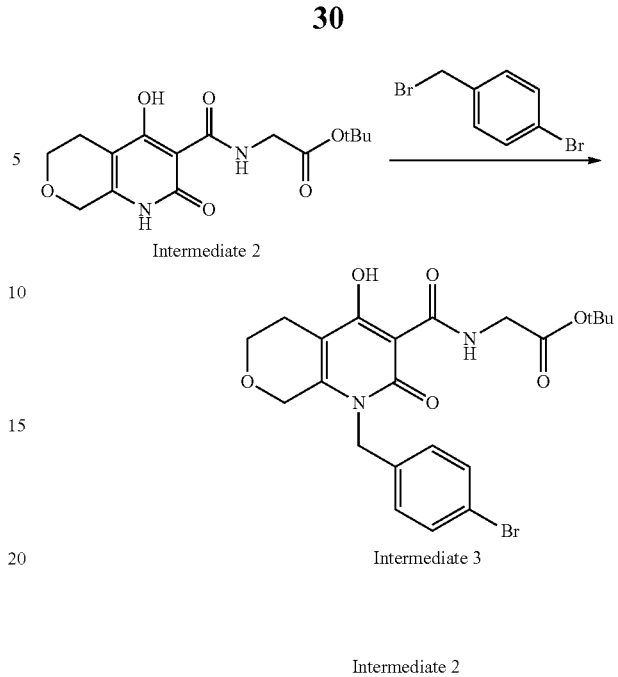

Intermediate 3

To a solution of tert-butyl 2-(4-hydroxy-2-oxo-2,5,6,8-tetrahydro-1H-pyrano[3,4-b]pyridine-3-carboxamido)acetate (Intermediate 2, 100 mg, 0.308 mmol) and 1-bromo-4-(bromomethyl)benzene (92 mg, 0.370 mmol) in acetone (4 mL) and DMF (2 mL) was added K₂CO₃ (63.9 mg, 0.462 mmol). After addition, the mixture was stirred at 50° C. for 3 hours. TLC (petroleum ether:EtOAc=5:1) showed the reaction was completed. The reaction mixture was poured into water (30 mL) and extracted with EtOAc (10 mL×3). The combined organic layers were dried over Na₂SO₄, filtered and concentrated under reduced pressure. The residue was purified by prep-TLC (petroleum ether:EtOAc=5:1) to give Intermediate 3 as a solid. ¹H NMR (CDCl₃, 400 MHz): δ 15.97 (s, 1H), 10.55 (s, 1H), 7.46 (d, J=8.4 Hz, 2H), 7.01 (d, J=8.0 Hz, 2H), 5.10 (d, J=8.8 Hz, 2H), 4.47 (s, 2H), 4.09 (d, J=5.2 Hz, 2H), 3.86 (t, J=5.6 Hz, 2H), 2.62 (t, J=5.4 Hz, 2H), 1.49 (s, 9H).

Intermediate 4 tert-Butyl 2-(4-hydroxy-7-methyl-2,6-dioxo-1,2,5,6,7,8-hexahydro-1,7-naphthyridine-3-carboxamido) acetate

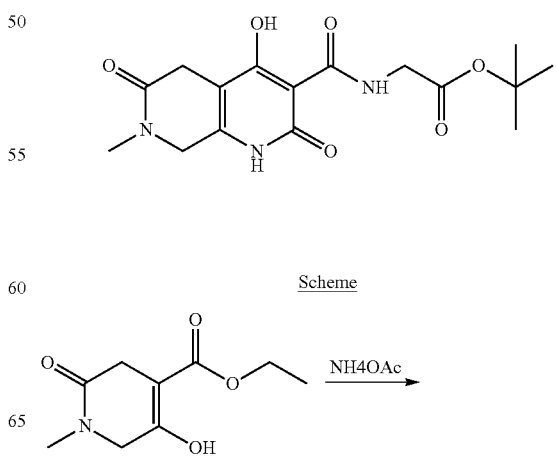

Scheme

-continued

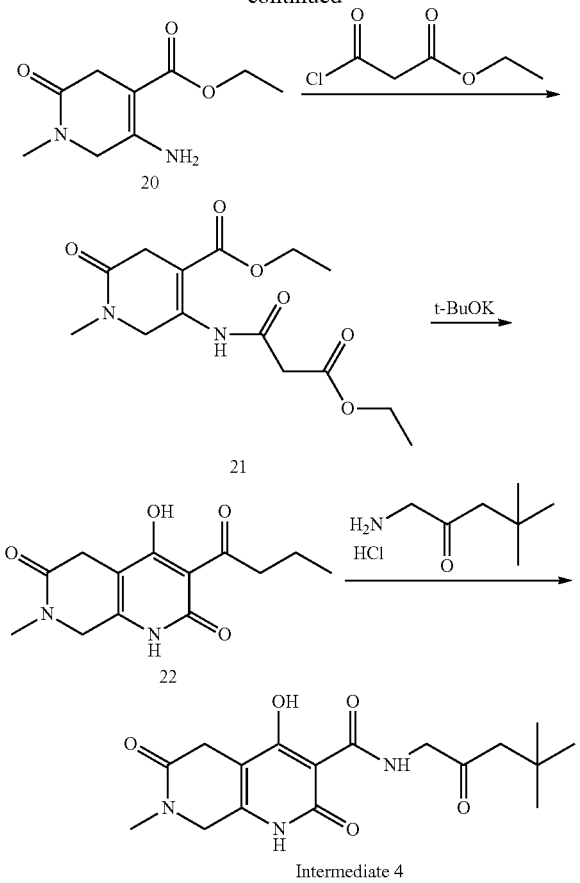

Step A: Ethyl 5-amino-1-methyl-2-oxo-1,2,3,6-tetrahydropyridine-4-carboxylate (20)

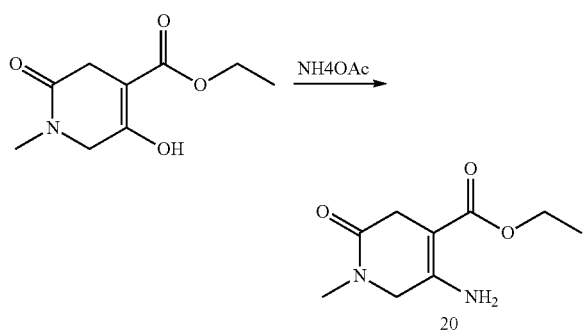

A solution of ethyl 5-hydroxy-1-methyl-2-oxo-1,2,3,6-tetrahydropyridine-4-carboxylate (4 g, 20.08 mmol) and ammonium acetate (7.74 g, 100 mmol) in MeOH (50 mL) was stirred at room temperature for 3 hours. When TLC (petroleum ether:EtOAc=1:1) showed that the reaction was completed, the reaction mixture was concentrated under reduced pressure to remove most of the solvent. The residue was re-dissolved in DCM (150 mL), washed with H$_2$O (100 mL) and brine (100 mL), dried over Na$_2$SO$_4$ and concentrated under reduced pressure to afford ethyl 5-amino-1-methyl-2-oxo-1,2,3,6-tetrahydropyridine-4-carboxylate (20) as a solid. $^1$H NMR (CDCl$_3$, 400 MHz): δ 5.98 (brs, 2H), 4.17 (q, J=7.0 Hz, 2H), 3.97 (t, J=2.5 Hz, 2H), 3.21 (t, J=2.5 Hz, 2H), 3.01 (s, 3H), 1.28 (t, J=6.8 Hz, 3H).

Step B: Ethyl 5-(3-ethoxy-3-oxopropanamido)-1-methyl-2-oxo-1,2,3,6-tetrahydropyridine-4-carboxylate

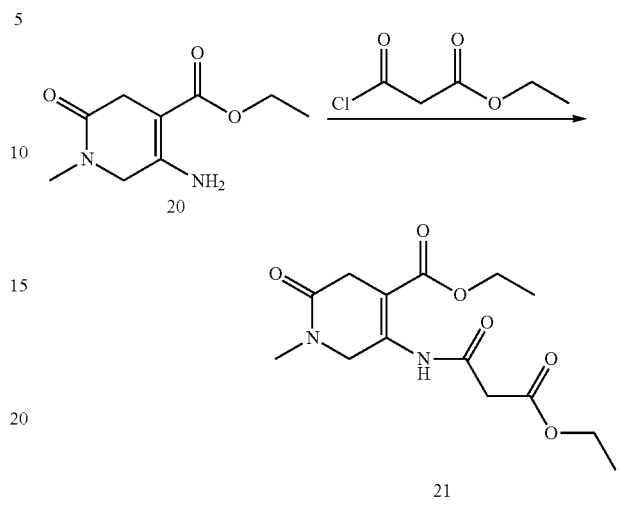

To a solution of ethyl 5-amino-1-methyl-2-oxo-1,2,3,6-tetrahydropyridine-4-carboxylate (Step A product, 2.1 g, 9.53 mmol) in acetonitrile (10 mL) was added ethyl 3-chloro-3-oxopropanoate (4.31 g, 28.6 mmol) at room temperature. Then the reaction mixture was stirred at 45° C. for 1 hour. LCMS showed that the reaction was completed. The reaction mixture was diluted with EtOAc (150 mL) and the organic layer was washed with sat. aq NaHCO$_3$ (150 mL), H$_2$O (150 mL) and brine (150 mL), dried over Na$_2$SO$_4$ and concentrated under reduced pressure to afford ethyl 5-(3-ethoxy-3-oxopropanamido)-1-methyl-2-oxo-1,2,3,6-tetrahydropyridine-4-carboxylate (21) as an oil. $^1$H NMR (CDCl$_3$, 400 MHz): δ 11.82 (s, 1H), 4.78 (t, J=3.8 Hz, 2H), 4.26 (qd, J=7.1 Hz, 1.8 Hz, 4H), 3.44 (s, 2H), 3.26 (t, J=3.5 Hz, 2H), 3.04 (s, 3H), 1.32 (td, J=7.0 Hz, 1.5 Hz, 6H).

Step C: Ethyl 4-hydroxy-7-methyl-2,6-dioxo-1,2,5,6,7,8-hexahydro-1,7-naphthyridine-3-carboxylate

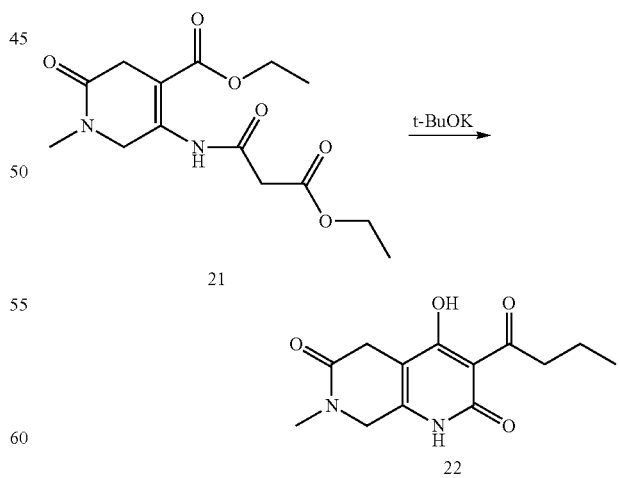

To a solution of ethyl 5-(3-ethoxy-3-oxopropanamido)-1-methyl-2-oxo-1,2,3,6-tetrahydropyridine-4-carboxylate (Step B product, 800 mg, 2.56 mmol) in THF (15 ml) was added potassium 2-methylpropan-2-olate (1 M, 3.84 ml, 3.84 mmol). Then the reaction mixture was heated to 50° C.

and stirred at 50° C. for 0.5 hour. LCMS showed that the reaction was completed. The reaction was acidified by 2 M HCl to pH=5-6. The mixture was dried in vacuo to give crude ethyl 4-hydroxy-7-methyl-2,6-dioxo-1,2,5,6,7,8-hexahydro-1,7-naphthyridine-3-carboxylate (22) as a solid, which was used in the next step directly. LCMS (m/z): 267 (M+H)+.

Step D: tert-Butyl 2-(4-hydroxy-7-methyl-2,6-dioxo-1,2,5,6,7,8-hexahydro-1,7-naphthyridine-3-carboxamido)acetate (Intermediate 4)

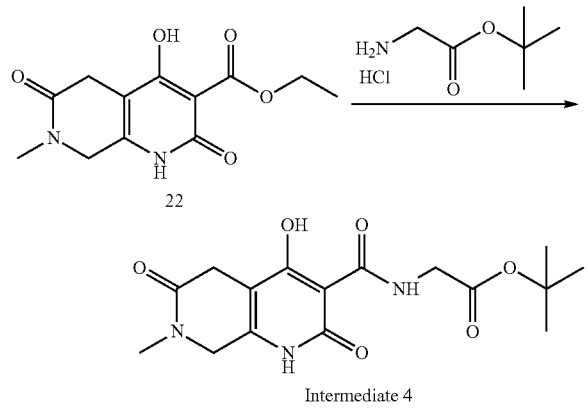

Intermediate 4

To a solution of ethyl 4-hydroxy-7-methyl-2,6-dioxo-1,2,5,6,7,8-hexahydro-1,7-naphthyridine-3-carboxylate (Step C product, 800 mg, 2.254 mmol), tert-butyl 2-aminoacetate hydrochloride (453 mg, 2.70 mmol) and DIPEA (0.905 ml, 5.18 mmol) in toluene (15 ml) was heated to 120° C. and stirred at 120° C. for 2 hours. LCMS showed that the reaction was completed. The resulting mixture was evaporated to give crude product, which was purified by Combi-Flash (MeOH in DCM: 0-7%) to give tert-butyl 2-(4-hydroxy-7-methyl-2,6-dioxo-1,2,5,6,7,8-hexahydro-1,7-naphthyridine-3-carboxamido)acetate (intermediate 4) as a solid. $^1$H NMR (CDCl$_3$, 400 MHz): δ 15.93 (s, 1H), 13.08 (brs, 1H), 10.97 (brs, 1H), 4.60 (s, 2H), 4.13 (d, J=4.0 Hz, 2H), 3.42 (s, 2H), 3.18 (s, 3H), 1.50 (s, 9H).

Example 1

2-(4-Hydroxy-2-oxo-1-(4-(trifluoromethyl)benzyl)-2,5,7,8-tetrahydro-1H-pyrano[4,3-b]pyridine-3-carboxamido)acetic acid

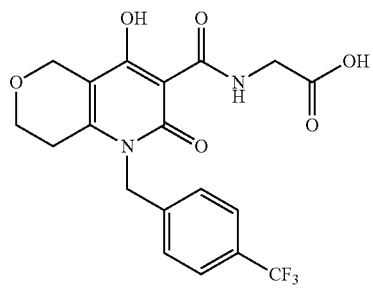

Step A: Isobutyl 4-oxotetrahydro-2H-pyran-3-carboxylate

To a dry ice-acetone cooled solution of dihydro-2H-pyran-4(3H)-one (10.0 g, 100 mmol) in THF (300 mL) was added a solution of Li-HMDS in THF (1.0 M, 110 mL, 110 mmol) dropwise over 30 minutes at −78° C. After the addition, the reaction mixture was stirred at this temperature for 1 hour. To the obtained solution was added isobutyl carbonochloridate (13.6 g, 110 mmol) dropwise at −78° C., and the reaction mixture was stirred at the same temperature for 1 hour. The reaction was quenched with sat. aqueous NH$_4$Cl (100 mL), the organic layer was separated and the aqueous layer was extracted with EtOAc (100 mL). The combined organic layers were washed with H$_2$O (100 mL), brine (100 mL), dried over Na$_2$SO$_4$ and concentrated under reduced pressure to afford a brown oil, which was purified by column chromatography on silica gel (eluted with petroleum ether/EtOAc=15/1) to afford isobutyl 4-oxotetrahydro-2H-pyran-3-carboxylate as an oil. $^1$H NMR (400 MHz, CDCl$_3$) δ: 11.79 (s, 1H), 4.26-4.24 (m, 1H), 4.19 (q, J=2.7 Hz, 1H), 3.91 (t, J=6.4 Hz, 2H), 3.87-3.77 (m, 2H), 2.39-2.28 (m, 2H), 2.03-1.84 (m, 2H), 0.91 (d, J=6.6 Hz, 6H).

Step B: Isobutyl 4-((4-(trifluoromethyl)benzyl)amino)-5,6-dihydro-2H-pyran-3-carboxylate To a solution of isobutyl 4-oxotetrahydro-2H-pyran-3-carboxylate (0.8 g, 4.0 mmol) in anhydrous EtOH (15 mL) was added (4-(trifluoromethyl)phenyl)methanamine (0.84 g, 4.8 mmol), followed by AcOH (0.2 mL). The reaction mixture was then heated to 90° C. and stirred for 5 hours. When TLC showed that the reaction was completed, the reaction mixture was diluted with EtOAc (100 mL), washed with H$_2$O (100 mL) and brine (100 mL), dried over Na$_2$SO$_4$ and concentrated under reduced pressure to afford a yellow oil, which was purified by column chromatography on silica gel (eluted with Petroleum ether/EtOAc=10:1) to afford isobutyl 4-((4-(trifluoromethyl)benzyl)amino)-5,6-dihydro-2H-pyran-3-carboxylate. $^1$H NMR (400 MHz, CDCl$_3$) δ 9.10 (br s, 1H), 7.58 (d, J=8.2 Hz, 2H), 7.37 (d, J=8.2 Hz, 2H), 4.44 (d, J=6.4 Hz, 2H), 4.34 (s, 2H), 3.85 (d, J=6.4 Hz, 2H), 3.76 (t, J=5.6 Hz, 2H), 2.30 (t, J=5.5 Hz, 2H), 1.91-1.87 (m, 1H), 0.92 (d, J=6.6 Hz, 6H). LC/MS (m/z): 358 (M+H)+.

Step C: Isobutyl 4-(3-ethoxy-3-oxo-N-(4-(trifluoromethyl)benzyl)propanamido)-5,6-dihydro-2H-pyran-3-carboxylate To a solution of isobutyl 4-((4-(trifluoromethyl)benzyl)amino)-5,6-dihydro-2H-pyran-3-carboxylate (3.0 g, 8.4 mmol) in CH$_3$CN (10 mL) was added ethyl 3-chloro-3-oxopropanoate (1.9 g, 12.6 mmol). The reaction mixture was heated to 80° C. and stirred for 1 hour. When TLC showed that the reaction was completed, the reaction mixture was diluted with EtOAc (100 mL), washed with sat. aqueous NaHCO$_3$ (100 mL×2), H$_2$O (100 mL) and brine (100 mL), dried over Na$_2$SO$_4$ and concentrated under reduced pressure to afford a brown oil, which was purified by column chromatography on silica gel (eluted with Petroleum ether/EtOAc=3:1) to afford crude product. The crude product was purified by prep. HPLC to afford isobutyl 4-(3-ethoxy-3-oxo-N-(4-(trifluoromethyl)benzyl)propanamido)-5,6-dihydro-2H-pyran-3-carboxylate as an oil. Gemini 150*25 mm*10 um, Mobile phase A: purified water (0.01% NH$_4$HCO$_3$, V/V), Mobile phase B: acetonitrile, A:B=57:43-27:73. $^1$H NMR (400 MHz, CDCl$_3$) δ 7.55 (d, J=8.0 Hz, 2H), 7.44 (d, J=8.0 Hz, 2H), 4.91 (d, J=15.0 Hz, 1H), 4.58 (d, J=15.0 Hz, 1H), 4.44-4.29 (m, 2H), 4.20 (q, J=7.1 Hz, 2H), 3.86-3.82 (m, 1H), 3.76-3.64 (m, 3H), 3.51 (d, J=15.2 Hz, 1H), 3.38 (m, J=15.2 Hz, 1H), 2.40-2.11 (m, 2H), 1.88-1.78 (m, 1H), 1.28 (t, J=7.2 Hz, 3H), 0.87 (dd, J=6.6, 1.1 Hz, 6H). LC/MS (m/z): 472 (M+H)⁺.

Step D: Ethyl 4-hydroxy-2-oxo-1-(4-(trifluoromethyl)benzyl)-2,5,7,8-tetrahydro-1H-pyrano[4,3-b]pyridine-3-carboxylate To a suspension of NaH (8 mg, 0.21 mmol) in toluene (2 mL) was added a solution of methyl isobutyl 4-(3-ethoxy-3-oxo-N-(4-(trifluoromethyl)benzyl)propanamido)-5,6-dihydro-2H-pyran-3-carboxylate (50 mg, 0.11 mmol) in toluene (8 mL), followed by EtOH (0.1 mL). The reaction mixture was stirred at room temperature for 1 hour. The reaction mixture was then poured into 1M HCl (50 mL), extracted with EtOAc (50 mL), washed with H₂O (50 mL) and brine (50 mL), dried over Na₂SO₄ and concentrated under reduced pressure to afford an oil. The crude oil was triturated with petroleum ether, and tert-butyl 2-(4-hydroxy-2-oxo-1-(4-(trifluoromethyl)benzyl)-2,5,7,8-tetrahydro-1H-pyrano[4,3-b]pyridine-3-carboxamido)acetate was collected by suction as a yellow solid, which was used in next step without further purification. ¹H NMR (400 MHz, CDCl₃) δ 13.74 (s, 1H), 7.56 (d, J=7.9 Hz, 2H), 7.24 (d, J=7.9 Hz, 2H), 5.40-5.25 (m, 2H), 4.58 (s, 2H), 4.45 (q, J=7.1 Hz, 2H), 3.84 (t, J=5.5 Hz, 2H), 2.58 (t, J=5.6 Hz, 2H), 1.43 (t, J=7.1 Hz, 3H). LC/MS (m/z): 398 (M+H)⁺.

Step E: tert-Butyl-(4-hydroxy-2-oxo-1-(4-(trifluoromethyl)benzyl)-2,5,7,8-tetrahydro-1H-pyrano[4,3-b]pyridine-3-carboxamido)acetate To a solution of ethyl 4-hydroxy-2-oxo-1-(4-(trifluoromethyl)benzyl)-2,5,7,8-tetrahydro-1H-pyrano[4,3-b]pyridine-3-carboxylate (35 mg, 0.088 mmol) in DME (30 mL) was added tert-butyl 2-aminoacetate hydrochloride (29 mg, 0.18 mmol), followed by DIPEA (45 mg, 0.35 mmol). The reaction mixture was then heated to 90° C. and stirred for 6 hour. When TLC showed that the reaction was completed, the reaction mixture was diluted with EtOAc (50 mL), washed with 1M HCl (50 mL), H₂O (50 mL) and brine (50 mL), dried over Na₂SO₄ and concentrated under reduced pressure to afford tert-butyl 2-(4-hydroxy-2-oxo-1-(4-(trifluoromethyl)benzyl)-2,5,6,8-tetrahydro-1H-pyrano[3,4-b]pyridine-3-carboxamido) acetate as a solid. ¹H NMR (400 MHz, CDCl₃) δ 10.47 (t, J=4.4 Hz, 1H), 7.58 (d, J=8.2 Hz, 2H), 7.22 (d, J=8.2 Hz, 2H), 5.40-5.25 (m, 2H), 4.58 (s, 2H), 4.06 (d, J=5.3 Hz, 2H), 3.86 (t, J=5.5 Hz, 2H), 2.58 (t, J=5.6 Hz, 2H), 1.46 (s, 9H). LC/MS (m/z): 483 (M+H)⁺.

Step F: 2-(4-Hydroxy-2-oxo-1-(4-(trifluoromethyl)benzyl)-2,5,7,8-tetrahydro-1H-pyrano[4,3-b]pyridine-3-carboxamido)acetic acid A solution of tert-butyl-(4-hydroxy-2-oxo-1-(4-(trifluoromethyl)benzyl)-2,5,7,8-tetrahydro-1H-pyrano[4,3-b]pyridine-3-carboxamido)acetate (32 mg, 0.066 mmol) in TFA (2 mL) and DCM (1 mL) was stirred at room temperature for 2 hours. When TLC showed that the reaction was completed, the reaction mixture was concentrated under reduced pressure to afford a yellow solid, which was triturated with MTBE/petroleum ether (1:1, 10 mL), and 2-(4-hydroxy-2-oxo-1-(4-(trifluoromethyl)benzyl)-2,5,7,8-tetrahydro-1H-pyrano[4,3-b]pyridine-3-carboxamido)acetic acid was collected by suction as a powder. ¹H NMR (400 MHz, DMSO-d₆) δ 10.30 (s, 1H), 7.69 (d, J=7.1 Hz, 2H), 7.33 (d, J=7.1 Hz, 2H), 5.34 (s, 2H), 4.44 (s, 2H), 4.01 (d, J=3.1 Hz, 2H), 3.80 (s, 2H), 2.64 (s, 2H). LC/MS (m/z): 427 (M+H)⁺. Human HIF-PHD2 IC₅₀: 19.2 nM.

Example 2

2-(4-Hydroxy-2-oxo-1-(4-(trifluoromethyl)benzyl)-2,5,6,8-tetrahydro-1H-pyrano[3,4-b]pyridine-3-carboxamido)acetic acid

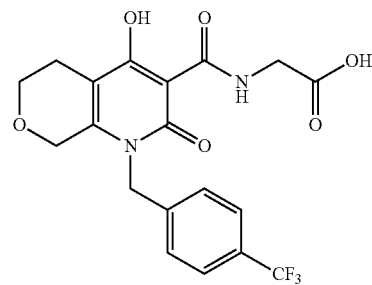 [SMILES: O=C(O)CNC(=O)c1c(O)c2c(n(Cc3ccc(C(F)(F)F)cc3)c1=O)COCC2]

Step A: Methyl 4-hydroxybutanoate

To a solution of gamma-lactone (4.3 g, 50.0 mmol) in MeOH (250.0 mL, 0.20 M) was added Et₃N (42 mL, 300.0 mmol), and the reaction mixture was stirred at 60° C. for 16 h. The reaction mixture was then concentrated under reduced pressure to afford methyl 4-hydroxybutanoate as an oil. ¹H NMR (400 MHz, DMSO-d₆) δ 3.65-3.60 (m, 5H), 2.40 (t, J=7.2 Hz, 2H), 1.87-1.80 (m, 2H).

Step B: Methyl 4-(2-ethoxy-2-oxoethoxy)butanoate

To a suspension of methyl 4-hydroxybutanoate (5.6 g, 27.4 mmol) and dirhodium tetra-acetate (0.1 g) in DCM (100 mL) was added ethyl 2-diazoacetate (3.1 g, 27.4 mmol) dropwise at 0° C. After the addition, the reaction mixture was allowed to warm to room temperature and stirred for 2 hours. When TLC showed that the reaction was completed, the reaction mixture was filtered through a pad of celite and the filtrate was concentrated under reduced pressure to afford the crude product as a oil. The crude product was purified by column chromatography on silica gel (eluted with petroleum ether/EtOAc=12/1) to afford methyl 4-(2-ethoxy-2-oxoethoxy) butanoate as a colorless oil. ¹H NMR (400 MHz, CDCl₃) δ 4.21-4.14 (q, J=7.2 Hz, 2H), 4.03 (s, 2H), 3.65 (s, 3H), 3.55 (t, J=6.2 Hz, 2H), 2.43 (t, J=7.4 Hz, 2H), 1.96-1.86 (m, 2H), 1.28-1.23 (t, J=7.2 Hz, 3H).

Step C: Methyl 3-oxotetrahydro-2H-pyran-4-carboxylate

To a solution of methyl 4-(2-ethoxy-2-oxoethoxy) butanoate (4.8 g, 23.5 mmol) in toluene (100 mL) was added a solution of potassium tert-butoxide in THF (1.0 M, 28 mL, 28.2 mmol) dropwise over 10 minutes at room temperature. After the addition, the reaction mixture was stirred at room temperature for 18 hours. The reaction mixture was then poured into 1M aq. HCl (100 mL), then the organic layer was separated and the aqueous layer was extracted with MTBE (100 mL). The combined organic layers were washed with H₂O (100 mL) and brine (100 mL), dried over Na₂SO₄ and concentrated under reduced pressure to afford an oil, which was purified by column chromatography on silica gel (eluted with Petroleum ether/EtOAc=15/1) to afford a mixture of methyl 3-oxotetrahydro-2H-pyran-4-carboxylate and ethyl 3-oxotetrahydro-2H-pyran-4-carboxylate (2.0 g, about 1:1 ratio) as an oil. $^1$H NMR (400 MHz, CDCl$_3$) δ 11.75 (s, 1H), 4.12 (s, 2H), 3.79-3.76 (m, 5H), 2.34-2.37 (m, 2H).

Step D: Methyl 5-((4-(trifluoromethyl)benzyl)amino)-3,6-dihydro-2H-pyran-4-carboxylate To a solution of methyl 3-oxotetrahydro-2H-pyran-4-carboxylate and ethyl 3-oxotetrahydro-2H-pyran-4-carboxylate (1.0 g, 5.6 mmol) in anhydrous EtOH (20 mL) was added (4-(trifluoromethyl)phenyl)methanamine (1.08 g, 6.1 mmol), followed by AcOH (0.5 mL). The reaction mixture was then heated to 90° C. and stirred for 5 hours. When TLC showed that the reaction was completed, the reaction mixture was concentrated under reduced pressure to remove most of the solvent. The crude oil was extracted with EtOAc (100 mL), washed with H$_2$O (100 mL×2) and brine (100 mL), dried over Na$_2$SO$_4$ and concentrated under reduced pressure to afford methyl 5-((4-(trifluoromethyl)benzyl)amino)-3,6-dihydro-2H-pyran-4-carboxylate as a solid, which was used directly in next step without further purification. $^1$H NMR (400 MHz, CDCl$_3$) δ 8.96 (br s, 1H), 7.59 (d, J=7.9 Hz, 2H), 7.37 (d, J=7.9 Hz, 2H), 4.32 (s, 2H), 4.23 (s, 2H), 3.73-3.67 (m, 5H), 2.37-2.34 (m, 2H).

Step E: Methyl 5-(3-ethoxy-3-oxo-N-(4-(trifluoromethyl)benzyl)propanamido)-3,6-dihydro-2H-pyran-4-carboxylate To a solution of methyl 5-((4-(trifluoromethyl)benzyl)amino)-3,6-dihydro-2H-pyran-4-carboxylate (1.6 g, 5.1 mmol) in CH$_3$CN (6 mL) was added ethyl 3-chloro-3-oxopropanoate (1.1 g, 7.6 mmol). The reaction mixture heated to 70° C. and stirred for 1 hour. When TLC showed that the reaction was completed, the reaction mixture was diluted with EtOAc (100 mL), washed with sat. aq. NaHCO$_3$ (100 mL×2), H$_2$O (100 mL) and brine (100 mL), dried over Na$_2$SO$_4$ and concentrated under reduced pressure to afford methyl 5-(3-ethoxy-3-oxo-N-(4-(trifluoromethyl)benzyl)propanamido)-3,6-dihydro-2H-pyran-4-carboxylate as an oil, which was used in next step without further purification. LC/MS (m/z): 430 (M+H)$^+$.

Step F: Methyl 4-hydroxy-2-oxo-1-(4-(trifluoromethyl)benzyl)-2,5,6,8-tetrahydro-1H-pyrano[3,4-b]pyridine-3-carboxylate To a suspension of NaH (0.28 g, 7.0 mmol) in toluene (10 mL) was added a solution of methyl 5-(3-ethoxy-3-oxo-N-(4-(trifluoromethyl)benzyl) propanamido)-3,6-dihydro-2H-pyran-4-carboxylate (1.5 g, 3.5 mmol) in toluene (20 mL), followed by EtOH (0.2 mL). The reaction mixture was stirred at room temperature for 1 hour. Then the reaction mixture was poured into 1M aq. HCl (100 mL) and extracted with EtOAc (150 mL). The organic layer was washed with H$_2$O (100 mL) and brine (100 mL), dried over Na$_2$SO$_4$ and concentrated under reduced pressure to afford a brown oil. The crude oil was triturated with petroleum ether, and ethyl 4-hydroxy-2-oxo-1-(4-(trifluoromethyl)benzyl)-2,5,6,8-tetrahydro-1H-pyrano[3,4-b] pyridine-3-carboxylate was collected by suction as a solid, which was used in next step without further purification. $^1$H NMR (400 MHz, CDCl$_3$) δ13.86 (s, 1H), 7.56 (d, J=8.2 Hz, 2H), 7.23 (d, J=8.2 Hz, 2H), 4.49-4.39 (m, 4H), 3.84 (t, J=5.6 Hz, 2H), 2.60 (t, J=5.6 Hz, 2H), 1.49-1.38 (m, 3H). LC/MS (m/z): 398 (M+H)$^+$.

Step G: tert-Butyl 2-(4-hydroxy-2-oxo-1-(4-(trifluoromethyl)benzyl)-2,5,6,8-tetrahydro-1H-pyrano[3,4-b]pyridine-3-carboxamido)acetate To a solution of ethyl 4-hydroxy-2-oxo-1-(4-(trifluoromethyl)benzyl)-2,5,6,8-tetrahydro-1H-pyrano[3,4-b]pyridine-3-carboxylate (1.4 g, 3.5 mmol) in DME (30 mL) was added tert-butyl 2-aminoacetate hydrochloride (1.17 g, 7.0 mmol), followed by DIPEA (2.4 mL, 14 mmol). The reaction mixture was then heated to 90° C. and stirred for 6 hours. When TLC showed that the reaction was complete, the reaction mixture was concentrated under reduced pressure to remove most of the solvent, and the residue was extracted with EtOAc (150 mL), washed with 1M HCl (100 mL), H$_2$O (100 mL) and brine (100 mL) successively, then dried over Na$_2$SO$_4$ and concentrated under reduced pressure to afford the crude product as an oil. The crude oil was purified by column chromatography on silica gel (eluted with petroleum ether/EtOAc=5/1) to afford tert-butyl 2-(4-hydroxy-2-oxo-1-(4-(trifluoromethyl)benzyl)-2,5,6,8-tetrahydro-1H-pyrano[3,4-b]pyridine-3-carboxamido)acetate as a solid. $^1$H NMR (400 MHz, CDCl$_3$) δ 10.50 (t, J=4.4 Hz, 1H), 7.58 (d, J=8.2 Hz, 2H), 7.22 (d, J=8.2 Hz, 2H), 5.18 (s, 2H), 4.45 (s, 2H), 4.08 (s, 2H), 3.85 (t, J=5.6 Hz, 2H), 2.61 (t, J=5.6 Hz, 2H), 1.47 (s, 9H). LC/MS (m/z): 483 (M+H)$^+$.

Step H: 2-(4-Hydroxy-2-oxo-1-(4-(trifluoromethyl)benzyl)-2,5,6,8-tetrahydro-1H-pyrano[3,4-b]pyridine-3-carboxamido)acetic acid The solution of tert-butyl 2-(4-hydroxy-2-oxo-1-(4-(trifluoromethyl)benzyl)-2,5,6,8-tetrahydro-1H-pyrano[3,4-b]pyridine-3-carboxamido) acetate (0.6 g, 1.2 mmol) in TFA (20 mL) and DCM (10 mL) was stirred at room temperature for 2 hours. When TLC showed that the reaction was complete, the reaction mixture was concentrated under reduced pressure to afford a yellow solid, which was triturated with MTBE/petroleum ether (1:1, 10 mL), and the precipitate was collected by suction to afford 2-(4-hydroxy-2-oxo-1-(4-(trifluoromethyl)benzyl)-2,5,6,8-tetrahydro-1H-pyrano[3,4-b]pyridine-3-carboxamido)acetic acid as a powder. $^1$H NMR (400 MHz, DMSO-d$_6$) δ 10.31 (s, 1H), 7.70 (d, J=6.8 Hz, 2H), 7.33 (d, J=6.8 Hz, 2H), 5.21 (s, 2H), 4.50 (s, 2H), 4.05 (d, J=3.1 Hz, 2H), 3.78 (br s, 2H), 2.54 (br s, 2H). LC/MS (m/z): 427 (M+H)$^+$. Human HIF-PHD2 IC$_{50}$: 19.8 nM.

Example 3

2-(4-Hydroxy-7-methyl-2,6-dioxo-1-(4-(trifluoromethyl)benzyl)-1,2,5,6,7,8-hexahydro-1,7-naphthyridine-3-carboxamido)acetic acid

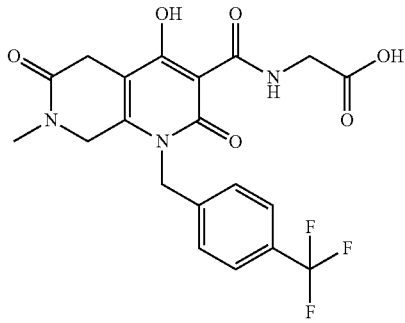 [SMILES: CN1Cc2c(c(O)c(C(=O)NCC(=O)O)c(=O)n2Cc2ccc(C(F)(F)F)cc2)CC1=O]

Step A: Ethyl 4-((2-methoxy-2-oxoethyl)(methyl)amino)-4-oxobutanoate

To a solution of methyl 2-(methylamino)acetate hydrochloride (50 g, 358 mmol) and DIPEA (144 mL, 824 mmol) in DCM (1000 mL) was added ethyl 4-chloro-4-oxobutanoate (70.7 g, 430 mmol) at 0° C. and the mixture was stirred at 0° C. for 30 minutes. Then the reaction was warmed to room temperature and stirred for 16 hours. The resulting mixture was washed with aq NaCl (3×500 mL), dried over Na$_2$SO$_4$, filtered and evaporated in vacuo to give ethyl 4-((2-methoxy-2-oxoethyl)(methyl)amino)-4-oxobutanoate as an oil. $^1$H NMR (CDCl$_3$, 400 MHz): δ 4.11-4.18 (m, 4H), 3.73 (s, 3H), 3.11 (s, 3H), 2.65-2.71 (m, 4H), 1.27 (t, J=7.0 Hz, 3H).

Step B: Ethyl 5-hydroxy-1-methyl-2-oxo-1,2,3,6-tetrahydropyridine-4-carboxylate To a solution of ethyl 4-((2-methoxy-2-oxoethyl)(methyl)amino)-4-oxobutanoate (10 g, 43.2 mmol) in EtOH (300 mL) was added dropwise sodium ethanolate (25.9 mL, 51.9 mmol) under nitrogen. The resulting solution was refluxed for 16 hours. After cooling, 2 M HCl (26.5 mL) was added, and the solution was stirred for 30 minutes, filtered and evaporated in vacuo to give the crude product. The crude product was suspended in DCM (100 mL), stirred, filtered and evaporated in vacuo to give ethyl 5-hydroxy-1-methyl-2-oxo-1,2,3,6-tetrahydropyridine-4-carboxylate as an oil. $^1$H NMR (CDCl$_3$, 400 MHz): δ 11.86 (s, 1H), 4.26 (q, J=7.2 Hz, 2H), 4.04 (t, J=3.5 Hz, 2H), 3.20 (t, J=3.5 Hz, 2H), 3.02 (s, 3H), 1.33 (t, J=7.0 Hz, 3H).

Step C: Ethyl 1-methyl-2-oxo-5-((4-(trifluoromethyl)benzyl)amino)-1,2,3,6-tetrahydropyridine-4-carboxylate To a solution of ethyl 5-hydroxy-1-methyl-2-oxo-1,2,3,6-tetrahydropyridine-4-carboxylate (500 mg, 2.008 mmol) and (4-(trifluoromethyl)phenyl)methanamine (369 mg, 2.108 mmol) in anhydrous EtOH (5 mL) was added AcOH (0.172 mL, 3.01 mmol). Then the reaction mixture was stirred at 90° C. for 4 hours. TLC showed that the reaction completed, and the reaction mixture was concentrated under reduced pressure to remove the solvent. The residue was purified by Combi-Flash (EtOAc in petroleum ether: 0-40%) to afford ethyl 1-methyl-2-oxo-5-((4-(trifluoromethyl)benzyl)amino)-1,2,3,6-tetrahydropyridine-4-carboxylate as an oil. $^1$H NMR (CDCl$_3$, 400 MHz): δ 9.05 (s, 1H), 7.64 (d, J=8.0 Hz, 2H), 7.41 (d, J=8.0 Hz, 2H), 4.45 (d, J=6.5 Hz, 2H), 4.17 (q, J=7.0 Hz, 2H), 4.04 (t, J=2.5 Hz, 2H), 3.24 (brs, 2H), 2.96 (s, 3H), 1.25-1.33 (m, 3H).

Step D: Ethyl 5-(3-ethoxy-3-oxo-N-(4-(trifluoromethyl)benzyl)propanamido)-1-methyl-2-oxo-1,2,3,6-tetrahydropyridine-4-carboxylate To a solution of ethyl 1-methyl-2-oxo-5-((4-(trifluoromethyl)benzyl)amino)-1,2,3,6-tetrahydropyridine-4-carboxylate (370 mg, 0.935 mmol) in acetonitrile (5 mL) was added ethyl 3-chloro-3-oxopropanoate (1407 mg, 9.35 mmol) at room temperature. Then the reaction mixture was heated to 80° C. and stirred for 5 hours. LCMS showed that the reaction was completed, and the reaction mixture was diluted with EtOAc (100 mL), washed with sat. aq. NaHCO$_3$ (100 mL×2), H$_2$O (100 mL) and brine (100 mL), dried over Na$_2$SO$_4$ and concentrated under reduced pressure. The residue was purified by Combi-Flash (EtOAc in petroleum ether: 0-50%) to give ethyl 5-(3-ethoxy-3-oxo-N-(4-(trifluoromethyl)benzyl)propanamido)-1-methyl-2-oxo-1,2,3,6-tetrahydropyridine-4-carboxylate as an oil. $^1$H NMR (CDCl$_3$, 400 MHz): δ 7.61 (d, J=8.0 Hz, 2H), 7.43 (d, J=8.0 Hz, 2H), 4.12-4.29 (m, 8H), 3.41-3.48 (m, 2H), 2.92 (s, 3H), 2.05 (s, 2H), 1.25-1.33 (m, 6H).

Step E: Ethyl 4-hydroxy-7-methyl-2,6-dioxo-1-(4-(trifluoromethyl)benzyl)-1,2,5,6,7,8-hexahydro-1,7-naphthyridine-3-carboxylate To a solution of ethyl 5-(3-ethoxy-3-oxo-N-(4-(trifluoromethyl)benzyl)propanamido)-1-methyl-2-oxo-1,2,3,6-tetrahydropyridine-4-carboxylate (200 mg, 0.340 mmol) in toluene (5 mL) was added potassium 2-methylpropan-2-olate (0.510 mL, 0.510 mmol). Then the reaction mixture was heated to 50° C. and stirred for 0.5 hour. LCMS showed that the reaction was completed. The reaction was acidified by 2 M HCl to pH=5-6. The mixture was evaporated in vacuo to give crude ethyl 4-hydroxy-7-methyl-2,6-dioxo-1-(4-(trifluoromethyl)benzyl)-1,2,5,6,7,8-hexahydro-1,7-naphthyridine-3-carboxylate as a solid which was used in the next step directly. LCMS (m/z): 425 (M+H)$^+$.

Step F: tert-Butyl 2-(4-hydroxy-7-methyl-2,6-dioxo-1-(4-(trifluoromethyl)benzyl)-1,2,5,6,7,8-hexahydro-1,7-naphthyridine-3-carboxamido)acetate A solution of ethyl 4-hydroxy-7-methyl-2,6-dioxo-1-(4-(trifluoromethyl)benzyl)-1,2,5,6,7,8-hexahydro-1,7-naphthyridine-3-carboxylate (150 mg, 0.318 mmol), tert-butyl 2-aminoacetate hydrochloride (64.0 mg, 0.382 mmol) and DIPEA (0.128 mL, 0.732 mmol) in toluene (5 mL) was heated to 120° C. and stirred at 120° C. for 8 hours. The resulting mixture was concentrated in vacuo to give the crude product. Purification by Combi-Flash (MeOH in DCM: 0-7%) gave tert-butyl 2-(4-hydroxy-7-methyl-2,6-dioxo-1-(4-(trifluoromethyl)benzyl)-1,2,5,6,7,8-hexahydro-1,7-naphthyridine-3-carboxamido)acetate as an oil that was used directly in the next step.

Step G: 2-(4-Hydroxy-7-methyl-2,6-dioxo-1-(4-(trifluoromethyl)benzyl)-1,2,5,6,7,8-hexahydro-1,7-naphthyridine-3-carboxamido)acetic acid To a solution of tert-butyl 2-(4-hydroxy-7-methyl-2,6-dioxo-1-(4-(trifluoromethyl)benzyl)-1,2,5,6,7,8-hexahydro-1,7-naphthyridine-3-carboxamido)acetate (295 mg, 0.290 mmol) in DCM (5 mL) was added 2,2,2-trifluoroacetic acid (330 mg, 2.90 mmol). The resulting mixture was stirred at room temperature for 3 hours. LCMS showed that the reaction was completed. The resulting mixture was concentrated vacuo. The residue was purified by prep-HPLC (Column: Gemini C18 150*23.5 mm*10 um; Mobile phase: from 30% MeCN in water (0.225% FA) to 60% MeCN in water (0.225% FA); Wavelength: 220 nm) to give 2-(4-hydroxy-7-methyl-2,6-dioxo-1-(4-(trifluoromethyl)benzyl)-1,2,5,6,7,8-hexahydro-1,7-naphthyridine-3-carboxamido) acetic acid as a solid. $^1$H NMR (DMSO-d$_6$, 400 MHz): δ 10.27 (t, J=5.6 Hz, 1H), 7.71 (d, J=8.4 Hz, 2H), 7.39 (d, J=8.0 Hz, 2H), 5.34 (s, 2H), 4.54 (s, 2H), 4.06 (d, J=5.6 Hz, 2H), 3.23 (s, 2H), 2.87 (s, 3H). LC/MS (m/z): 454 (M+H)$^+$. Human HIF-PHD2 IC$_{50}$: 6.7 nM.

Example 4

2-(4-Hydroxy-2-oxo-2,5,7,8-tetrahydro-1H-pyrano[4,3-b]pyridine-3-carboxamido)acetic acid

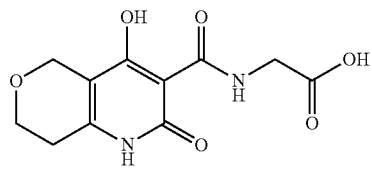 [SMILES: O=C(O)CNC(=O)c1c(O)c2c([nH]c1=O)CCOC2]

To a solution of Intermediate 1 (0.05 g, 0.154 mmol) in DCM (1 mL) was added TFA (0.5 mL). The mixture was stirred at room temperature for 5 h. LCMS showed that the reaction was complete. The mixture was concentrated. To the residue was added MTBE (1 mL) and the mixture was stirred for 30 min. The resulting solid was filtered to give the desired product 2-(4-hydroxy-2-oxo-2,5,7,8-tetrahydro-1H-pyrano[4,3-b]pyridine-3-carboxamido)acetic acid as a solid. $^1$HNMR (DMSO-$d_6$, 400 MHz) δ 15.82 (s, 1H), 11.77 (s, 1H), 10.30 (t, J=5.5 Hz, 1H), 4.36 (s, 2H), 4.03 (d, J=5.9 Hz, 2H), 3.80 (t, J=5.5 Hz, 2H), 2.54 (t, J=5.4 Hz, 2H). LC/MS (m/z): 269 (M+H)$^+$. Human HIF-PHD2 IC$_{50}$: 41.8 nM.

Example 5

2-(1-(4-Cyanobenzyl)-4-hydroxy-2-oxo-2,5,7,8-tetrahydro-1H-pyrano[4,3-b]pyridine-3-carboxamido)acetic acid

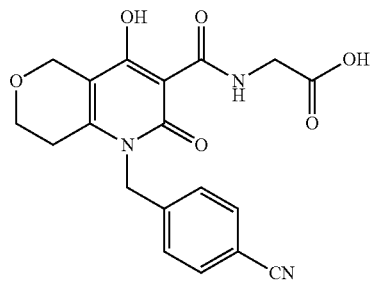 [SMILES: N#Cc1ccc(Cn2c3c(c(O)c(C(=O)NCC(=O)O)c2=O)COCC3)cc1]

Step A: tert-Butyl 2-(1-(4-cyanobenzyl)-4-hydroxy-2-oxo-2,5,7,8-tetrahydro-1H-pyrano[4,3-b]pyridine-3-carboxamido)acetate To a solution of Intermediate 1 (0.1 g, 0.31 mmol) and 4-(bromomethyl)benzonitrile (0.0725 g, 0.37 mmol) in ACN (2 mL) and DMF (1 mL) was added K$_2$CO$_3$ (0.0649 g, 0.47 mmol). The mixture was stirred at 50° C. overnight. LCMS showed that the reaction was complete. To the mixture was added water (10 mL) and the mixture was extracted with EA (5 mL×3). The combined organic layers were concentrated to give the crude product. The crude product was purified by prep TLC (DCM) to give the desired product as an oil. $^1$H NMR (CDCl$_3$, 400 MHz) δ 15.87 (s, 1H), 10.42 (t, J=4.74 Hz, 1H), 7.58-7.63 (m, 2H), 7.22 (d, J=7.94 Hz, 2H), 5.27-5.35 (m, 2H), 4.57 (s, 2H), 4.04-4.09 (m, 2H), 3.86 (t, J=5.18 Hz, 2H), 2.55 (s, 2H), 1.46 (s, 9H).

Step B: 2-(1-(4-Cyanobenzyl)-4-hydroxy-2-oxo-2,5,7,8-tetrahydro-1H-pyrano[4,3-b]pyridine-3-carboxamido)acetic acid To a solution of Step A product (0.024 g, 0.055 mmol) in DCM (1 mL) was added TFA (0.5 mL). The mixture was stirred at room temperature for 3 h. LCMS showed that the reaction was complete. The mixture was concentrated. Then MTBE (1 mL) was added and the mixture was stirred for 30 min. The resulting solid was filtered to give the title compound as a solid. $^1$HNMR (DMSO-d6, 400 MHz) δ 10.27 (t, J=5.4 Hz, 1H), 7.79 (d, J=8.2 Hz, 2H), 7.30 (d, J=7.9 Hz, 2H), 5.32 (s, 2H), 4.43 (s, 2H), 4.03 (d, J=5.5 Hz, 2H), 3.79 (d, J=5.1 Hz, 2H), 2.61 (s, 2H). LC/MS (m/z): 384 (M+H)$^+$. Human HIF-PHD2 IC$_{50}$: 13.9 nM.

Examples 6-23 in Table 1 were prepared following the similar procedures described in Example 5 and using Intermediate 1 and the appropriate starting materials.

TABLE 1

| Examples | Name | Structure | MS m/z (M + 1)$^+$ and human HIF-PHD2 IC$_{50}$ |
|---|---|---|---|
| Example 6 | 2-(4-hydroxy-1-(4-methoxybenzyl)-2-oxo-2,5,7,8-tetrahydro-1H-pyrano[4,3-b]pyridine-3-carboxamido)acetic acid | 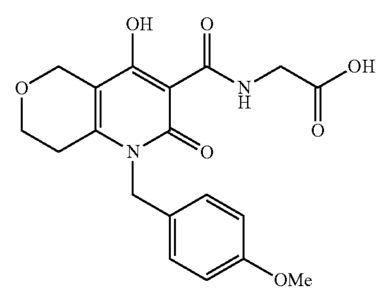 | (M + 1)$^+$ 389 IC$_{50}$ 15.6 nM |

TABLE 1-continued

| Examples | Name | Structure | MS m/z (M + 1)+ and human HIF-PHD2 IC$_{50}$ |
|---|---|---|---|
| Example 7 | 2-(4-hydroxy-2-oxo-1-(4-(trifluoromethoxy)benzyl)-2,5,7,8-tetrahydro-1H-pyrano[4,3-b]pyridine-3-carboxamido)acetic acid | 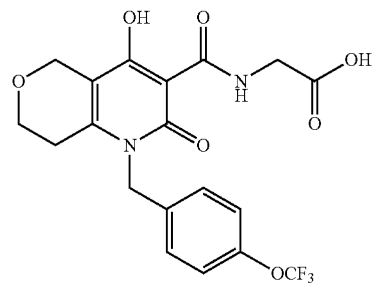 | (M + 1)+ 443<br>IC$_{50}$ 10.3 nM |
| Example 8 | 2-(1-(4-(difluoromethxoy)benzyl)-4-hydroxy-2-oxo-2,5,7,8-tetrahydro-1H-pyrano[4,3-b]pyridine-3-carboxamido)acetic acid | 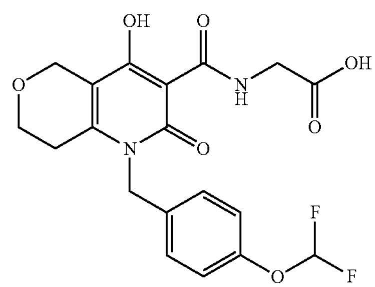 [SMILES: O=C(O)CNC(=O)c1c(O)c2c(n(Cc3ccc(OC(F)F)cc3)c1=O)CCOC2] | (M + 1)+ 423<br>IC$_{50}$ 13.4 nM |
| Example 9 | 2-(1-(4-fluorobenzyl)-4-hydroxy-2-oxo-2,5,7,8-tetrahydro-1H-pyrano[4,3-b]pyridine-3-carboxamido)acetic acid | 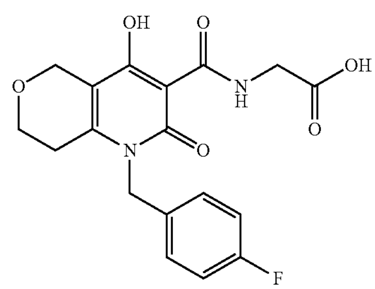 [SMILES: O=C(O)CNC(=O)c1c(O)c2c(n(Cc3ccc(F)cc3)c1=O)CCOC2] | (M + 1)+ 377<br>IC$_{50}$ 13.7 nM |
| Example 10 | 2-(1-(4-chlorobenzyl)-4-hydroxy-2-oxo-2,5,7,8-tetrahydro-1H-pyrano[4,3-b]pyridine-3-carboxamido)acetic acid | 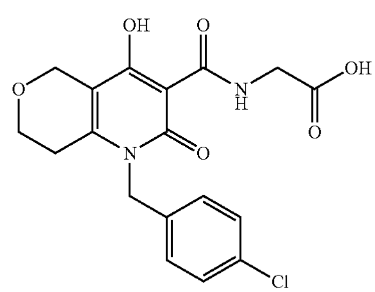 | (M + 1)+ 393<br>IC$_{50}$ 8.5 nM |
| Example 11 | 2-(4-hydroxy-1-(4-(methylsulfonyl)benzyl)-2-oxo-2,5,7,8-tetrahydro-1H-pyrano[4,3-b]pyridine-3-carboxamido)acetic acid | 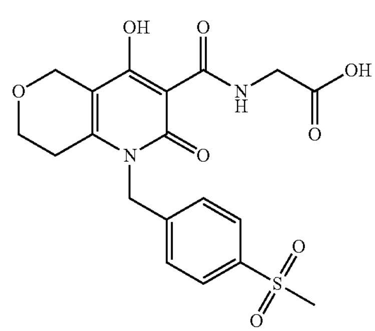 [SMILES: CS(=O)(=O)c1ccc(Cn2c3c(c(O)c(C(=O)NCC(=O)O)c2=O)COCC3)cc1] | (M ' 1)+ 437<br>IC$_{50}$ 20.2 nM |

TABLE 1-continued

| Examples | Name | Structure | MS m/z (M + 1)$^+$ and human HIF-PHD2 IC$_{50}$ |
|---|---|---|---|
| Example 12 | 2-(4-hydroxy-1-(4-isopropylbenzyl)-2-oxo-2,5,7,8-tetrahydro-1H-pyrano[4,3-b]pyridine-3-carboxamido)acetic acid | 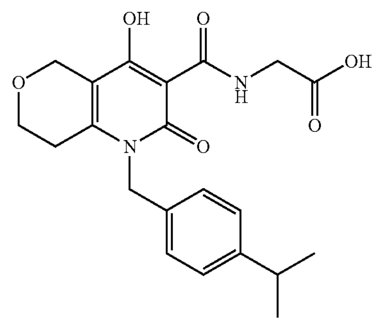 [SMILES: CC(C)c1ccc(Cn2c3c(c(O)c(C(=O)NCC(=O)O)c2=O)COCC3)cc1] | (M + 1)$^+$ 401<br>IC$_{50}$ 12.5 nM |
| Example 13 | 2-(4-hydroxy-1-(4-isopropoxybenzyl)-2-oxo-2,5,7,8-tetrahydro-1H-pyrano[4,3-b]pyridine-3-carboxamido)acetic acid | 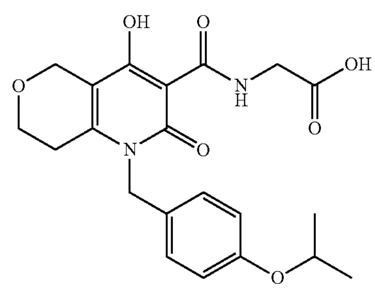 [SMILES: CC(C)Oc1ccc(Cn2c3c(c(O)c(C(=O)NCC(=O)O)c2=O)COCC3)cc1] | (M + 1)$^+$ 417<br>IC$_{50}$ 20.5 nM |
| Example 14 | 2-(1-(benzo[d]thiazol-2-ylmethyl)-4-hydroxy-2-oxo-2,5,7,8-tetrahydro-1H-pyrano[4,3-b]pyridine-3-carboxamido)acetic acid | 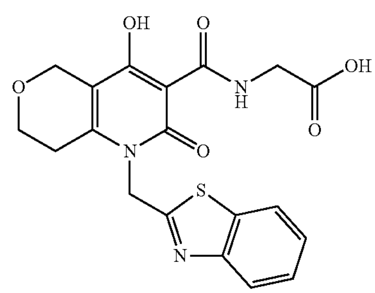 [SMILES: O=C(O)CNC(=O)c1c(O)c2c(n(Cc3nc4ccccc4s3)c1=O)CCOC2] | (M + 1)$^+$ 416<br>IC$_{50}$ 5.4 nM |
| Example 15 | 2-(1-(3,4-difluorobenzyl)-4-hydroxy-2-oxo-2,5,7,8-tetrahydro-1H-pyrano[4,3-b]pyridine-3-carboxamido)acetic acid | 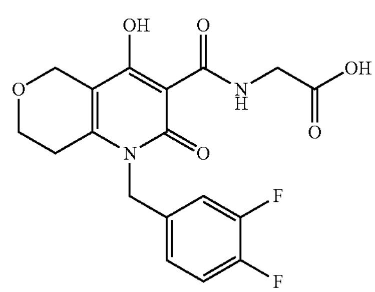 [SMILES: O=C(O)CNC(=O)c1c(O)c2c(n(Cc3ccc(F)c(F)c3)c1=O)CCOC2] | (M + 1)$^+$ 395<br>IC$_{50}$ 14.7 nM |
| Example 16 | 2-(1-(2,4-difluorobenzyl)-4-hydroxy-2-oxo-2,5,7,8-tetrahydro-1H-pyrano[4,3-b]pyridine-3-carboxamido)acetic acid | 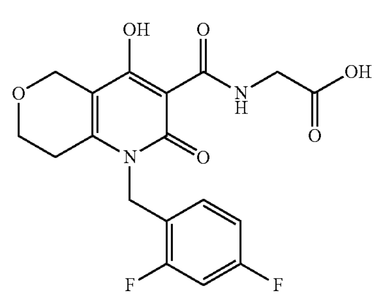 [SMILES: O=C(O)CNC(=O)c1c(O)c2c(n(Cc3ccc(F)cc3F)c1=O)CCOC2] | (M + 1)$^+$ 395<br>IC$_{50}$ 10.3 nM |

TABLE 1-continued

| Examples | Name | Structure | MS m/z (M + 1)+ and human HIF-PHD2 IC$_{50}$ |
|---|---|---|---|
| Example 17 | 2-(1-(4-cyano-2-fluorobenzyl)-4-hydroxy-2-oxo-2,5,7,8-tetrahydro-1H-pyrano[4,3-b]pyridine-3-carboxamido)acetic acid | 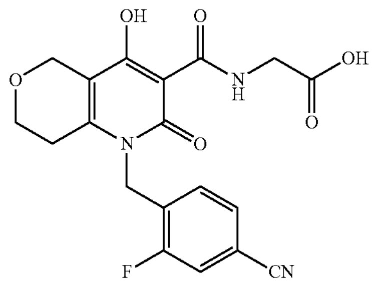 [SMILES: N#Cc1ccc(Cn2c3c(c(O)c(C(=O)NCC(=O)O)c2=O)COCC3)c(F)c1] | (M + )+ 402 IC$_{50}$ 9.0 nM |
| Example 18 | 2-(1-(4-chloro-2-fluorobenzyl)-4-hydroxy-2-oxo-2,5,7,8-tetrahydro-1H-pyrano[4,3-b]pyridine-3-carboxamid)acetic acid | 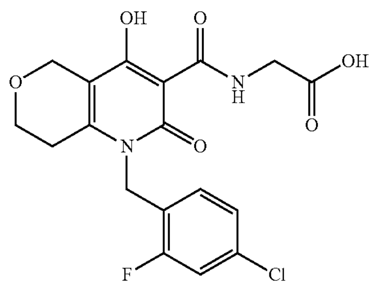 [SMILES: O=C(O)CNC(=O)c1c(O)c2c(n(Cc3ccc(Cl)cc3F)c1=O)CCOC2] | (M + 1)+ 411 IC$_{50}$ 19.2 nM |
| Example 19 | 2-(1-ethyl-4-hydroxy-2-oxo-2,5,7,8-tetrahydro-1H-pyrano[4,3-b]pyridine-3-carboxamido)acetic acid | 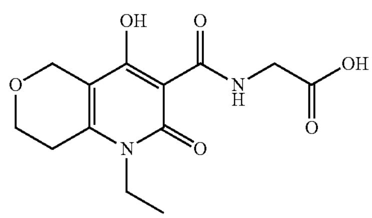 [SMILES: CCn1c2c(c(O)c(C(=O)NCC(=O)O)c1=O)COCC2] | (M + 1)+ 297 IC$_{50}$ 78.5 nM |
| Example 20 | 2-(1-(cyclohexylmethyl)-4-hydroxy-2-oxo-2,5,7,8-tetrahydro-1H-pyrano[4,3-b]pyridine-3-carboxamido)acetic acid | 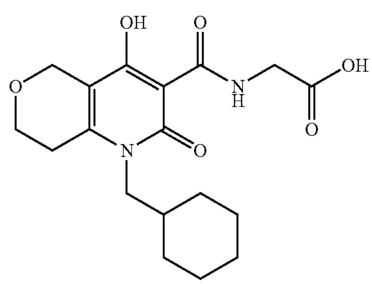 [SMILES: O=C(O)CNC(=O)c1c(O)c2c(n(CC3CCCCC3)c1=O)CCOC2] | (M + 1)+ 365 IC$_{50}$ 76.0 nM |
| Example 21 | 2-(4-hydroxy-1-(naphthalen-2-ylmethyl)-2-oxo-2,5,7,8-tetrahydro-1H-pyrano[4,3-b]pyridine-3-carboxamido)acetic acid | 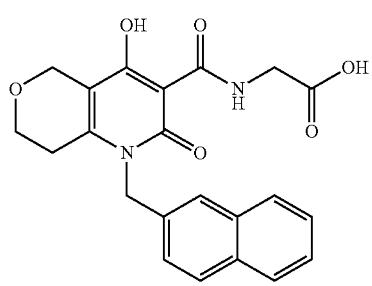 [SMILES: O=C(O)CNC(=O)c1c(O)c2c(n(Cc3ccc4ccccc4c3)c1=O)CCOC2] | (M + 1)+ 409 IC$_{50}$ 37.7 nM |
| Example 22 | 2-(4-hydroxy-1-methyl-2-oxo-2,5,7,8-tetrahydro-1H-pyrano[4,3-b]pyridine-3-carboxamido)acetic acid | 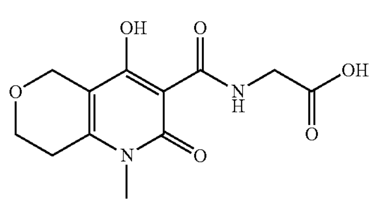 [SMILES: Cn1c2c(c(O)c(C(=O)NCC(=O)O)c1=O)COCC2] | (M + 1)+ 283 IC$_{50}$ 56.1 nM |

TABLE 1-continued

| Examples | Name | Structure | MS m/z (M + 1)+ and human HIF-PHD2 IC$_{50}$ |
|---|---|---|---|
| Example 23 | 2-(4-hydroxy-2-oxo-1-((5-(trifluoromethyl)pyrimidin-2-yl)methyl)-2,5,7,8-tetrahydro-1H-pyrano[4,3-b]pyridine-3-carboxamido)acetic acid | 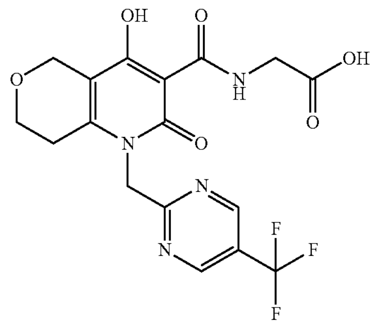 [SMILES: O=C(O)CNC(=O)c1c(O)c2c(n(Cc3ncc(C(F)(F)F)cn3)c1=O)CCOC2] | (M + 1)+ 429 IC$_{50}$ 44.5 nM |

Example 24

2-(4-Hydroxy-2-oxo-1-(2,4,5-trifluorobenzyl)-2,5,7,8-tetrahydro-1H-pyrano[4,3-b]pyridine-3-carboxamido)acetic acid

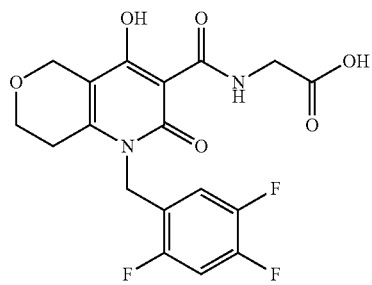

Step A: 1-(Bromomethyl)-2,4,5-trifluorobenzene

To a solution of (2,4,5-trifluorophenyl)methanol (1.0 g, 6.17 mmol) and Ph$_3$P (1.942 g, 7.40 mmol) in DCM (20 ml) was added CBr$_4$ (2.455 g, 7.40 mmol) under N$_2$ at 0° C. After addition, the mixture was warmed to rt and stirred overnight. TLC (PE:EA=10:1) showed the reaction was complete. The solvent was removed and the residue was purified by Combi Flash (EA in PE: 0%-3%) to give 1-(bromomethyl)-2,4,5-trifluorobenzene as an oil. $^1$H NMR (400 MHz, CD$_3$Cl) δ 7.27-7.22 (m, 1H), 6.96-6.94 (m, 1H), 4.43 (s, 2H).

Step B: tert-Butyl 2-(4-hydroxy-2-oxo-1-(2,4,5-trifluorobenzyl)-2,5,7,8-tetrahydro-1H-pyrano[4,3-b]pyridine-3-carboxamido)acetate By using the similar procedure of Step A of Example 5, tert-butyl 2-(4-hydroxy-2-oxo-1-(2,4,5-trifluorobenzyl)-2,5,7,8-tetrahydro-1H-pyrano[4,3-b]pyridine-3-carboxamido)acetate was synthesized. $^1$H NMR (400 MHz, CD$_3$Cl) δ 15.88 (s, 1H), 10.44 (t, J=4.8 Hz, 1H), 7.01-6.83 (m, 2H), 5.22 (s, 2H), 4.57 (s, 2H), 4.08 (d, J=5.3 Hz, 2H), 3.90 (t, J=5.4 Hz, 2H), 2.61 (t, J=5.0 Hz, 2H), 1.48 (s, 9H).

Step C: 2-(4-Hydroxy-2-oxo-1-(2,4,5-trifluorobenzyl)-2,5,7,8-tetrahydro-1H-pyrano[4,3-b]pyridine-3-carboxamido)acetic acid By using the similar procedure of Step B of Example 5, 2-(4-hydroxy-2-oxo-1-(2,4,5-trifluorobenzyl)-2,5,7,8-tetrahydro-1H-pyrano[4,3-b]pyridine-3-carboxamido)acetic acid was synthesized. $^1$HNMR (DMSO-d6, 400 MHz) δ 16.11 (s, 1H), 10.24 (t, J=5.5 Hz, 1H), 7.61 (m, 1H), 7.13-7.06 (m, 1H), 5.21 (s, 2H), 4.47 (s, 2H), 4.06 (d, J=5.5 Hz, 2H), 3.86 (t, J=5.3 Hz, 2H), 2.72 (s, 2H). LC/MS (m/z): 413 (M+H)+. Human HIF-PHD2 IC$_{50}$: 16.8 nM.

Example 25

2-(4-Hydroxy-2-oxo-1-((6-(trifluoromethyl)pyridin-3-yl)methyl)-2,5,7,8-tetrahydro-1H-pyrano[4,3-b]pyridine-3-carboxamido)acetic acid

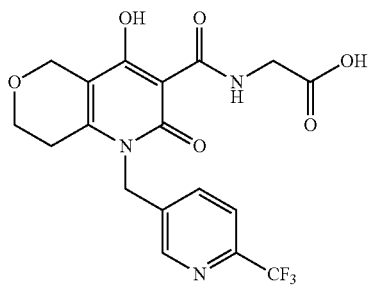 [SMILES: O=C(O)CNC(=O)c1c(O)c2c(n(Cc3ccc(C(F)(F)F)nc3)c1=O)CCOC2]

Step A: (6-(Trifluoromethyl)pyridin-3-yl)methanol

To a solution of 6-(trifluoromethyl)nicotinic acid (2.0 g, 10.47 mmol) in THF (100 ml) was added LAH (0.794 g, 20.93 mmol) under N$_2$ at 0° C. After addition, the mixture was stirred at rt overnight. TLC (PE:EA=1:1) showed the reaction was complete. To the reaction was added Na$_2$SO$_4$.10H$_2$O and the mixture was stirred for 30 min. Then the resulting solid was filtered. To the filtrate was added water (200 mL) and the mixture was extracted with EtOAc (150 mL×3). The combined organic layers were dried and concentrated. The residue was purified by Combi Flash (MeOH in DCM: 0%-4%) to give (6-(trifluoromethyl)pyridin-3-yl)methanol as an oil. $^1$H NMR (400 MHz, CD$_3$Cl) δ 8.66 (s, 1H), 7.89 (d, J=8.0 Hz, 1H), 7.67 (d, J=8.0 Hz, 1H), 4.81 (s, 2H), 3.03 (brs, 1H).

Step B:
5-(Bromomethyl)-2-(trifluoromethyl)pyridine

To a solution of (6-(trifluoromethyl)pyridin-3-yl)methanol (0.64 g, 3.61 mmol) and Ph$_3$P (1.137 g, 4.34 mmol) in DCM (20 ml) was added CBr$_4$ (1.438 g, 4.34 mmol) under N$_2$ at 0° C. After addition, the mixture was warmed to rt and stirred overnight. TLC (PE:EA=10:1) showed the reaction was complete. The solvent was removed and the residue was purified by Combi Flash (EA in PE: 0%-3%) to give 5-(bromomethyl)-2-(trifluoromethyl)pyridine as an oil. $^1$H NMR (400 MHz, CD$_3$Cl) δ 8.73 (s, 1H), 7.91 (d, J=7.9 Hz, 1H), 7.68 (d, J=7.9 Hz, 1H), 4.50 (s, 2H).

Step C: tert-Butyl2-(4-hydroxy-2-oxo-1-((6-(trifluoromethyl)pyridin-3-yl)methyl)-2,5,7,8-tetrahydro-1H-pyrano[4,3-b]pyridine-3-carboxamido)acetate By using the similar procedure of Step A of Example 5, tert-butyl-2-(4-hydroxy-2-oxo-1-((6-(trifluoromethyl)pyridin-3-yl)methyl)-2,5,7,8-tetrahydro-1H-pyrano[4,3-b]pyridine-3-carboxamido)acetate was synthesized. $^1$H NMR (400 MHz, CD$_3$Cl) δ 15.87 (s, 1H), 10.39 (t, J=5.1 Hz, 1H), 8.59 (s, 1H), 7.68-7.59 (m, 2H), 5.34 (s, 2H), 4.54 (s, 2H), 4.06 (d, J=5.3 Hz, 2H), 3.88 (t, J=5.3 Hz, 2H), 2.61 (br s, 2H), 1.46 (s, 9H).

Step D: 2-(4-hydroxy-2-oxo-1-((6-(trifluoromethyl)pyridin-3-yl)methyl)-2,5,7,8-tetrahydro-1H-pyrano[4,3-b]pyridine-3-carboxamido)acetic acid By using the similar procedure of Step B of Example 5, 2-(4-hydroxy-2-oxo-1-((6-(trifluoromethyl)pyridin-3-yl)methyl)-2,5,7,8-tetrahydro-1H-pyrano[4,3-b]pyridine-3-carboxamido)acetic acid was synthesized. $^1$HNMR (DMSO-d$_6$, 400 MHz) δ 16.13 (s, 1H), 12.87 (s, 1H), 10.27 (t, J=5.3 Hz, 1H), 8.69 (s, 1H), 7.88-7.86 (m, 1H), 7.80-7.78 (m, 1H), 5.39 (s, 2H), 4.47 (s, 2H), 4.07 (d, J=5.5 Hz, 2H), 3.87-3.86 (m, 2H), 2.73 (s, 2H). LC/MS (m/z): 428 (M+H)$^+$. Human HIF-PHD2 IC$_{50}$: 10.9 nM.

Example 26

2-(4-Hydroxy-1-(4-(methylcarbamoyl)benzyl)-2-oxo-2,5,7,8-tetrahydro-1H-pyrano[4,3-b]pyridine-3-carboxamido)acetic acid Step A: 4-(Bromomethyl)benzoyl chloride To a solution of 4-(bromomethyl)benzoic acid (2.0 g, 9.30 mmol) in DCM (30 ml) was added (COCl)$_2$ (1.221 ml, 13.95 mmol) and DMF (2 drops) at 0° C. After addition, the mixture was stirred for 2 h, then the solvent was removed and the residue was used directly in the next step.

Step B: 4-(Bromomethyl)-N-methylbenzamide

To a solution of 4-(bromomethyl)benzoyl chloride (1.08 g, 4.63 mmol) in DCM (30 ml) were added methanamine HCl salt (0.468 g, 6.94 mmol) and Et$_3$N (1.934 ml, 13.88 mmol) at 0° C. After addition, the mixture was stirred overnight at rt when TLC (PE:EA=1:1) showed the reaction was complete. To the reaction mixture was added water (100 ml) and the mixture was extracted with EtOAc (50 mL×3). The combined organic layers were washed with brine (50 mL×3), dried and concentrated to give 4-(bromomethyl)-N-methylbenzamide as a solid. $^1$H NMR (400 MHz, CD$_3$Cl) δ 7.77-7.73 (m, 2H), 7.43 (d, J=8.3 Hz, 2H), 4.60 (s, 2H), 3.01 (d, J=4.5 Hz, 3H).

Step C: tert-Butyl 2-(4-hydroxy-1-(4-(methylcarbamoyl)benzyl)-2-oxo-2,5,7,8-tetrahydro-1H-pyrano[4,3-b]pyridine-3-carboxamido)acetate By using the similar procedure of Step A of Example 5, tert-butyl 2-(4-hydroxy-1-(4-(methylcarbamoyl)benzyl)-2-oxo-2,5,7,8-tetrahydro-1H-pyrano[4,3-b]pyridine-3-carboxamido)acetate was synthesized. $^1$H NMR (CDCl$_3$, 400 MHz) δ 15.76 (s, 1H), 10.47 (t, J=5.07 Hz, 1H), 7.66 (d, J=7.94 Hz, 2H), 7.07 (d, J=7.94 Hz, 2H), 6.64 (d, J=4.19 Hz, 1H), 5.25 (s., 2H), 4.51 (s, 2H), 4.03 (d, J=5.29 Hz, 2H), 3.79 (t, J=5.18 Hz, 2H), 2.91 (s, 3H), 2.53 (s, 2H), 1.43 (s, 9H).

Step D: 2-(4-hydroxy-1-(4-(methylcarbamoyl)benzyl)-2-oxo-2,5,7,8-tetrahydro-1H-pyrano[4,3-b]pyridine-3-carboxamido)acetic acid By using the similar procedure of Step B of Example 5, 2-(4-hydroxy-1-(4-(methylcarbamoyl)benzyl)-2-oxo-2,5,7,8-tetrahydro-1H-pyrano[4,3-b]pyridine-3-carboxamido)acetic acid was synthesized. $^1$HNMR (DMSO-d$_6$, 400 MHz) δ 10.31 (s, 1H), 8.35 (d, J=4.40 Hz, 1H), 7.75 (d, J=8.07 Hz, 2H), 7.17 (d, J=8.07 Hz, 2H), 5.29 (s, 2H), 4.43 (s, 2H), 3.98 (d, J=5.14 Hz, 2H), 3.78 (t, J=5.26 Hz, 2H), 2.73 (d, J=4.40 Hz, 3H), 2.63 (s, 2H). LC/MS (m/z): 416 (M+H)$^+$. Human HIF-PHD2 IC$_{50}$: 30.8 nM.

Example 27

2-(4-Hydroxy-1-((1-methyl-1H-pyrazol-3-yl)methyl)-2-oxo-2,5,7,8-tetrahydro-1H-pyrano[4,3-b]pyridine-3-carboxamido)acetic acid

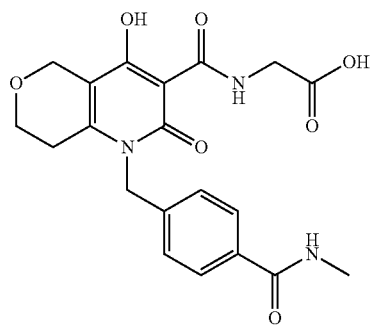 [SMILES: CNC(=O)c1ccc(Cn2c3c(c(O)c(C(=O)NCC(=O)O)c2=O)COCC3)cc1]

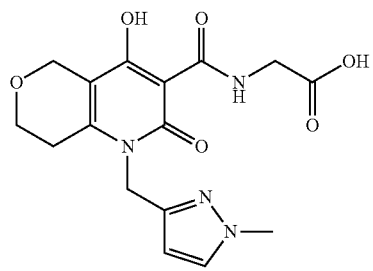

Step A: 3-(Bromomethyl)-1-methyl-1H-pyrazole

To a solution of (1-methyl-1H-pyrazol-3-yl)methanol (0.3 g, 2.68 mmol) and Ph₃P (0.842 g, 3.21 mmol) in DCM (10 ml) was added CBr₄ (1.065 g, 3.21 mmol) under N₂ at 0° C. After addition, the mixture was warmed to rt and stirred overnight. TLC (PE:EA=1:1) showed the reaction was complete. The solvent was removed and the residue was purified by Combi Flash (EA in PE: 0%-3%) to give 3-(bromomethyl)-1-methyl-1H-pyrazole as a solid. ¹H NMR (400 MHz, CD₃Cl) δ 7.29 (d, J=2.0 Hz, 1H), 6.28 (d, J=2.2 Hz, 1H), 4.48 (s, 2H), 3.87 (s, 3H).

Step B: tert-Butyl 2-(4-hydroxy-1-((1-methyl-1H-pyrazol-3-yl)methyl)-2-oxo-2,5,7,8-tetrahydro-1H-pyrano[4,3-b]pyridine-3-carboxamido)acetate By using the similar procedure of Step A of Example 5, tert-butyl 2-(4-hydroxy-1-((1-methyl-1H-pyrazol-3-yl)methyl)-2-oxo-2,5,7,8-tetrahydro-1H-pyrano[4,3-b]pyridine-3-carboxamido)acetate was synthesized. ¹H NMR (CDCl₃, 400 MHz) δ 15.62 (s, 1H), 10.57 (t, J=4.85 Hz, 1H), 7.22 (d, J=1.98 Hz, 1H), 6.19 (d, J=1.98 Hz, 1H), 5.15 (s, 2H), 4.52 (s, 2H), 4.04 (d, J=5.29 Hz, 2H), 3.89 (t, J=5.51 Hz, 2H), 3.79 (s, 3H), 2.92 (t, J=5.29 Hz, 2H), 1.45 (s, 9H).

Step C: 2-(4-Hydroxy-1-((1-methyl-1H-pyrazol-3-yl)methyl)-2-oxo-2,5,7,8-tetrahydro-1H-pyrano[4,3-b]pyridine-3-carboxamido)acetic acid By using the similar procedure of Step B of Example 5, 2-(4-hydroxy-1-((1-methyl-1H-pyrazol-3-yl)methyl)-2-oxo-2,5,7,8-tetrahydro-1H-pyrano[4,3-b]pyridine-3-carboxamido)acetic acid was synthesized. ¹HNMR (DMSO-d6, 400 MHz) δ 15.95 (s, 1H), 12.82 (s, 1H), 10.37 (t, J=5.5 Hz, 1H), 7.57 (d, J=2.0 Hz, 1H), 6.08 (d, J=2.0 Hz, 1H), 5.21 (s, 2H), 4.42 (s, 2H), 4.04 (d, J=5.5 Hz, 2H), 3.84 (t, J=5.5 Hz, 2H), 3.74 (s, 3H), 2.91 (s, 2H). LC/MS (m/z): 363 (M+H)⁺. Human HIF-PHD2 IC₅₀: 32.6 nM.

Example 28

2-(1-(4-Cyano-3-methylbenzyl)-4-hydroxy-2-oxo-2,5,7,8-tetrahydro-1H-pyrano[4,3-b]pyridine-3-carboxamido)acetic acid

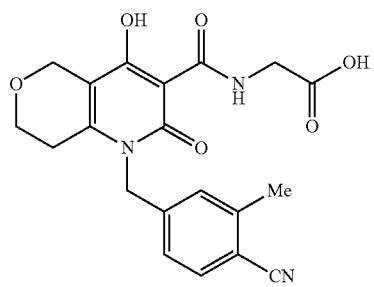 [SMILES: Cc1cc(Cn2c3c(c(O)c(C(=O)NCC(=O)O)c2=O)COCC3)ccc1C#N]

Step A: 4-(Hydroxymethyl)-2-methylbenzonitrile

To a solution of methyl 4-cyano-3-methylbenzoate (2.0 g, 11.42 mmol) in THF (50 ml) was added LiBH₄ (0.298 g, 13.70 mmol) under N₂ at 0° C. After addition, the mixture was stirred at rt overnight. TLC (PE:EA=10:1) showed the reaction was complete. To the reaction mixture was added aq NH₄Cl and the mixture was stirred for 20 min. Then the mixture was extracted with EtOAc (50 mL×3). The combined organic layers were dried and concentrated. The residue was purified by Combi Flash (MeOH in DCM: 0%-1%) to give 4-(hydroxymethyl)-2-methylbenzonitrile as an oil. ¹H (400 MHz, CD₃Cl) δ 7.55 (d, J=8.0 Hz, 1H), 7.31 (s, 1H), 7.25 (d, J=8.0 Hz, 1H), 4.71 (s, 2H), 2.52 (s, 3H).

Step B: 4-(Bromomethyl)-2-methylbenzonitrile

To a solution of 4-(hydroxymethyl)-2-methylbenzonitrile (1.0 g, 6.79 mmol) and Ph₃P (2.139 g, 8.15 mmol) in DCM (20 ml) was added CBr₄ (2.70 g, 8.15 mmol) under N₂ at 0° C. After addition, the mixture was warmed to rt and stirred overnight. TLC (PE:EA=1:1) showed the reaction was complete. The solvent was removed and the residue was purified by Combi Flash (EA in PE: 0%-3%) to give 4-(bromomethyl)-2-methylbenzonitrile as a solid. ¹H NMR (400 MHz, CD₃Cl) δ 7.57 (d, J=7.9 Hz, 1H), 7.33 (s, 1H), 7.29 (d, J=7.9 Hz, 1H), 4.43 (s, 2H), 2.54 (s, 3H).

Step C: tert-Butyl 2-(1-(4-cyano-3-methylbenzyl)-4-hydroxy-2-oxo-2,5,7,8-tetrahydro-1H-pyrano[4,3-b]pyridine-3-carboxamido)acetate By using the similar procedure of Step A of Example 5, tert-butyl 2-(1-(4-cyano-3-methylbenzyl)-4-hydroxy-2-oxo-2,5,7,8-tetrahydro-1H-pyrano[4,3-b]pyridine-3-carboxamido)acetate was synthesized. ¹H NMR (CDCl₃, 400 MHz) δ 15.87 (s, 1H), 10.43 (t, J=4.96 Hz, 1H), 7.54 (d, J=7.94 Hz, 1H), 6.97-7.06 (m, 2H), 5.26 (s, 2H), 4.57 (s, 2H), 4.06 (d, J=5.29 Hz, 2H), 3.86 (t, J=5.40 Hz, 2H), 2.55 (s, 2H), 2.50 (s, 3H), 1.46 (s, 9H).

Step D: 2-(1-(4-Cyano-3-methylbenzyl)-4-hydroxy-2-oxo-2,5,7,8-tetrahydro-1H-pyrano[4,3-b]pyridine-3-carboxamido)acetic acid By using the similar procedure of Step B of Example 5, 2-(1-(4-cyano-3-methylbenzyl)-4-hydroxy-2-oxo-2,5,7,8-tetrahydro-1H-pyrano[4,3-b]pyridine-3-carboxamido)acetic acid was synthesized. ¹HNMR (DMSO-d6, 400 MHz) δ 12.85 (s, 1H), 10.27 (t, J=5.4 Hz, 1H), 7.71 (d, J=7.9 Hz, 1H), 7.22 (s, 1H), 7.06 (d, J=8.2 Hz, 1H), 5.28 (s, 2H), 4.44 (s, 2H), 4.04 (d, J=5.5 Hz, 2H), 3.80 (t, J=5.2 Hz, 2H), 2.63 (d, J=10.1 Hz, 2H), 2.44 (s, 3H). LC/MS (m/z): 398 (M+H)⁺. Human HIF-PHD2 IC₅₀: 14.5 nM.

Example 29

2-(1-(4-Cyano-3-fluorobenzyl)-4-hydroxy-2-oxo-2,5,7,8-tetrahydro-1H-pyrano[4,3-b]pyridine-3-carboxamido)acetic acid

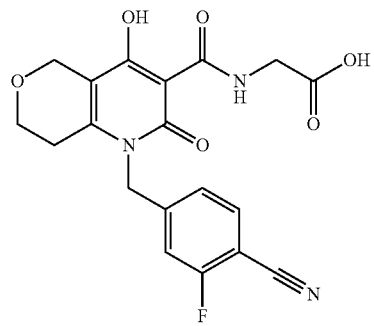 [SMILES: N#Cc1ccc(Cn2c3c(c(O)c(C(=O)NCC(=O)O)c2=O)COCC3)cc1F]

Step A: 4-(Bromomethyl)-2-fluorobenzonitrile

A suspension of 2-fluoro-4-methylbenzonitrile (1.0 g, 7.40 mmol), NBS (1.42 g, 8.88 mmol), AIBN (0.0851 g, 0.518 mmol) in $CCl_4$ (30 mL) was degassed with $N_2$ for 10 minutes at room temperature. Then the mixture was heated at 80° C. for 3 hours. TLC (petroleum ether:EtOAc=10:1) showed that the reaction was completed. The solvent was removed and to the residue was added EtOAc (50 mL). Then the organic layer was washed with water, brine, dried and concentrated. The residue was used directly in the next step. $^1$H NMR ($CDCl_3$, 400 MHz) δ 7.57-7.65 (m, 1H), 7.26 (t, J=7.34 Hz, 2H), 4.43 (s, 2H).

Step B: tert-Butyl 2-(1-(4-cyano-3-fluorobenzyl)-4-hydroxy-2-oxo-2,5,7,8-tetrahydro-1H-pyrano[4,3-b]pyridine-3-carboxamido)acetate By using the similar procedure of Step A of Example 5, tert-butyl 2-(5-(4-cyano-3-fluorobenzyl)-8-hydroxy-6-oxo-3,4,5,6-tetrahydro-1H-isochromene-7-carboxamido)acetate was synthesized as a solid. $^1$H NMR ($CDCl_3$, 400 MHz) δ: 15.89 (s, 1H), 10.36 (t, J=4.96 Hz, 1H), 7.54-7.60 (m, 1H), 7.00 (dd, J=15.99, 8.93 Hz, 2H), 5.21-5.35 (m, 2H), 4.55 (s, 2H), 4.03-4.09 (m, 2H), 3.87 (t, J=5.29 Hz, 2H), 2.55 (brs, 2H), 1.46 (s, 9H).

Step C: 2-(1-(4-Cyano-3-fluorobenzyl)-4-hydroxy-2-oxo-2,5,7,8-tetrahydro-1H-pyrano[4,3-b]pyridine-3-carboxamido)acetic acid By using the similar procedure of Step B of Example 5, 2-(1-(4-cyano-3-fluorobenzyl)-4-hydroxy-2-oxo-2,5,7,8-tetrahydro-1H-pyrano[4,3-b]pyridine-3-carboxamido)acetic acid was synthesized as a solid. $^1$HNMR (DMSO-$d_6$, 400 MHz) δ: 10.23 (t, J=5.50 Hz, 1H), 7.86 (t, J=7.46 Hz, 1H), 7.33 (d, J=10.52 Hz, 1H), 7.11 (d, J=8.07 Hz, 1H), 5.31 (s, 2H), 4.43 (s, 2H), 4.03 (d, J=5.38 Hz, 2H), 3.80 (t, J=5.38 Hz, 2H), 2.62 (t, J=5.38 Hz, 2H). LC/MS (m/z): 402 (M+H)$^+$. Human HIF-PHD2 $IC_{50}$: 16.0 nM.

Example 30

2-(4-Hydroxy-1-((6-methoxypyridin-3-yl)methyl)-2-oxo-2,5,7,8-tetrahydro-1H-pyrano[4,3-b]pyridine-3-carboxamido)acetic acid

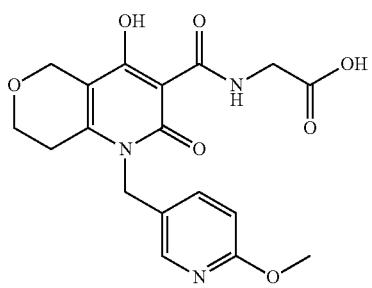 [SMILES: COc1ccc(Cn2c3c(c(O)c(C(=O)NCC(=O)O)c2=O)COCC3)cn1]

Step A: Methyl 6-methoxynicotinate

To a solution of 6-chloronicotinic acid (5 g, 31.7 mmol) in MeOH (50 ml) was added conc. $H_2SO_4$ (0.5 mL). The reaction mixture was refluxed for 12 hours. The solvent was removed and to the residue was added DCM. The mixture was washed with aq. $Na_2CO_3$, brine and dried. The organic layer was concentrated to give methyl 6-methoxynicotinate as a solid, which was used directly in the next step.

Step B: (6-Methoxypyridin-3-yl)methanol

To a solution of methyl 6-methoxynicotinate (3.5 g, 20.94 mmol) in THF (100 ml) was added LAH (1.589 g, 41.9 mmol) under $N_2$ at 0° C. After addition, the mixture was stirred at room temperature overnight. TLC (petroleum ether:EtOAc=1:1) showed the reaction was complete. $Na_2SO_4 \cdot 10H_2O$ was added and the mixture was stirred for 30 minutes. Then the resulting solid was filtered. The filtrate was poured into water (200 mL) and extracted with EtOAc (150 mL×3). The combined organic layers were dried and concentrated. The residue was purified by combi flash (MeOH in DCM: 0%-4%) to give (6-methoxypyridin-3-yl)methanol as an oil. $^1$H NMR ($CDCl_3$, 400 MHz) δ: 8.08 (d, J=2.3 Hz, 1H), 7.62-7.58 (m, 1H), 6.73 (d, J=8.5 Hz, 1H), 4.61 (s, 2H), 3.91 (s, 3H).

Step C: 5-(Bromomethyl)-2-methoxypyridine

To a solution of (6-methoxypyridin-3-yl)methanol (0.72 g, 5.17 mmol) in DCM (20 ml) was added $PBr_3$ (0.244 ml, 2.59 mmol) under $N_2$. After addition, the mixture was stirred at room temperature overnight. The reaction mixture was poured into water (50 mL) and extracted with EtOAc (30 mL×3). The combined organic layers were dried and concentrated to give 5-(bromomethyl)-2-methoxypyridine as an oil, which was used directly in the next step.

Step D: tert-Butyl 2-(4-hydroxy-1-((6-methoxypyridin-3-yl)methyl)-2-oxo-2,5,7,8-tetrahydro-1H-pyrano[4,3-b]pyridine-3-carboxamido)acetate By using the similar procedure of Step A of Example 5, tert-butyl 2-(4-hydroxy-1-((6-methoxypyridin-3-yl)methyl)-2-oxo-2,5,7,8-tetrahydro-1H-pyrano[4,3-b]pyridine-3-carboxamido)acetate was synthesized. $^1$H NMR ($CDCl_3$, 400 MHz) δ: 15.74 (s, 1H), 10.50 (t, J=4.9 Hz, 1H), 7.96 (d, J=2.0 Hz, 1H), 7.43 (dd, J=2.4, 8.6 Hz, 1H), 6.71-6.60 (m, 1H), 5.15 (brs, 2H), 4.50 (s, 2H), 4.04 (d, J=5.1 Hz, 2H), 3.89-3.80 (m, 5H), 2.65 (brs, 2H), 1.45 (s, 9H).

Step E: 2-(4-Hydroxy-1-((6-methoxypyridin-3-yl)methyl)-2-oxo-2,5,7,8-tetrahydro-1H-pyrano[4,3-b]pyridine-3-carboxamido)acetic acid By using the similar procedure of Step B of Example 5, 2-(4-hydroxy-1-((6-methoxypyridin-3-yl)methyl)-2-oxo-2,5,7,8-tetrahydro-1H-pyrano[4,3-b]pyridine-3-carboxamido)acetic acid was synthesized as a solid. $^1$H NMR (DMSO-$d_6$, 400 MHz) δ: 12.85 (s, 1H), 10.34 (t, J=5.51 Hz, 1H), 8.04 (d, J=1.76 Hz, 1H), 7.51 (dd, J=8.49, 2.32 Hz, 1H), 6.77 (d, J=8.60 Hz, 1H), 5.18 (s, 2H), 4.42 (s, 2H), 4.05 (d, J=5.51

Hz, 2H), 3.75-3.87 (m, 5H), 2.73 (s, 2H). LC/MS (m/z): 390 (M+H)+. Human HIF-PHD2 IC$_{50}$: 17.4 nM.

Example 31

2-(4-Hydroxy-2-oxo-1-(thiazol-5-ylmethyl)-2,5,7,8-tetrahydro-1H-pyrano[4,3-b]pyridine-3-carboxamido)acetic acid

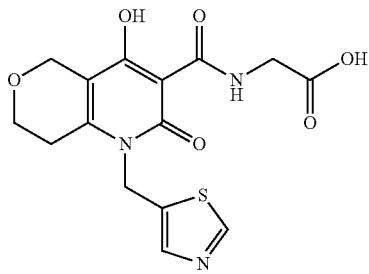 [SMILES: O=C(O)CNC(=O)c1c(O)c2c(n(Cc3cncs3)c1=O)CCOC2]

Step A: 5-(Chloromethyl)thiazole

To thiazol-5-ylmethanol (1 g, 8.68 mmol) was added sulfurous dichloride (20 ml, 8.68 mmol) and the solution was degassed with N$_2$ for 10 minutes at room temperature. Then the mixture was heated at 80° C. for 5 hours. The mixture was concentrated to give the desired product 5-(chloromethyl)thiazole as an oil. $^1$H NMR (400 MHz, CD$_3$Cl) δ: 9.12 (s, 1H), 7.94 (s, 1H), 5.10 (s, 2H).

Step B: tert-Butyl 2-(4-hydroxy-2-oxo-1-(thiazol-5-ylmethyl)-2,5,7,8-tetrahydro-1H-pyrano[4,3-b]pyridine-3-carboxamido)acetate By using the similar procedure of Step A of Example 5, tert-butyl 2-(4-hydroxy-2-oxo-1-(thiazol-5-ylmethyl)-2,5,7,8-tetrahydro-1H-pyrano[4,3-b]pyridine-3-carboxamido)acetate was synthesized as a solid. $^1$H NMR (CDCl$_3$, 400 MHz) δ: 15.76 (s, 1H), 10.42 (t, J=4.77 Hz, 1H), 8.72 (s, 1H), 7.80 (s, 1H), 5.35 (s, 2H), 4.53 (s, 2H), 4.08 (d, J=5.38 Hz, 2H), 3.93 (t, J=5.38 Hz, 2H), 2.80 (t, J=5.14 Hz, 2H), 1.48 (s, 9H).

Step C: 2-(4-Hydroxy-2-oxo-1-(thiazol-5-ylmethyl)-2,5,7,8-tetrahydro-1H-pyrano[4,3-b]pyridine-3-carboxamido)acetic acid By using the similar procedure of Step B of Example 5, 2-(4-hydroxy-2-oxo-1-(thiazol-5-ylmethyl)-2,5,7,8-tetrahydro-1H-pyrano[4,3-b]pyridine-3-carboxamido)acetic acid was synthesized as a solid. $^1$H NMR (DMSO-d$_6$, 400 MHz) δ 12.85 (s, 1H), 10.28 (d, J=5.51 Hz, 1H), 8.99 (s, 1H), 7.94 (s, 1H), 5.39 (s, 2H), 4.40 (s, 2H), 4.07 (d, J=5.51 Hz, 2H), 3.86 (t, J=5.40 Hz, 2H), 2.88 (s, 2H). LC/MS (m/z): 366 (M+H)+. Human HIF-PHD2 IC$_{50}$: 32.8 nM.

Example 32

2-(4-Hydroxy-2-oxo-1-((1-phenyl-1H-pyrazol-3-yl)methyl)-2,5,7,8-tetrahydro-1H-pyrano[4,3-b]pyridine-3-carboxamido)acetic acid

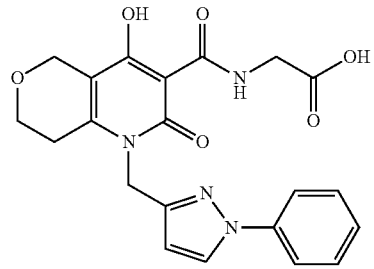 [SMILES: O=C(O)CNC(=O)c1c(O)c2c(n(Cc3ccn(-c4ccccc4)n3)c1=O)CCOC2]

Step A: 3-(Bromomethyl)-1-phenyl-1H-pyrazole

To a solution of 3-methyl-1-phenyl-1H-pyrazole (0.3 g, 1.896 mmol) and NBS (0.405 g, 2.276 mmol) in CCl$_4$ (15 ml) was added AIBN (0.022 g, 0.133 mmol) under N$_2$. After addition, the mixture was stirred at 80° C. for 3 hours. LCMS showed the reaction was completed. The solvent was removed. EtOAc (50 mL) was added to the residue and the solution was washed with water (30 mL×2), brine and dried. The organic layer was concentrated to give a residue which was purified by combi flash (EA in PE: 0%-5%) to give 3-(bromomethyl)-1-phenyl-1H-pyrazole as an oil. $^1$H NMR (400 MHz, CDCl$_3$) δ: 7.86 (d, J=2.4 Hz, 1H), 7.64 (m, 2H), 7.47-7.41 (m, 3H), 7.30-7.24 (m, 1H), 4.58 (s, 2H).

Step B: tert-Butyl 2-(4-hydroxy-2-oxo-1-((1-phenyl-1H-pyrazol-3-yl)methyl)-2,5,7,8-tetrahydro-1H-pyrano[4,3-b]pyridine-3-carboxamido)acetate By using the similar procedure of Step A of Example 5, tert-butyl 2-(4-hydroxy-2-oxo-1-((1-phenyl-1H-pyrazol-3-yl)methyl)-2,5,7,8-tetrahydro-1H-pyrano[4,3-b]pyridine-3-carboxamido)acetate was synthesized as an oil. $^1$H NMR (400 MHz, CDCl$_3$) δ: 15.68 (brs, 1H), 10.60 (t, J=5.02 Hz, 1H), 7.82 (d, J=2.51 Hz, 1H), 7.61 (d, J=8.03 Hz, 2H), 7.44 (t, J=7.78 Hz, 2H), 7.26-7.30 (m, 1H), 6.48 (d, J=2.51 Hz, 1H), 5.27 (s, 2H), 4.57 (s, 2H), 4.09 (d, J=5.02 Hz, 2H), 3.95 (t, J=5.52 Hz, 2H), 3.02 (t, J=5.27 Hz, 2H), 1.49 (s, 9H).

Step C: 2-(4-Hydroxy-2-oxo-1-((1-phenyl-1H-pyrazol-3-yl)methyl)-2,5,7,8-tetrahydro-1H-pyrano[4,3-b]pyridine-3-carboxamido)acetic acid By using the similar procedure of Step B of Example 5, 2-(4-hydroxy-2-oxo-1-((1-phenyl-1H-pyrazol-3-yl)methyl)-2,5,7,8-tetrahydro-1H-pyrano[4,3-b]pyridine-3-carboxamido)acetic acid was synthesized as a solid. $^1$H NMR (DMSO-d$_6$, 400 MHz) δ: 10.35 (t, J=5.40 Hz, 1H), 8.41 (d, J=2.43 Hz, 1H), 7.74 (d, J=7.72 Hz, 2H), 7.46 (t, J=7.94 Hz, 2H), 7.27 (t, J=7.39 Hz, 1H), 6.39 (d, J=2.43 Hz, 1H), 5.25 (s, 2H), 4.43 (s, 2H), 4.00 (d, J=5.29 Hz, 2H), 3.87 (t, J=5.40 Hz, 2H), 2.96 (s, 2H). LC/MS (m/z): 425 (M+H)+. Human HIF-PHD2 IC$_{50}$: 12.1 nM.

Example 33

2-(4-Hydroxy-1-(4-(2-hydroxypropan-2-yl)benzyl)-2-oxo-2,5,7,8-tetrahydro-1H-pyrano[4,3-b]pyridine-3-carboxamido)acetic acid

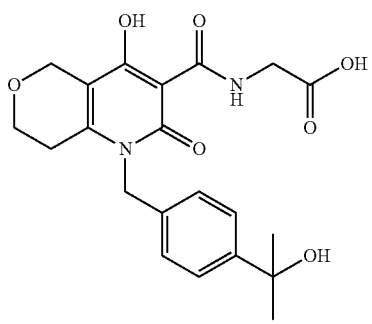 [SMILES: CC(C)(O)c1ccc(Cn2c3c(c(O)c(C(=O)NCC(=O)O)c2=O)COCC3)cc1]

Step A: tert-Butyl 2-(4-hydroxy-1-(4-(2-hydroxypropan-2-yl)benzyl)-2-oxo-2,5,7,8-tetrahydro-1H-pyrano[4,3-b]pyridine-3-carboxamido)acetate Starting with Intermediate 1 and 2-(4-(bromomethyl)phenyl)propan-2-ol and following the similar procedure of Step A of Example 5, tert-butyl 2-(4-hydroxy-1-(4-(2-hydroxypropan-2-yl)benzyl)-2-oxo-2,5,7,8-tetrahydro-1H-pyrano[4,3-b]pyridine-3-carboxamido)acetate was synthesized as a solid. $^1$H NMR (CDCl$_3$, 400 MHz) δ: 15.74 (brs, 1H), 10.53 (t, J=5.3 Hz, 1H), 7.39 (d, J=8.3 Hz, 2H), 7.03 (d, J=8.3 Hz, 2H), 5.23 (brs, 2H), 4.53 (s, 2H), 4.09-3.98 (m, 2H), 3.86-3.74 (m, 2H), 2.68-2.53 (m, 2H), 1.50 (s, 6H), 1.45 (s, 9H).

Step B: 2-(4-Hydroxy-1-(4-(2-hydroxypropan-2-yl)benzyl)-2-oxo-2,5,7,8-tetrahydro-1H-pyrano[4,3-b]pyridine-3-carboxamido)acetic acid To a solution of tert-butyl 2-(4-hydroxy-1-(4-(2-hydroxypropan-2-yl)benzyl)-2-oxo-2,5,7,8-tetrahydro-1H-pyrano[4,3-b]pyridine-3-carboxamido)acetate (Step A product, 90 mg, 0.19 mmol) in THF (2 ml) was added aq. NaOH (0.762 ml, 2.5M, 1.905 mmol). After addition, the mixture was stirred at 40° C. overnight. LCMS showed the reaction was completed. The reaction mixture was extracted with EtOAc (1 ml). The aqueous layer was acidified with 1N HCl to pH=3-4 and then extracted with EtOAc (1 mL×3). The combined organic layers were dried and concentrated to give 2-(4-hydroxy-1-(4-(2-hydroxypropan-2-yl)benzyl)-2-oxo-2,5,7,8-tetrahydro-1H-pyrano[4,3-b]pyridine-3-carboxamido)acetic acid as a solid. $^1$H NMR (DMSO-d$_6$, 400 MHz) δ: 10.36 (t, J=5.5 Hz, 1H), 7.39 (d, J=8.2 Hz, 2H), 7.03 (d, J=8.2 Hz, 2H), 5.22 (brs, 2H), 4.95 (s, 1H), 4.43 (s, 2H), 4.04 (d, J=5.7 Hz, 2H), 3.80 (t, J=5.4 Hz, 2H), 2.67 (brs, 2H), 1.36 (s, 6H). LC/MS (m/z): 417 (M+H)$^+$. Human HIF-PHD2 IC$_{50}$: 49.9 nM.

Example 34

2-(1-(4-Carbamoylbenzyl)-4-hydroxy-2-oxo-2,5,7,8-tetrahydro-1H-pyrano[4,3-b]pyridine-3-carboxamido)acetic acid

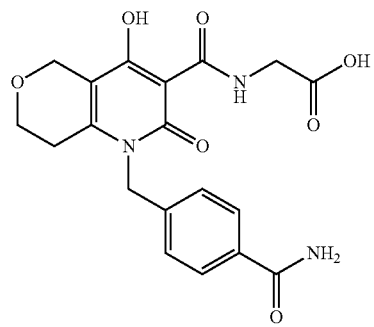

Step A: tert-Butyl 2-(1-(4-cyanobenzyl)-4-hydroxy-2-oxo-2,5,7,8-tetrahydro-1H-pyrano[4,3-b]pyridine-3-carboxamido)acetate Starting with Intermediate 1 and 4-(bromomethyl)benzonitrile and following the similar procedure of Step A of Example 5, tert-butyl 2-(1-(4-cyanobenzyl)-4-hydroxy-2-oxo-2,5,7,8-tetrahydro-1H-pyrano[4,3-b]pyridine-3-carboxamido)acetate was synthesized as a solid. $^1$H NMR (CDCl$_3$, 400 MHz) δ: 15.86 (s, 1H), 10.41 (t, J=4.96 Hz, 1H), 7.60 (d, J=8.16 Hz, 2H), 7.21 (d, J=8.16 Hz, 2H), 5.30 (brs, 2H), 4.56 (s, 2H), 4.05 (d, J=5.29 Hz, 2H), 3.86 (t, J=5.51 Hz, 2H), 2.55 (brs, 2H), 1.46 (s, 9H).

Step B: tert-Butyl 2-(1-(4-carbamoylbenzyl)-4-hydroxy-2-oxo-2,5,7,8-tetrahydro-1H-pyrano[4,3-b]pyridine-3-carboxamido)acetate To a solution of tert-butyl 2-(1-(4-cyanobenzyl)-4-hydroxy-2-oxo-2,5,7,8-tetrahydro-1H-pyrano[4,3-b]pyridine-3-carboxamido)acetate (50.8 mg, 0.116 mmol) in DMSO (1 mL) was added K$_2$CO$_3$ (3.20 mg, 0.023 mmol). To the mixture was added hydrogen peroxide (0.295 ml, 2.89 mmol) slowly at 0° C. and the mixture stirred at 0° C. for 10 min. Then the reaction was warmed to room temperature and stirred overnight. The mixture was poured into water (10 mL) and extracted with EtOAc (5 mL×3). The combined organic layers were concentrated to give the crude product tert-butyl 2-(1-(4-carbamoylbenzyl)-4-hydroxy-2-oxo-2,5,7,8-tetrahydro-1H-pyrano[4,3-b]pyridine-3-carboxamido)acetate as an oil, which was used directly in the next step. LC/MS (m/z): 458 (M+H)$^+$.

Step C: 2-(1-(4-Carbamoylbenzyl)-4-hydroxy-2-oxo-2,5,7,8-tetrahydro-1H-pyrano[4,3-b]pyridine-3-carboxamido)acetic acid By using the similar procedure of Step B of Example 5, 2-(1-(4-carbamoylbenzyl)-4-hydroxy-2-oxo-2,5,7,8-tetrahydro-1H-pyrano[4,3-b]pyridine-3-carboxamido)acetic acid was synthesized as a solid. $^1$H NMR (DMSO-d$_6$, 400 MHz) δ: 10.34 (brs, 1H), 7.93 (brs, 1H), 7.82 (d, J=8.03 Hz, 2H), 7.34 (brs, 1H), 7.19 (d, J=8.53 Hz, 2H), 5.32 (brs, 2H), 4.46

(brs, 2H), 3.93 (brs, 2H), 3.81 (d, J=5.02 Hz, 2H), 2.67 (brs, 2H). LC/MS (m/z): 402 (M+H)$^+$. Human HIF-PHD2 IC$_{50}$: 29.3 nM.

Example 35

2-(4-Hydroxy-2-oxo-1-((2-(trifluoromethyl)thiazol-4-yl)methyl)-2,5,7,8-tetrahydro-1H-pyrano[4,3-b]pyridine-3-carboxamido)acetic acid

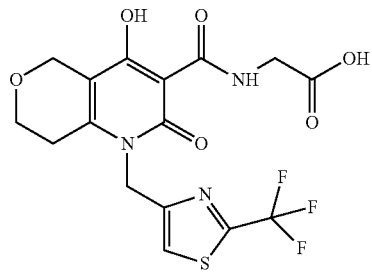 [SMILES: O=C(O)CNC(=O)c1c(O)c2c(n(Cc3csc(C(F)(F)F)n3)c1=O)CCOC2]

Step A: Ethyl 2-(trifluoromethyl)thiazole-4-carboxylate

To a solution of 2,2,2-trifluoroacetamide (7.12 g, 63.0 mmol) in THF (60 ml) was added Lawesson's Reagent (15.29 g, 37.8 mmol) under N$_2$. After addition, the mixture was refluxed overnight. The reaction mixture was cooled to room temperature and ethyl 3-bromo-2-oxopropanoate (12.28 g, 63.0 mmol) was added. Then the mixture was refluxed overnight. After cooling to rt, the reaction mixture was poured into water (200 ml) and extracted with EtOAc (50 mL×3). The combined organic layers were dried and concentrated. The residue was purified by combi flash (EtOAc in petroleum ether: 0%-7%) to give ethyl 2-(trifluoromethyl)thiazole-4-carboxylate as an oil. $^1$H NMR (CDCl$_3$, 400 MHz) δ: 8.37 (s, 1H), 4.44 (q, J=7.09 Hz, 2H), 1.40 (t, J=7.21 Hz, 3H).

Step B: (2-(Trifluoromethyl)thiazol-4-yl)methanol

To a solution of ethyl 2-(trifluoromethyl)thiazole-4-carboxylate (2.0 g, 8.88 mmol) in THF (100 ml) was added DIBAL-H (35.5 ml, 35.5 mmol) under N$_2$ at -78° C. After addition, the mixture was stirred for 4 hours. TLC (petroleum ether:EtOAc=2:1) showed the reaction was completed. The reaction mixture was poured into water (200 ml) and extracted with EtOAc (50 mL×3). The combined organic layers were dried and concentrated. The residue was purified by combi flash (EtOAc in petroleum ether: 0%-20%) to give (2-(trifluoromethyl)thiazol-4-yl)methanol as an oil. $^1$H NMR (CDCl$_3$, 400 MHz) δ: 7.48 (s, 1H), 4.84 (s, 2H), 2.77 (s, 1H).

Step C: 4-(Bromomethyl)-2-(trifluoromethyl)thiazole

To a solution of (2-(trifluoromethyl)thiazol-4-yl)methanol (200 mg, 1.092 mmol) and Ph$_3$P (286 mg, 1.092 mmol) in DCM (10 ml) was added CBr$_4$ (362 mg, 1.092 mmol) under N$_2$ at 0° C. After addition, the mixture was warmed to room temperature and stirred overnight. TLC (petroleum ether: EtOAc=1:1) showed the reaction was completed. The solvent was removed and the residue was purified by combi flash (EtOAc in petroleum ether: 0%-3%) to give 4-(bromomethyl)-2-(trifluoromethyl)thiazole as an oil. $^1$H NMR (CDCl$_3$, 400 MHz) δ: 7.58 (s, 1H), 4.62 (s, 2H).

Step D: tert-Butyl 2-(4-hydroxy-2-oxo-1-((2-(trifluoromethyl)thiazol-4-yl)methyl)-2,5,7,8-tetrahydro-1H-pyrano[4,3-b]pyridine-3-carboxamido)acetate By using the similar procedure of Step A of Example 5, tert-butyl 2-(4-hydroxy-2-oxo-1-((2-(trifluoromethyl)thiazol-4-yl)methyl)-2,5,7,8-tetrahydro-1H-pyrano[4,3-b]pyridine-3-carboxamido)acetate as an oil. $^1$H NMR (CDCl$_3$, 400 MHz) δ: 15.68 (s, 1H), 10.41 (brs, 1H), 7.65 (s, 1H), 5.29 (brs, 2H), 4.53 (s, 2H), 4.04 (d, J=5.14 Hz, 2H), 3.94 (t, J=5.14 Hz, 2H), 2.98 (brs, 2H), 1.46 (s, 9H).

Step E: 2-(4-Hydroxy-2-oxo-1-((2-(trifluoromethyl)thiazol-4-yl)methyl)-2,5,7,8-tetrahydro-1H-pyrano[4,3-b]pyridine-3-carboxamido)acetic acid By using the similar procedure of Step B of Example 5, 2-(4-hydroxy-2-oxo-1-((2-(trifluoromethyl)thiazol-4-yl)methyl)-2,5,7,8-tetrahydro-1H-pyrano[4,3-b]pyridine-3-carboxamido)acetic acid was synthesized as a solid. $^1$H NMR (DMSO-d6, 400 MHz) δ: 10.24 (t, J=5.50 Hz, 1H), 7.92 (s, 1H), 5.34 (s, 2H), 4.44 (s, 2H), 4.03 (d, J=5.62 Hz, 2H), 3.86 (t, J=5.38 Hz, 2H), 2.87 (br. s., 2H). LC/MS (m/z): 434 (M+H)$^+$. Human HIF-PHD2 IC$_{50}$: 15.1 nM.

Example 36

2-(4-Hydroxy-2-oxo-1-(4-(trifluoromethoxy)phenyl)-2,5,7,8-tetrahydro-1H-pyrano[4,3-b]pyridine-3-carboxamido)acetic acid

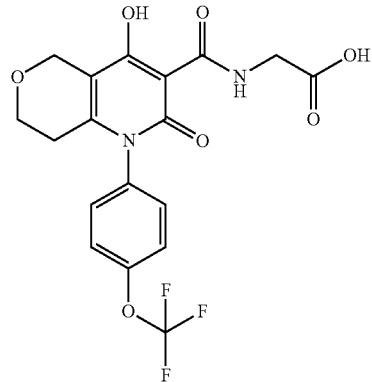 [SMILES: O=C(O)CNC(=O)c1c(O)c2c(n(-c3ccc(OC(F)(F)F)cc3)c1=O)CCOC2]

Step A: tert-Butyl 2-(4-hydroxy-2-oxo-1-(4-(trifluoromethoxy)phenyl)-2,5,7,8-tetrahydro-1H-pyrano[4,3-b]pyridine-3-carboxamido)acetate To a solution of Intermediate 1 (500 mg, 1.54 mmol) and 4-trifluoromethoxy iodobenzene in DMA (2 ml) were added 2-acetylcyclohexanone (108.05 mg, 0.77 mmol) and Cs$_2$CO$_3$ (1.51 g, 4.63 mmol). The mixture was stirred at room temperature for 5 minutes with N$_2$. Copper(I) iodide (1.10 g, 5.78 mmol) was added and the resulting mixture was stirred at room temperature for 5 minutes with N$_2$. Then the reaction mixture was stirred at 120° C. in MW for 1 hour. The mixture was poured into water (50 mL) and extracted with EtOAc (25 mL×3). The combined organic layers were concentrated to give the crude product. The crude product was purified by prep TLC (petroleum ether:EtOAc=4:1) to give the desired product tert-butyl 2-(4-hydroxy-2-oxo-1-(4-(trifluoromethoxy)phenyl)-2,5,7,8-tetrahydro-1H-pyrano[4,3-b]pyridine-3-carboxamido)acetate as an oil. $^1$H NMR (CDCl$_3$, 400 MHz) δ: 15.97 (s, 1H), 10.25 (brs, 1H), 7.36 (d, J=8.56 Hz, 2H), 7.24 (d, J=5.38 Hz, 2H), 4.60 (s, 2H), 4.02 (d, J=5.38 Hz, 2H), 3.83 (t, J=5.38 Hz, 2H), 2.20 (t, J=5.26 Hz, 2H), 1.44 (s, 9H).

Step B: 2-(4-Hydroxy-2-oxo-1-(4-(trifluoromethoxy)phenyl)-2,5,7,8-tetrahydro-1H-pyrano[4,3-b]pyridine-3-carboxamido)acetic acid By using the similar procedure of Step B of Example 5, 2-(4-hydroxy-2-oxo-1-(4-(trifluoromethoxy)phenyl)-2,5,7,8-tetrahydro-1H-pyrano[4,3-b]pyridine-3-carboxamido) acetic acid was synthesized as a solid. $^1$HNMR (DMSO-d$_6$, 400 MHz) δ: 16.21 (s, 1H), 10.13-10.24 (m, 1H), 7.48-7.61 (m, 4H), 4.50 (brs, 2H), 4.05 (d, J=5.52 Hz, 2H), 3.76 (d, J=5.02 Hz, 2H), 2.18 (brs, 2H). LC/MS (m/z): 429 (M+H)$^+$. Human HIF-PHD2 IC$_{50}$: 98.8 nM.

Example 37

2-(1-(4-Chlorobenzyl)-4-hydroxy-2-oxo-2,5,6,8-tetrahydro-1H-pyrano[3,4-b]pyridine-3-carboxamido)acetic acid

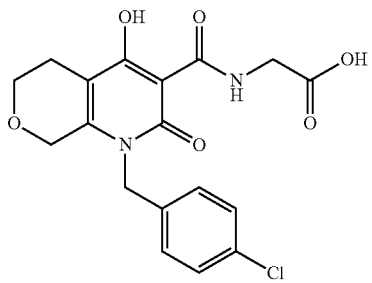 [SMILES: O=C(O)CNC(=O)c1c(O)c2c(n(Cc3ccc(Cl)cc3)c1=O)COCC2]

Step A: tert-Butyl 2-(1-(4-chlorobenzyl)-4-hydroxy-2-oxo-2,5,6,8-tetrahydro-1H-pyrano[3,4-b]pyridine-3-carboxamido)acetate To a solution of Intermediate 2 (100 mg, 0.308 mmol) and 1-(bromomethyl)-4-chlorobenzene (76 mg, 0.370 mmol) in acetone (2 ml) and DMF (1 ml) was added K$_2$CO$_3$ (63.9 mg, 0.462 mmol). The mixture was stirred at 50° C. for overnight. TLC showed that the reaction was complete. The mixture was poured into water (10 mL) and extracted with EtOAc (5 mL×3). The combined organic layers were concentrated to give the crude product. The crude product was purified by prep.TLC (petroleum ether:EtOAc=5:1) to give the desired product tert-butyl 2-(1-(4-chlorobenzyl)-4-hydroxy-2-oxo-2,5,6,8-tetrahydro-1H-pyrano[3,4-b]pyridine-3-carboxamido)acetate as a solid. $^1$H NMR (CDCl$_3$, 400 MHz) δ: 15.93 (s, 1H), 10.53 (brs, 1H), 7.28 (d, J=8.38 Hz, 2H), 7.05 (d, J=8.16 Hz, 2H), 5.10 (d, J=8.38 Hz, 2H), 4.45 (s, 2H), 4.05-4.09 (m, 2H), 3.83 (t, J=5.51 Hz, 2H), 2.59 (t, J=5.18 Hz, 2H), 1.47 (s, 9H).

Step B: 2-(1-(4-Chlorobenzyl)-4-hydroxy-2-oxo-2,5,6,8-tetrahydro-1H-pyrano[3,4-b]pyridine-3-carboxamido)acetic acid To a solution of tert-butyl 2-(1-(4-chlorobenzyl)-4-hydroxy-2-oxo-2,5,6,8-tetrahydro-1H-pyrano[3,4-b]pyridine-3-carboxamido)acetate (Step A product, 63.6 mg, 0.142 mmol) in DCM (1.5 ml) was added TFA (0.5 ml, 6.49 mmol) and the mixture stirred for 3 hours. Then the solvent was removed. To the residue were added MTBE (1.5 mL) and DCM (3 drops) and the mixture was stirred for 2 hours. Filtration to collect the resulting solid afforded 2-(1-(4-chlorobenzyl)-4-hydroxy-2-oxo-2,5,6,8-tetrahydro-1H-pyrano[3,4-b]pyridine-3-carboxamido)acetic acid as a solid. $^1$H NMR (DMSO-d$_6$, 400 MHz) δ: 10.31-10.36 (m, 1H), 7.38 (d, J=8.38 Hz, 2H), 7.14 (d, J=8.38 Hz, 2H), 5.11 (s, 2H), 4.50 (s, 2H), 4.02 (d, J=5.51 Hz, 2H), 3.77 (t, J=5.51 Hz, 2H), 2.50 (t, J=5.51 Hz, 2H). LC/MS (m/z): 393 (M+H)$^+$. Human HIF-PHD2 IC$_{50}$: 50.2 nM.

Examples 38-62 in Table 2 were prepared following the similar procedures described in Example 37 and using Intermediate 2 and the appropriate starting materials.

TABLE 2

| Examples | Name | Structure | MS m/z (M + 1)$^+$ and human HIF-PHD2 IC$_{50}$ |
|---|---|---|---|
| Example 38 | 2-(1-(2,4-difluorobenzyl)-4-hydroxy-2-oxo-2,5,6,8-tetrahydro-1H-pyrano[3,4-b]pyridine-3-carboxamido)acetic acid | 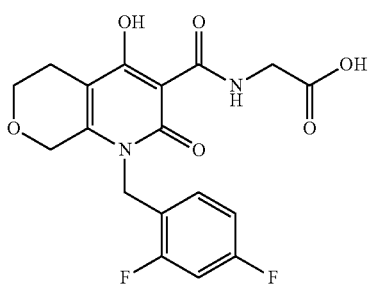 | (M + 1)$^+$ 395 IC$_{50}$ 24.1 nM |

TABLE 2-continued

| Examples | Name | Structure | MS m/z (M + 1)+ and human HIF-PHD2 IC$_{50}$ |
|---|---|---|---|
| Example 39 | 2-(4-hydroxy-1-(4-isopropylbenzyl)-2-oxo-2,5,6,8-tetrahydro-1H-pyrano[3,4-b]pyridine-3-carboxamido)acetic acid | 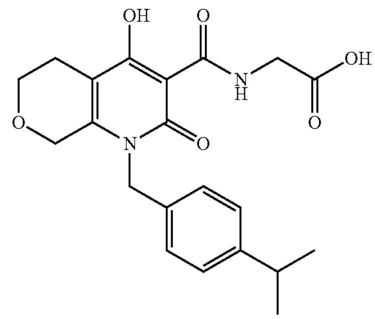 [SMILES: CC(C)c1ccc(Cn2c3c(c(O)c(C(=O)NCC(=O)O)c2=O)CCOC3)cc1] | (M + 1)+ 401 IC$_{50}$ 42.2 nM |
| Example 40 | 2-(1-(4-cyanobenzyl)-4-hydroxy-2-oxo-2,5,6,8-tetrahydro-1H-pyrano[3,4-b]pyridine-3-carboxamido)acetic acid | 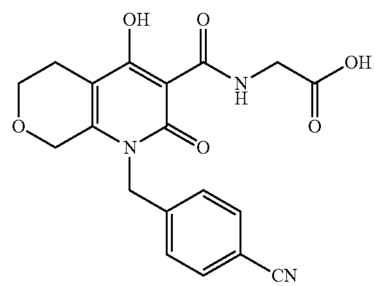 | (M + 1)+ 384 IC$_{50}$ 21.8 nM |
| Example 41 | 2-(4-hydroxy-1-(4-(methylsulfonyl)benzyl)-2-oxo-2,5,6,8-tetrahydro-1H-pyrano[3,4-b]pyridine-3-carboxamido)acetic acid | 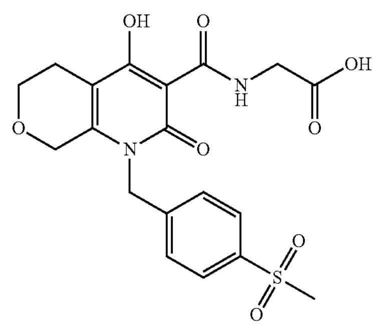 [SMILES: CS(=O)(=O)c1ccc(Cn2c3c(c(O)c(C(=O)NCC(=O)O)c2=O)CCOC3)cc1] | (M + 1)+ 437 IC$_{50}$ 28.7 nM |
| Example 42 | 2-(4-hydroxy-2-oxo-1-((6-(trifluoromethyl)pyridin-3-yl)methyl)-2,5,6,8-tetrahydro-1H-pyrano[3,4-b]pyridine-3-carboxamido)acetic acid | 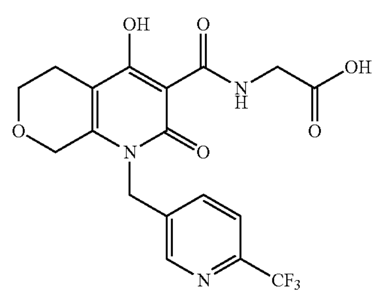 | (M + 1)+ 428 IC$_{50}$ 19.9 nM |
| Example 43 | 2-(4-hydroxy-2-oxo-1-(2,4,5-trifluorobenzyl)-2,5,6,8-tetrahydro-1H-pyrano[3,4-b]pyridine-3-carboxamido)acetic acid | 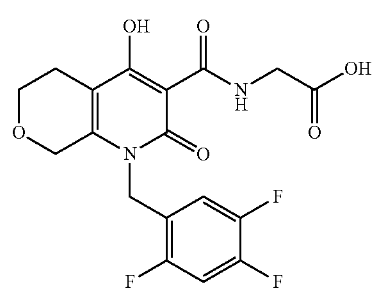 | (M + 1)+ 413 IC$_{50}$ 26.5 nM |

TABLE 2-continued

| Examples | Name | Structure | MS m/z (M + 1)+ and human HIF-PHD2 IC$_{50}$ |
|---|---|---|---|
| Example 44 | 2-(1-(4-cyano-2-fluorobenzyl)-4-hydroxy-2-oxo-2,5,6,8-tetrahydro-1H-pyrano[3,4-b]pyridine-3-carboxamido)acetic acid | 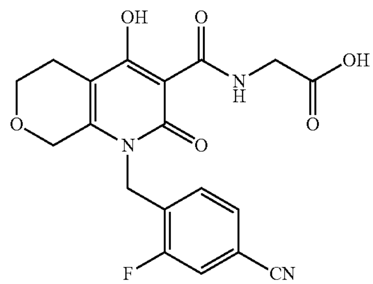 [SMILES: N#Cc1ccc(Cn2c3c(c(O)c(C(=O)NCC(=O)O)c2=O)CCOC3)c(F)c1] | (M + 1)+ 402<br>IC$_{50}$ 14.4 nM |
| Example 45 | 2-(1-(4-cyano-3-methylbenzyl)-4-hydroxy-2-oxo-2,5,6,8-tetrahydro-1H-pyrano[3,4-b]pyridine-3-carboxamido)acetic acid | 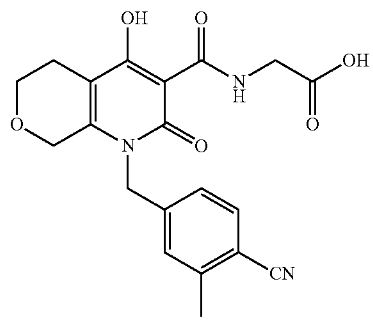 [SMILES: Cc1cc(Cn2c3c(c(O)c(C(=O)NCC(=O)O)c2=O)CCOC3)ccc1C#N] | (M + 1)+ 398<br>IC$_{50}$ 90.1 nM |
| Example 46 | 2-(4-hydroxy-2-oxo-1-((5-(trifluoromethyl)pyrimidin-2-yl)methyl)-2,5,6,8-tetrahydro-1H-pyrano[3,4-b]pyridine-3-carboxamido)acetic acid | 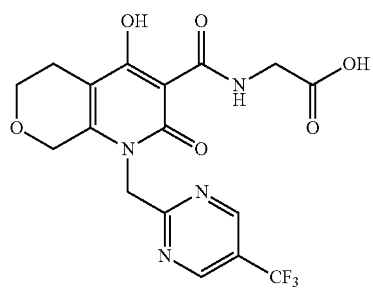 | (M + 1)+ 398<br>IC$_{50}$ 90.1 nM |
| Example 47 | 2-(1-(4-chloro-2-fluorobenzyl)-4-hydroxy-2-oxo-2,5,6,8-tetrahydro-1H-pyrano[3,4-b]pyridine-3-carboxamido)acetic acid | 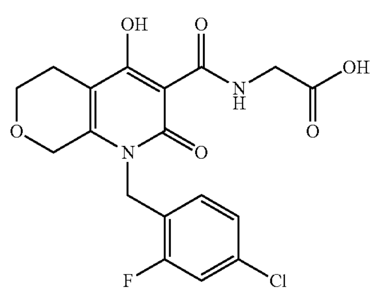 [SMILES: O=C(O)CNC(=O)c1c(O)c2c(n(Cc3ccc(Cl)cc3F)c1=O)COCC2] | (M + 1)+ 412<br>IC$_{50}$ 19.3 nM |
| Example 48 | 2-(1-(benzo[d]thiazol-2-ylmethyl)-4-hydroxy-2-oxo-2,5,6,8-tetrahydro-1H-pyrano[3,4-b]pyridine-3-carboxamido)acetic acid | 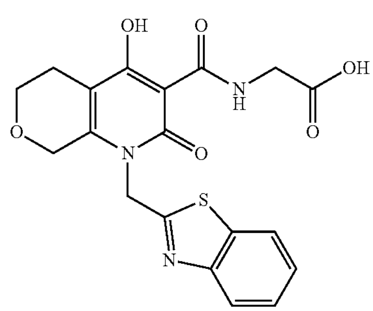 [SMILES: O=C(O)CNC(=O)c1c(O)c2c(n(Cc3nc4ccccc4s3)c1=O)COCC2] | (M + 1)+ 416<br>IC$_{50}$ 8.9 nM |

TABLE 2-continued

| Examples | Name | Structure | MS m/z (M + 1)+ and human HIF-PHD2 IC$_{50}$ |
|---|---|---|---|
| Example 49 | 2-(1-(4-(difluoromethoxy)benzyl)-4-hydroxy-2-oxo-2,5,6,8-tetrahydro-1H-pyrano[3,4-b]pyridine-3-carboxamido)acetic acid | 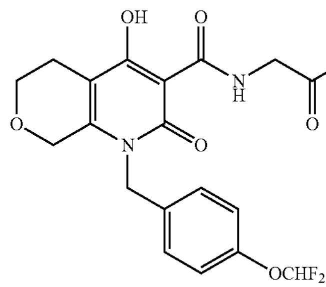 | (M + 1)+ 425<br>IC$_{50}$ 28.6 nM |
| Example 50 | 2-(4-hydroxy-1-((1-methyl-1H-pyrazol-3-yl)methyl)-2-oxo-2,5,6,8-tetrahydro-1H-pyrano[3,4-b]pyridine-3-carboxamido)acetic acid | 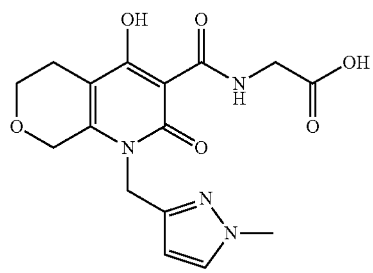 [SMILES: Cn1ccc(Cn2c3c(c(O)c(C(=O)NCC(=O)O)c2=O)CCOC3)n1] | (M + 1)+ 363<br>IC$_{50}$ 55.1 nM |
| Example 51 | 2-(4-hydroxy-1-(4-methoxybenzyl)-2-oxo-2,5,6,8-tetrahydro-1H-pyrano[3,4-b]pyridine-3-carboxamido)acetic acid | 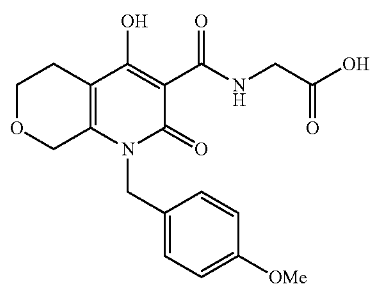 [SMILES: COc1ccc(Cn2c3c(c(O)c(C(=O)NCC(=O)O)c2=O)CCOC3)cc1] | (M + 1)+ 389<br>IC$_{50}$ 30.2 nM |
| Example 52 | 2-(4-hydroxy-2-oxo-1-(4-(trifluoromethoxy)benzyl)-2,5,6,8-tetrahydro-1H-pyrano[3,4-b]pyridine-3-carboxamido)acetic acid | 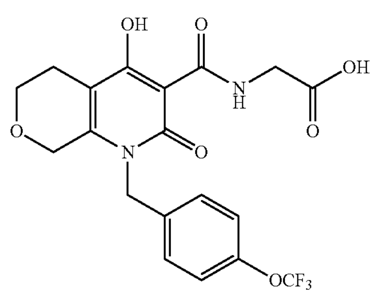 | (M + 1)+ 443<br>IC$_{50}$ 24.1 nM |
| Example 53 | 2-(1-(4-fluorobenzyl)-4-hydroxy-2-oxo-2,5,6,8-tetrahydro-1H-pyrano[3,4-b]pyridine-3-carboxamido)acetic acid | 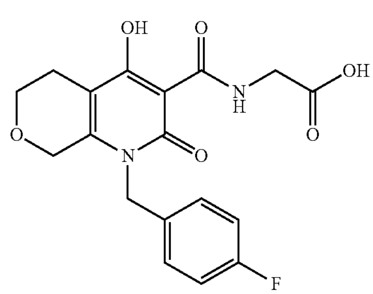 [SMILES: O=C(O)CNC(=O)c1c(O)c2c(n(Cc3ccc(F)cc3)c1=O)COCC2] | (M + 1)+ 377<br>IC$_{50}$ 29.3 nM |

TABLE 2-continued

| Examples | Name | Structure | MS m/z (M + 1)+ and human HIF-PHD2 IC$_{50}$ |
|---|---|---|---|
| Example 54 | 2-(1-(3,4-difluorobenzyl)-4-hydroxy-2-oxo-2,5,6,8-tetrahydro-1H-pyrano[3,4-b]pyridine-3-carboxamido)acetic acid | 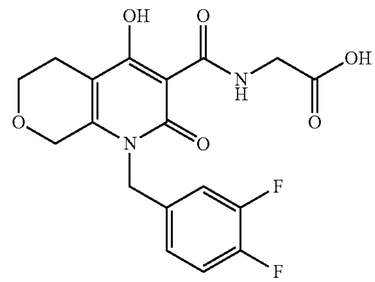 [SMILES: O=C(O)CNC(=O)c1c(O)c2c(n(Cc3ccc(F)c(F)c3)c1=O)COCC2] | (M + 1)+ 395<br>IC$_{50}$ 30.8 nM |
| Example 55 | 2-(4-hydroxy-1-(4-(methylcarbamoyl)benzyl)-2-oxo-2,5,6,8-tetrahydro-1H-pyrano[3,4-b]pyridine-3-carboxamido)acetic acid | 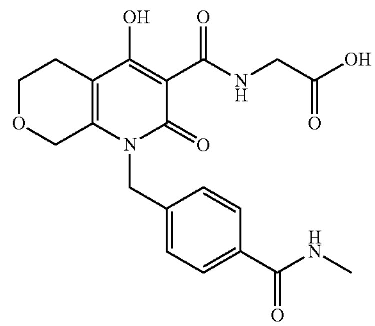 | (M + 1)+416<br>IC$_{50}$ 21.3 nM |
| Example 56 | 2-(4-hydroxy-1-(4-isopropoxybenzyl)-2-oxo-2,5,6,8-tetrahydro-1H-pyrano[3,4-b]pyridine-3-carboxamido)acetic acid | 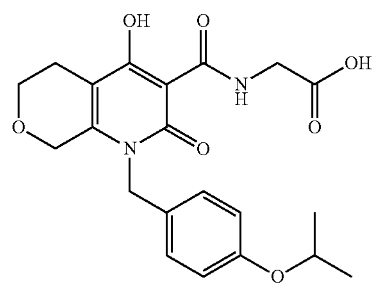 [SMILES: CC(C)Oc1ccc(Cn2c3c(c(O)c(C(=O)NCC(=O)O)c2=O)CCOC3)cc1] | (M + 1)+ 417<br>IC$_{50}$ 29.1 nM |
| Example 57 | 2-(1-(3-cyanobenzyl)-4-hydroxy-2-oxo-2,5,6,8-tetrahydro-1H-pyrano[3,4-b]pyridine-3-carboxamido)acetic acid | 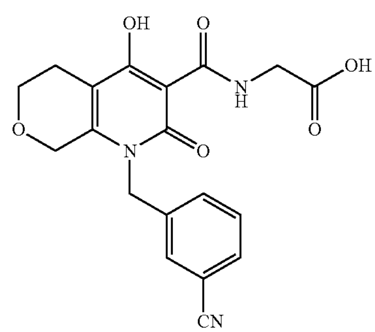 [SMILES: N#Cc1cccc(Cn2c3c(c(O)c(C(=O)NCC(=O)O)c2=O)CCOC3)c1] | (M + 1)+ 384<br>IC$_{50}$ 35.2 nM |
| Example 58 | 2-(1-(2-chlorobenzyl)-4-hydroxy-2-oxo-2,5,6,8-tetrahydro-1H-pyrano[3,4-b]pyridine-3-carboxamido)acetic acid | 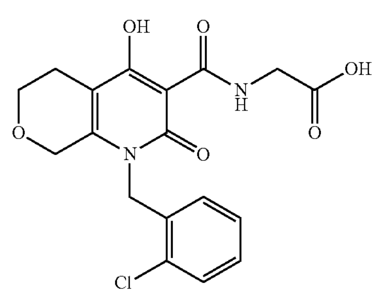 [SMILES: O=C(O)CNC(=O)c1c(O)c2c(n(Cc3ccccc3Cl)c1=O)COCC2] | (M + 1)+ 394<br>IC$_{50}$ 25.5 nM |

TABLE 2-continued

| Examples | Name | Structure | MS m/z (M + 1)+ and human HIF-PHD2 IC$_{50}$ |
|---|---|---|---|
| Example 59 | 2-(4-hydroxy-2-oxo-1-(pyridin-2-ylmethyl)-2,5,6,8-tetrahydro-1H-pyrano[3,4-b]pyridine-3-carboxamido)acetic acid | 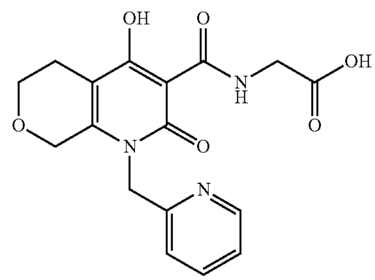 [SMILES: O=C(O)CNC(=O)c1c(O)c2c(n(Cc3ccccn3)c1=O)COCC2] | (M + 1)+ 360 IC$_{50}$ 44.2 nM |
| Example 60 | 2-(4-hydroxy-2-oxo-1-(pyridin-4-ylmethyl)-2,5,6,8-tetrahydro-1H-pyrano[3,4-b]pyridine-3-carboxamido)acetic acid | 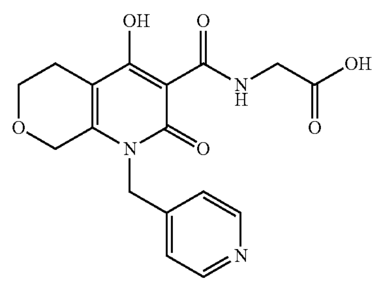 [SMILES: O=C(O)CNC(=O)c1c(O)c2c(n(Cc3ccncc3)c1=O)COCC2] | (M + 1)+ 360 IC$_{50}$ 30.4 nM |
| Example 61 | 2-(1-(4-cyano-3-fluorobenzyl)-4-hydroxy-2-oxo-2,5,6,8-tetrahydro-1H-pyrano[3,4-b]pyridine-3-carboxamido)acetic acid | 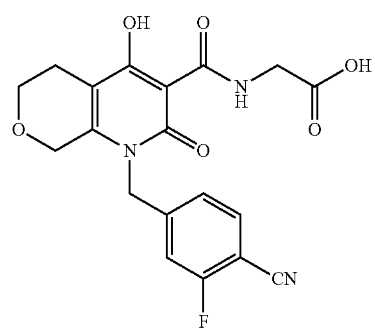 [SMILES: N#Cc1ccc(Cn2c3c(c(O)c(C(=O)NCC(=O)O)c2=O)CCOC3)cc1F] | (M + 1)+ 402 IC$_{50}$ 22.6 nM |
| Example 62 | 2-(4-hydroxy-2-oxo-1-(thiazol-5-ylmethyl)-2,5,6,8-tetrahydro-1H-pyrano[3,4-b]pyridine-3-carboxamido)acetic acid | 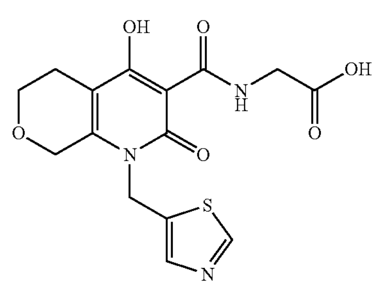 [SMILES: O=C(O)CNC(=O)c1c(O)c2c(n(Cc3cncs3)c1=O)COCC2] | (M + 1)+ 366 IC$_{50}$ 44.1 nM |

Example 63

2-(4-Hydroxy-1-(4-(2-hydroxypropan-2-yl)benzyl)-2-oxo-2,5,6,8-tetrahydro-1H-pyrano[3,4-b]pyridine-3-carboxamido)acetic acid

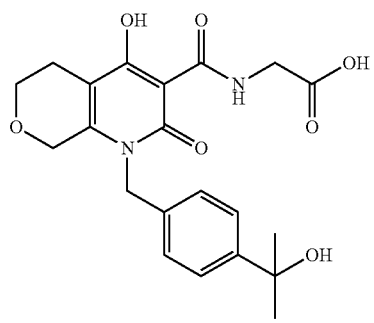 [SMILES: CC(C)(O)c1ccc(Cn2c3c(c(O)c(C(=O)NCC(=O)O)c2=O)CCOC3)cc1]

Step A: tert-Butyl 2-(4-hydroxy-1-(4-(2-hydroxypropan-2-yl)benzyl)-2-oxo-2,5,6,8-tetrahydro-1H-pyrano[3,4-b]pyridine-3-carboxamido)acetate By using Intermediate 2 similar procedures of Step A of Example 33, tert-butyl 2-(4-hydroxy-1-(4-(2-hydroxypropan-2-yl)benzyl)-2-oxo-2,5,6,8-tetrahydro-1H-pyrano[3,4-b]pyridine-3-carboxamido)acetate was synthesized as a solid. $^1$H NMR (CDCl$_3$, 400 MHz) δ: 15.89 (s, 1H), 10.57 (t, J=5.1 Hz, 1H), 7.40 (d, J=7.8 Hz, 2H), 7.05 (d, J=8.0 Hz, 2H), 5.19-5.01 (m, 2H), 4.48 (s, 2H), 4.11-4.01 (m, 2H), 3.87-3.76 (m, 2H), 2.58 (t, J=5.1 Hz, 2H), 1.52 (d, J=1.0 Hz, 6H), 1.46 (s, 9H).

Step B: 2-(4-Hydroxy-1-(4-(2-hydroxypropan-2-yl)benzyl)-2-oxo-2,5,6,8-tetrahydro-1H-pyrano[3,4-b]pyridine-3-carboxamido)acetic acid To a solution of tert-butyl 2-(4-hydroxy-1-(4-(2-hydroxypropan-2-yl)benzyl)-2-oxo-2,5,6,8-tetrahydro-1H-pyrano[3,4-b]pyridine-3-carboxamido)acetate (90 mg, 0.190 mmol) in THF (2 ml) was added aq. NaOH (0.762 ml, 2.5M, 1.905 mmol). After addition, the mixture was stirred at 40° C. overnight. LCMS showed the reaction was complete. The reaction mixture was extracted with EtOAc (1 mL). The aqueous layer was acidified with 1N HCl to pH=3-4 and then extracted with EtOAc (1 mL×3). The combined organic layers were dried and concentrated to give 2-(4-hydroxy-1-(4-(2-hydroxypropan-2-yl)benzyl)-2-oxo-2,5,6,8-tetrahydro-1H-pyrano[3,4-b]pyridine-3-carboxamido)acetic acid as a solid. $^1$H NMR (DMSO-d$_6$, 400 MHz) δ: 10.41-10.35 (m, 1H), 7.40 (d, J=8.2 Hz, 2H), 7.03 (d, J=8.2 Hz, 2H), 5.09 (br. s., 2H), 4.96 (s, 1H), 4.52 (br. s., 2H), 4.04 (d, J=5.3 Hz, 2H), 3.77 (t, J=5.4 Hz, 2H), 2.65 (t, J=5.4 Hz, 2H), 1.36 (s, 6H). LC/MS (m/z): 417 (M+H)$^+$. Human HIF-PHD2 IC$_{50}$: 67.4 nM.

Example 64

2-(1-(4-Carbamoylbenzyl)-4-hydroxy-2-oxo-2,5,6,8-tetrahydro-1H-pyrano[3,4-b]pyridine-3-carboxamido)acetic acid

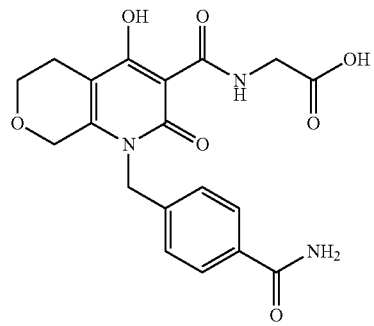 [SMILES: NC(=O)c1ccc(Cn2c3c(c(O)c(C(=O)NCC(=O)O)c2=O)CCOC3)cc1]

Using Intermediate 2 and similar procedures described for Example 34, the title compound was obtained as a solid. $^1$H NMR (DMSO-d$_6$, 400 MHz) δ: 10.36 (brs, 1H), 7.93 (brs, 1H), 7.83 (d, J=8.03 Hz, 1H), 7.34 (brs, 1H), 7.19 (d, J=8.53 Hz, 1H), 5.20 (brs, 2H), 4.52 (brs, 2H), 3.97 (brs, 2H), 3.79 (t, J=5.52 Hz, 2H), 2.50 (brs, 2H). LC/MS (m/z): 402 (M+H)$^+$. Human HIF-PHD2 IC$_{50}$: 30.6 nM.

Example 65

2-(4-Hydroxy-2-oxo-1-((4'-(trifluoromethyl)-[1,1'-biphenyl]-4-yl)methyl)-2,5,6,8-tetrahydro-1H-pyrano[3,4-b]pyridine-3-carboxamido)acetic acid

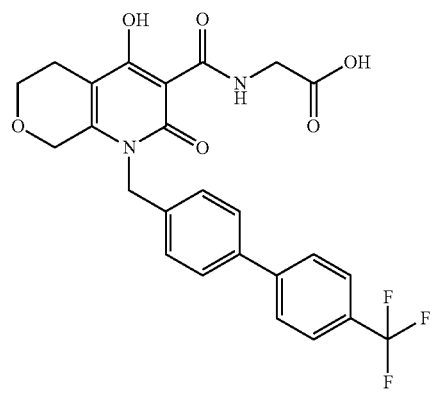 [SMILES: O=C(O)CNC(=O)c1c(O)c2c(n(Cc3ccc(-c4ccc(C(F)(F)F)cc4)cc3)c1=O)COCC2]

Step A: tert-Butyl-2-(4-hydroxy-2-oxo-1-((4'-(trifluoromethyl)-[1,1'-biphenyl]-4-yl)methyl)-2,5,6,8-tetrahydro-1H-pyrano[3,4-b]pyridine-3-carboxamido)acetate To a solution of Intermediate 3 (50 mg, 0.101 mmol) and (4-(trifluoromethyl)phenyl)boronic acid (38.5 mg, 0.203 mmol) in DMF (2 mL) were added K$_2$CO$_3$ (64.5 mg, 0.304 mmol) and PdCl$_2$(dppf) (7.43 mg, 10.13 μmol). After addition, the reaction mixture was heated to 110° C. by microwave and stirred at this temperature for 30 minutes when TLC (petroleum ether:EtOAc=2:1) showed that the reaction was complete. The reaction mixture was diluted with EtOAc (20 mL), washed with H$_2$O (20 mL×2) and brine (20 mL), dried over Na$_2$SO$_4$, filtered and concentrated in vacuo. The residue was purified by prep-TLC (petroleum ether:EtOAc=2:1) to afford tert-butyl 2-(4-hydroxy-2-oxo-1-((4'-(trifluoromethyl)-[1,1'-biphenyl]-4-yl)methyl)-2,5,6,8-tetrahydro-1H-pyrano[3,4-b]pyridine-3-carboxamido)acetate as a solid. LC/MS (m/z): 559 (M+H)$^+$.

Step B: 2-(4-Hydroxy-2-oxo-1-((4'-(trifluoromethyl)-[1,1'-biphenyl]-4-yl)methyl)-2,5,6,8-tetrahydro-1H-pyrano[3,4-b]pyridine-3-carboxamido) acetic acid To a solution of tert-butyl 2-(4-hydroxy-2-oxo-1-((4'-(trifluoromethyl)-[1,1'-biphenyl]-4-yl)methyl)-2,5,6,8-tetrahydro-1H-pyrano[3,4-b]pyridine-3-carboxamido)acetate (13 mg, 0.018 mmol) in DCM (1.5 mL) was added TFA (0.014 mL, 0.185 mmol). The reaction was stirred at room temperature for 4 hours. LC-MS showed that the reaction was completed. The reaction mixture was concentrated in vacuo to give the crude product, which was purified by prep-HPLC (Column: Grace 150*23.5*10 um; Mobile phase: From 50% MeCN in water(0.225% FA) to 80% MeCN in water(0.225% FA); Wavelength: 220 nm) to afford 2-(4-hydroxy-2-oxo-1-((4'-(trifluoromethyl)-[1,1'-biphenyl]-4-yl)methyl)-2,5,6,8-tetrahydro-1H-pyrano[3,4-b]pyridine-3-carboxamido)acetic acid as a solid. $^1$H NMR (DMSO-d$_6$, 400 MHz) δ: 10.40 (t, J=5.4 Hz, 1H), 7.87 (d, J=8.4 Hz, 2H), 7.81 (d, J=8.4 Hz, 2H), 7.72 (d, J=8.0 Hz, 2H), 7.27 (d, J=8.0 Hz, 2H), 5.22 (s, 2H), 4.58 (s, 2H), 4.08 (d, J=5.6 Hz, 2H), 3.81 (t, J=5.4 Hz, 2H), 2.54 (t, J=5.4 Hz, 2H). LC/MS (m/z): 503 (M+H)$^+$. Human HIF-PHD2 IC$_{50}$: 23.6 nM.

Examples 66-69 in Table 3 were prepared following the similar procedures described in Example 65 and using Intermediate 3 and the appropriate starting materials.

TABLE 3

| Examples | Name | Structure | MS m/z (M + 1)$^+$ and human HIF-PHD2 IC$_{50}$ |
|---|---|---|---|
| Example 66 | 2-(4-hydroxy-2-oxo-1-((4'-(trifluoromethoxy)-[1,1'-biphenyl]-4-yl)methyl)-2,5,6,8-tetrahydro-1H-pyrano[3,4-b]pyridine-3-carboxamido)acetic acid | 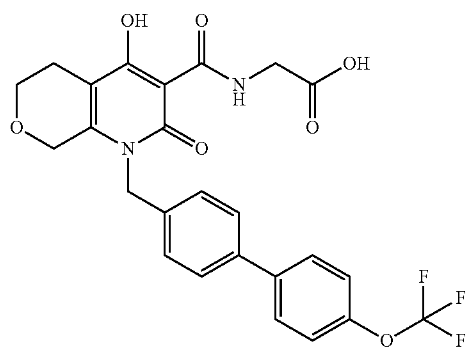 [SMILES: O=C(O)CNC(=O)c1c(O)c2c(n(Cc3ccc(-c4ccc(OC(F)(F)F)cc4)cc3)c1=O)COCC2] | (M + 1)$^+$ 519 IC$_{50}$ 28.8 nM |
| Example 67 | 2-(1-((4'-chloro-[1,1'-biphenyl]-4-yl)methyl)-4-hydroxy-2-oxo-2,5,6,8-tetrahydro-1H-pyrano[3,4-b]pyridine-3-carboxamido)acetic acid | 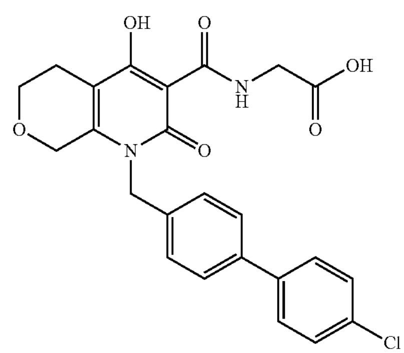 [SMILES: O=C(O)CNC(=O)c1c(O)c2c(n(Cc3ccc(-c4ccc(Cl)cc4)cc3)c1=O)COCC2] | (M + 1)$^+$ 394 IC$_{50}$ 13.5 nM |
| Example 68 | 2-(1-((4'-carbamoyl-[1,1'-biphenyl]-4-yl)methyl)-4-hydroxy-2-oxo-2,5,6,8-tetrahydro-1H-pyrano[3,4-b]pyridine-3-carboxamido)acetic acid | 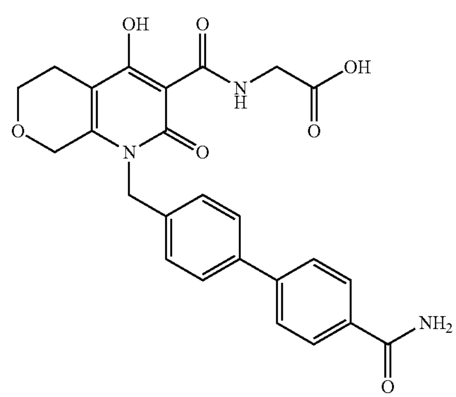 [SMILES: NC(=O)c1ccc(-c2ccc(Cn3c4c(c(O)c(C(=O)NCC(=O)O)c3=O)CCOC4)cc2)cc1] | (M + 1)$^+$ 478 IC$_{50}$ 7.8 nM |

TABLE 3-continued

| Examples | Name | Structure | MS m/z (M + 1)+ and human HIF-PHD2 IC$_{50}$ |
|---|---|---|---|
| Example 69 | 2-(1-((4'-cyano-[1,1'-biphenyl]-4-yl)methyl)-4-hydroxy-2-oxo-2,5,6,8-tetrahydro-1H-pyrano[3,4-b]pyridine-3-carboxamido)acetic acid | 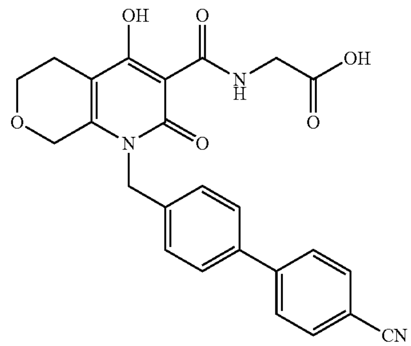 [SMILES: N#Cc1ccc(-c2ccc(Cn3c4c(c(O)c(C(=O)NCC(=O)O)c3=O)CCOC4)cc2)cc1] | (M + 1)+ 460 IC$_{50}$ 16.3 nM |

Example 70

2-(1-(4-Cyano-2-fluorobenzyl)-4-hydroxy-7-methyl-2,6-dioxo-1,2,5,6,7,8-hexahydro-1,7-naphthyridine-3-carboxamido)acetic acid

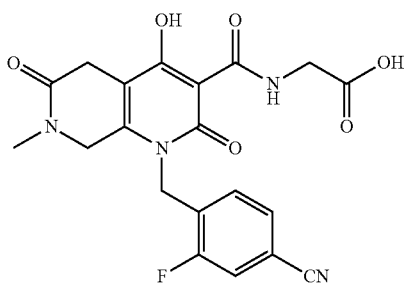

Step A: tert-Butyl 2-(1-(4-cyano-2-fluorobenzyl)-4-hydroxy-7-methyl-2,6-dioxo-1,2,5,6,7,8-hexahydro-1,7-naphthyridine-3-carboxamido)acetate To a solution of Intermediate 4 (20 mg, 0.057 mmol) and 4-(bromomethyl)-3-fluorobenzonitrile (24.37 mg, 0.114 mmol) in acetone (1 mL) and DMF (0.5 mL) was added K$_2$CO$_3$ (11.80 mg, 0.085 mmol). After addition, the mixture was stirred at 50° C. over weekend. LCMS showed the reaction was completed. Water (30 mL) was added and the reaction mixture was extracted with EtOAc (10 mL×3). The combined organic layers were dried and concentrated to give tert-butyl 2-(1-(4-cyano-2-fluorobenzyl)-4-hydroxy-7-methyl-2,6-dioxo-1,2,5,6,7,8-hexahydro-1,7-naphthyridine-3-carboxamido)acetate as an oil which was used directly in the next step. LC/MS (m/z): 485 (M+H)+.

Step B: 2-(1-(4-Cyano-2-fluorobenzyl)-4-hydroxy-7-methyl-2,6-dioxo-1,2,5,6,7,8-hexahydro-1,7-naphthyridine-3-carboxamido)acetic acid To a solution of tert-butyl 2-(1-(4-cyano-2-fluorobenzyl)-4-hydroxy-7-methyl-2,6-dioxo-1,2,5,6,7,8-hexahydro-1,7-naphthyridine-3-carboxamido)acetate (20 mg, 0.033 mmol) in DCM (5 ml) was added 2,2,2-trifluoroacetic acid (37.7 mg, 0.330 mmol). The resulting mixture was stirred at room temperature for 3 hours. LCMS showed that the reaction was completed. The resulting mixture was concentrated in vacuo. The residue was purified by HPLC (Column: Gemini C18 150*23.5 mm*10 um; Mobile phase: From 10% MeCN in water (0.225% FA) to 40% MeCN in water (0.225% FA); Wavelength: 220 nm) to give 2-(1-(4-cyano-2-fluorobenzyl)-4-hydroxy-7-methyl-2,6-dioxo-1,2,5,6,7,8-hexahydro-1,7-naphthyridine-3-carboxamido)acetic acid as a solid. $^1$H NMR (DMSO-d$_6$, 400 MHz): δ 10.14 (brs, 1H), 7.92 (d, J=10.3 Hz, 1H), 7.63 (d, J=6.8 Hz, 1H), 7.13 (t, J=8.0 Hz, 1H), 5.28 (s, 2H), 4.71 (s, 2H), 4.01 (d, J=5.2 Hz, 2H), 3.24 (s, 2H), 2.89 (s, 3H). LC/MS (m/z): 429 (M+H)+. Human HIF-PHD2 IC$_{50}$: 10.4 nM.

Examples 71-76 in Table 4 were prepared following the similar procedures described in Example 70 and using Intermediate 4 and the appropriate starting materials.

TABLE 4

| Examples | Name | Structure | MS m/z (M + 1)+ and human HIF-PHD2 IC$_{50}$ |
|---|---|---|---|
| Example 71 | 2-(4-hydroxy-7-methyl-1-(4-(methylsulfonyl)benzyl)-2,6-dioxo-1,2,5,6,7,8-hexahydro-1,7-naphthyridine-3-carboxamido)acetic acid | 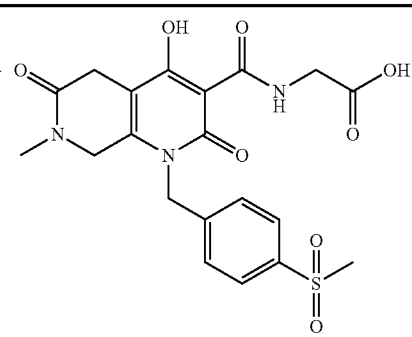 | (M + 1)+ 464 IC$_{50}$ 19.0 nM |

TABLE 4-continued

| Examples | Name | Structure | MS m/z (M + 1)+ and human HIF-PHD2 IC$_{50}$ |
|---|---|---|---|
| Example 72 | 2-(1-(2,4-difluorobenzyl)-4-hydroxy-7-methyl-2,6-dioxo-1,2,5,6,7,8-hexahydro-1,7-naphthyridine-3-carboxamido)acetic acid | 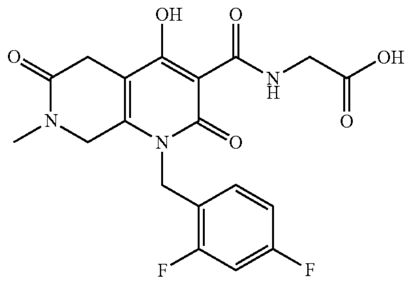 [SMILES: CN1Cc2c(c(O)c(C(=O)NCC(=O)O)c(=O)n2Cc2ccc(F)cc2F)CC1=O] | (M + 1)+ 422 IC$_{50}$ 28.7 nM |
| Example 73 | 2-(1-(3-cyanobenzyl)-4-hydroxy-7-methyl-2,6-dioxo-1,2,5,6,7,8-hexahydro-1,7-naphthyridine-3-carboxamido)acetic acid | 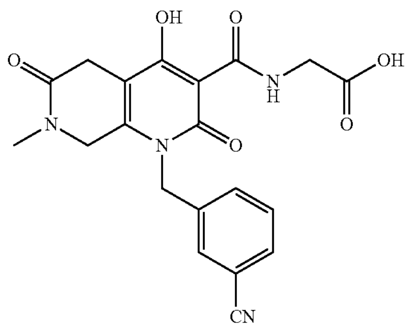 [SMILES: CN1Cc2c(c(O)c(C(=O)NCC(=O)O)c(=O)n2Cc2cccc(C#N)c2)CC1=O] | (M + 1)+ 411 IC$_{50}$ 17.2 nM |
| Example 74 | 2-(1-(4-cyanobenzyl)-4-hydroxy-7-methyl-2,6-dioxo-1,2,5,6,7,8-hexahydro-1,7-naphthyridine-3-carboxamido)acetic acid | 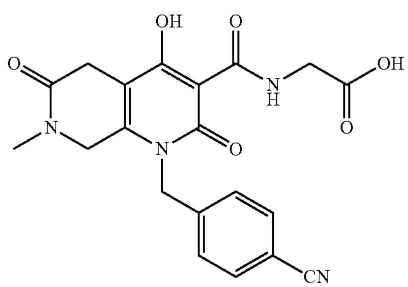 [SMILES: CN1Cc2c(c(O)c(C(=O)NCC(=O)O)c(=O)n2Cc2ccc(C#N)cc2)CC1=O] | (M + 1)+ 411 IC$_{50}$ 7.5 nM |
| Example 75 | 2-(1-(4-chlorobenzyl)-4-hydroxy-7-methyl-2,6-dioxo-1,2,5,6,7,8-hexahydro-1,7-naphthyridine-3-carboxamido)acetic acid | 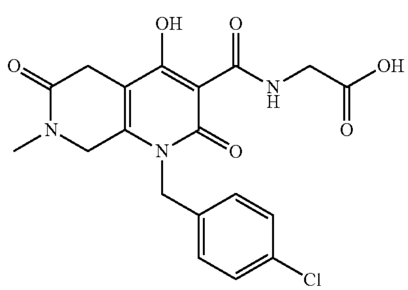 [SMILES: CN1Cc2c(c(O)c(C(=O)NCC(=O)O)c(=O)n2Cc2ccc(Cl)cc2)CC1=O] | (M + 1)+ 420 IC$_{50}$ 7.3 nM |
| Example 76 | 2-(1-(2-chlorobenzyl)-4-hydroxy-7-methyl-2,6-dioxo-1,2,5,6,7,8-hexahydro-1,7-naphthyridine-3-carboxamido)acetic acid | 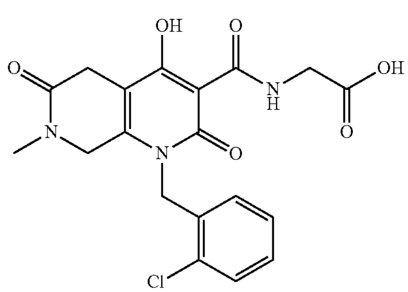 [SMILES: CN1Cc2c(c(O)c(C(=O)NCC(=O)O)c(=O)n2Cc2ccccc2Cl)CC1=O] | (M + 1)+ 420 IC$_{50}$ 10.6 nM |

Example 77

2-(4-Hydroxy-2-oxo-1-(4-(trifluoromethyl)benzyl)-1,2,5,6,7,8-hexahydroquinoline-3-carboxamido)acetic acid

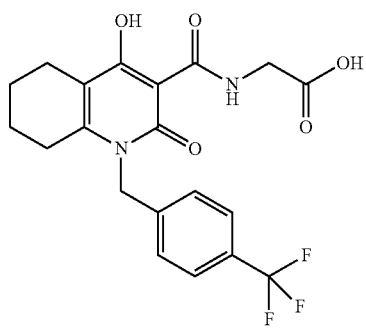 [SMILES: O=C(O)CNC(=O)c1c(O)c2c(n(Cc3ccc(C(F)(F)F)cc3)c1=O)CCCC2]

Step A: Ethyl 2-((4-(trifluoromethyl)benzyl)amino)cyclohex-1-enecarboxylate

To ethyl 2-oxocyclohexanecarboxylate (0.750 g, 4.41 mmol) in toluene (5 mL) was added (4-(trifluoromethyl)phenyl)methanamine (0.77 g, 4.41 mmol) and 4-methylbenzenesulfonic acid hydrate (8.4 mg, 0.044 mmol). A Dean-Stark trap was applied, filled with toluene, and the reaction was refluxed for 2 hr until all water was removed from reaction. The solution was cooled, concentrated and the residue was purified by flash chromatography on silica gel gradient eluted with 0-10% EtOAc in hexane to afford the title compound. Parent mass was not observed by LC/MS.

Step B: Ethyl 2-(3-methoxy-3-oxo-N-(4-(trifluoromethyl)benzyl)propanamido)cyclohex-1-enecarboxylate To the product of Step A (0.510 g, 1.62 mmol) in DMF (2 mL) was added methyl 3-chloro-3-oxopropanoate (0.594 g, 4.35 mmol). The mixture was stirred for 1 hr at 50° C. and was allowed to cool. The reaction was diluted with EtOAc, washed with brine, dried ($Na_2SO_4$), filtered and concentrated. The residue was purified by flash chromatography on silica gel gradient eluted with 0-50% EtOAc in hexane to afford the title compound. LC/MS (m/z): 428 (M+H)$^+$.

Step C: Methyl 4-hydroxy-2-oxo-1-(4-(trifluoromethyl)benzyl)-1,2,5,6,7,8-hexahydroquinoline-3-carboxylate To the product of Step B (0.700 g, 1.64 mol) in MeOH (5 mL) was added sodium methoxide (0.448 mL, 1.638 mmol, 25 wt %) at rt. After 15 min additional sodium methoxide (0.200 mL, 0.731 mmol, 25 wt %) was added and the reaction was stirred for 15 mins then quenched with acetic acid (0.094 mL, 1.64 mmol). The solution was concentrated and diluted with EtOAc and washed with aq HCl (2M) and water. The organic layer was dried ($Na_2SO_4$), filtered and concentrated. The residue was purified by flash chromatography on silica gel gradient eluted with 0-50% EtOAc in hexane to afford the title compound. LC/MS (m/z): 382 (M+H)$^+$.

Step D: tert-butyl 2-(4-hydroxy-2-oxo-1-(4-(trifluoromethyl)benzyl)-1,2,5,6,7,8-hexahydroquinoline-3-carboxamido)acetate The product of Step C (0.325 g, 0.852 mmol) was dissolved in 1-propanol (2 mL) in a 10 mL reaction tube of a CEM Corporation Discover 300 Watt microwave reactor. tert-Butyl glycinate (0.224 g, 1.70 mmol) was added and the tube was purged with nitrogen, capped and inserted into the microwave reactor. It was heated at 140° C., 50 watts maximum power, for 15 min. The mixture was concentrated and the product was redissolved with EtOAc, washed with acidic brine, dried ($Na_2SO_4$), filtered and concentrated. The residue was purified by flash chromatography on silica gel gradient eluted with 0-40% EtOAc in hexane to afford the title compound. Parent mass was not observed by LC/MS.

Step E: 2-(4-Hydroxy-2-oxo-1-(4-(trifluoromethyl)benzyl)-1,2,5,6,7,8-hexahydroquinoline-3-carboxamido)acetic acid To the product of Step D (0.325 g, 0.676 mmol) was added $CH_2Cl_2$ (3 mL) and TFA (1 mL) at rt. After 2 hr the reaction was concentrated and then diluted with ether. The crystals were isolated by filtration and washed twice with hexane to afford the title compound. LC/MS (m/z): 425 (M+H)$^+$. Human HIF-PHD2 $IC_{50}$: 66 nM.

Example 78

2-(4-Hydroxy-2-oxo-1-(4-(trifluoromethyl)benzyl)-1,2,5,6,7,8-hexahydro-1,8-naphthyridine-3-carboxamido)acetic acid

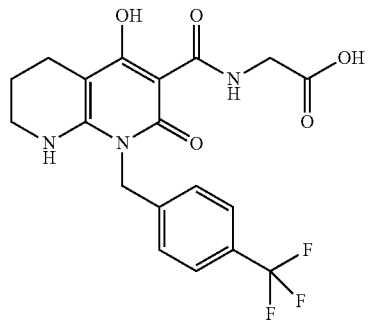 [SMILES: O=C(O)CNC(=O)c1c(O)c2c(n(Cc3ccc(C(F)(F)F)cc3)c1=O)NCCC2]

A solution of 2-(4-hydroxy-2-oxo-1-(4-(trifluoromethyl)benzyl)-1,2-dihydro-1,8-naphthyridine-3-carboxamido)acetic acid (PCT Int. Appl., 2008130527; 300 mg, 0.712 mmol) in acetic acid (30.0 ml) was passed through the H-Cube at 80° C. and 100 bar continuously (recycling) for 1.5 h. The acetic acid was then evaporated under reduced pressure to afford 290 mg of the title compound. $^1$H NMR (500 MHz, $(CD_3)_2SO$) δ 12.6 (b, 1H), 10.07 (dd, J=5.5, Hz, 1H), 7.69 (d, J=8.3 Hz, 2H), 7.36 (s, 1H), 7.317 (d, J=8.0 Hz, 2H), 5.28 (b, 2H), 3.97 (d, J=5.5 Hz, 2H), 3.32 (b, 1H), 3.23 (b, 2H) 2.44 (dd, J=6.2 Hz, 2H), 1.71 (m, 2H). LC/MS (m/z): 426 (M+H)$^+$. Human HIF-PHD2 $IC_{50}$: 70 nM.

Example 79

2-(4-Hydroxy-2-oxo-1-(4-(trifluoromethyl)benzyl)-1,2,5,6,7,8-hexahydro-1,6-naphthyridine-3-carboxamido)acetic acid

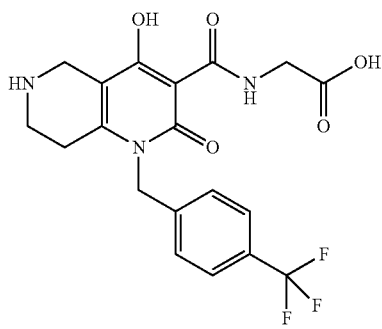 [SMILES: O=C(O)CNC(=O)c1c(O)c2c(n(Cc3ccc(C(F)(F)F)cc3)c1=O)CCNC2]

Step A: 1-tert-Butyl 3-ethyl 4-((4-(trifluoromethyl)benzyl)amino)-5,6-dihydropyridine-1,3(2H)-dicarboxylate To 1-tert-butyl 3-ethyl 4-oxopiperidine-1,3-dicarboxylate (2 g, 7.37 mmol) in EtOH (20 ml) was added (4-(trifluoromethyl)phenyl)methanamine (1.291 g, 7.37 mmol), followed by acetic acid (0.127 ml, 2.211 mmol)). The mixture was refluxed for 2 h then was concentrated in vacuo and taken up in EtOAc and water. The organic layer was washed with aqueous NaHCO$_3$. The aqueous layer was extracted with EtOAc and the combined organic extracts were washed with water and brine, dried over Na$_2$SO$_4$ and concentrated in vacuo. The crude was triturated with EtOAc and filtered to give the pure product. This step was repeated with the 1st mother liquor after it was concentrated under reduced pressure to obtain more desired product 1-tert-butyl 3-ethyl 4-((4-(trifluoromethyl)benzyl)amino)-5,6-dihydropyridine-1,3(2H)-dicarboxylate. LC/MS (m/z): 429 (M+H)$^+$.

Step B: 1-tert-butyl 3-ethyl 4-(3-ethoxy-3-oxo-N-(4-(trifluoromethyl)benzyl)propanamido)-5,6-dihydropyridine-1,3(2H)-dicarboxylate To Step A product (800 mg, 1.867 mmol) in toluene (20 ml) was added N-ethyl-N-isopropylpropan-2-amine (603 mg, 4.67 mmol) slowly, followed by ethyl 3-chloro-3-oxopropanoate (422 mg, 2.80 mmol)). The mixture was refluxed for 2 h. Then the mixture was concentrated in vacuo and taken up in EtOAc and water. The organic layer was then washed with aqueous NaHCO$_3$ and brine, dried and concentrated. Purification by silica column afforded 1-tert-butyl 3-ethyl 4-(3-ethoxy-3-oxo-N-(4-(trifluoromethyl)benzyl)propanamido)-5,6-dihydropyridine-1,3(2H)-dicarboxylate. LC/MS (m/z): 543 (M+H)$^+$.

Step C: 6-tert-Butyl 3-ethyl 4-hydroxy-2-oxo-1-(4-(trifluoromethyl)benzyl)-1,2,7,8-tetrahydro-1,6-naphthyridine-3,6(5H)-dicarboxylate To NaOEt (448 mg, 1.382 mmol) in ethanol (25 ml) was added Step B product (500 mg, 0.922 mmol) and a yellow ppt formed immediately. The reaction was heated in a sealed vial at 85° C. for 4 h. The reaction mixture was concentrated in vacuo and quenched with sat. aq. NaH$_2$PO$_4$. EtOAc was added and the layers were separated. The aqueous layer was extracted with EtOAc. The combined organic extracts were washed with water and brine, dried over MgSO$_4$ and concentrated in vacuo. The residue was purified by column chromatography on silica gel eluting with EtOAc/isohexane (10 to 60%) to give 6-tert-butyl 3-ethyl 4-hydroxy-2-oxo-1-(4-(trifluoromethyl)benzyl)-1,2,7,8-tetrahydro-1,6-naphthyridine-3,6(5H)-dicarboxylate.

Step D: 2-(4-Hydroxy-2-oxo-1-(4-(trifluoromethyl)benzyl)-1,2,5,6,7,8-hexahydro-1,6-naphthyridine-3-carboxamido)acetic acid To Step C product (50 mg, 0.101 mmol) in Toluene (0.7 ml) was added tert-butyl 2-aminoacetate (13.21 mg, 0.101 mmol). The reaction was heated in a sealed vial at 120° C. overnight. After cooled down to rt, toluene was evaporated. To the residue were added 0.5 mL of DCM and 0.5 mL of TFA. The reaction was stirred at 50° C. for 3 hrs. Upon concentration, the residue was purified by preparative HPLC Reverse phase (C-18), eluting with Acetonitrile/Water+0.1% TFA, to give 2-(4-Hydroxy-2-oxo-1-(4-(trifluoromethyl)benzyl)-1,2,5,6,7,8-hexahydro-1,6-naphthyridine-3-carboxamido)acetic acid LC/MS (m/z): 426 (M+H)$^+$. Human HIF-PHD2 IC$_{50}$: 22.9 nM.

Example 80 in Table 5 was prepared following the similar procedure described in Example 79 using starting material ethyl 1-benzyl-3-oxopiperidine-4-carboxylate in Step A.

TABLE 5

| Example Name | Structure | MS m/z (M + 1)$^+$ and human HIF-PHD2 IC$_{50}$ |
|---|---|---|
| Example 80 | 2-(7-Benzyl-4-hydroxy-2-oxo-1-(4-(trifluoromethyl)benzyl)-1,2,5,6,7,8-hexahydro-1,7-naphthyridine-3-carboxamido)acetic acid | (M + 1)$^+$ 516 IC$_{50}$ 32 nM |

Example 81

2-(4-Hydroxy-6-methyl-2-oxo-1-(4-(trifluoromethyl)benzyl)-1,2,5,6,7,8-hexahydro-1,6-naphthyridine-3-carboxamido)acetic acid

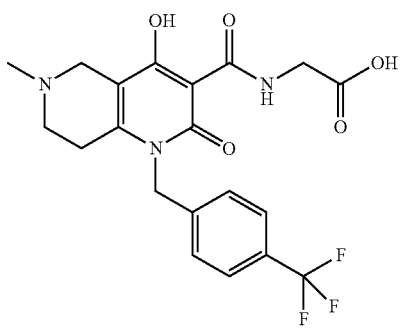 [SMILES: CN1CCc2c(c(O)c(C(=O)NCC(=O)O)c(=O)n2Cc2ccc(C(F)(F)F)cc2)C1]

Step A: Ethyl 4-hydroxy-6-methyl-2-oxo-1-(4-(trifluoromethyl)benzyl)-1,2,5,6,7,8-hexahydro-1,6-naphthyridine-3-carboxylate To 6-tert-butyl 3-ethyl 4-hydroxy-2-oxo-1-(4-(trifluoromethyl)benzyl)-1,2,7,8-tetrahydro-1,6-naphthyridine-3,6 (5H)-dicarboxylate (Example 79 Step C product; 50 mg, 0.101 mmol) in 0.5 mL of DCM was added TFA (0.5 mL). The reaction was stirred at rt for 4 hr. After volatiles were removed, to the residue were added DCM (1 ml), formaldehyde (15.12 mg, 0.201 mmol), 1 drop of acetic acid and sodium triacetoxyborohydride (21.3 mg, 0.101 mmol). The reaction was stirred at rt overnight and then concentrated. The residue was partitioned between EtOAc and sat. aq NaHSO$_4$ solution. The aqueous layer was extracted with EtOAc. The combined organic extracts were washed with water and brine, dried over MgSO$_4$ and concentrated in vacuo. The crude was purified by silica column chromatography eluting with EtOAc/isohexane (10 to 80%) to give ethyl 4-hydroxy-6-methyl-2-oxo-1-(4-(trifluoromethyl)benzyl)-1,2,5,6,7,8-hexahydro-1,6-naphthyridine-3-carboxylate. LC/MS (m/z): 411 (M+H)$^+$.

Step B: 2-(4-Hydroxy-6-methyl-2-oxo-1-(4-(trifluoromethyl)benzyl)-1,2,5,6,7,8-hexahydro-1,6-naphthyridine-3-carboxamido)acetic acid To Step A product (20 mg, 0.049 mmol) in toluene (0.7 ml) was added DIPEA (8.51 µl, 0.049 mmol) and $^t$buty-2-aminoacetate (6.39 mg, 0.049 mmol). The reaction was heated in a sealed vial at 120° C. overnight. After cooling to rt and evaporation of volatiles, to the residue were added 0.5 mL of DCM and 0.5 mL of TFA. The reaction was stirrted at 50° C. for 3 hrs. The mixture was concentrated and the residue was purified by preparative HPLC Reverse phase (C-18), eluting with Acetonitrile/Water+0.1% TFA, to give 2-(4-hydroxy-6-methyl-2-oxo-1-(4-(trifluoromethyl)benzyl)-1,2,5,6,7,8-hexahydro-1,6-naphthyridine-3-carboxamido)acetic acid. $^1$HNMR (DMSO-d$_6$, 500 MHz) δ 10.22 (s, 1H), 7.88 (d, 2H), 7.39 (d, 2H), 5.40 (broad s, 2H), 4.10 (s, 2H), 4.08 (broad s, 2H), 3.01 (broad s, 2H), 2.98 (s, 3H), 2.45 (s, 2H). LC/MS (m/z): 440 (M+H)$^+$. Human HIF-PHD2 IC$_{50}$: 46.1 nM.

Example 82

2-((5S,8R)-1-(benzo[d]thiazol-2-ylmethyl)-4-hydroxy-2-oxo-1,2,5,6,7,8-hexahydro-5,8-methanoquinoline-3-carboxamido)acetic acid

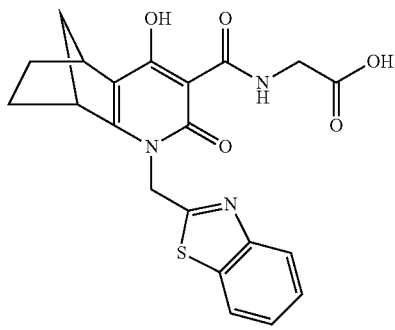 [SMILES: O=C(O)CNC(=O)c1c(O)c2c(n(Cc3nc4ccccc4s3)c1=O)C1CCC2C1]

Step A: Methyl 3-((benzo[d]thiazol-2-ylmethyl)amino)bicyclo[2.2.1]hept-2-ene-2-carboxylate To methyl 3-oxobicyclo[2.2.1]heptane-2-carboxylate (400 mg, 2.378 mmol) in ethanol (6 mL) were added benzo[d]thiazol-2-ylmethanamine HCl salt (501 mg, 2.497 mmol) and TEA (0.315 mL, 2.259 mmol) followed by acetic acid (0.041 mL, 0.713 mmol). The mixture was refluxed for 2 h. Upon completion by TLC, the mixture was concentrated in vacuo and taken up in EtOAc and water. The organic layer was washed with aq NaHCO$_3$. The aqueous layer was then extracted with EtOAc and the combined organic extracts were washed with water and brine, dried over Na$_2$SO$_4$ and concentrated in vacuo to give an oil which was taken up in the minimum amount of DCM and chromatographed on a 40S column with a 10, 20, 30%, ethyl acetate/hexanes gradient elution to give methyl 3-((benzo[d]thiazol-2-ylmethyl)amino)bicyclo[2.2.1]hept-2-ene-2-carboxylate as a solid. LC/MS (m/z): 315 (M+H)$^+$.

Step B: Methyl 3-(N-(benzo[d]thiazol-2-ylmethyl)-3-ethoxy-3-oxopropanamido)bicyclo[2.2.1]hept-2-ene-2-carboxylate To Step A product (520 mg, 1.654 mmol) in DCM (15 mL) at 0° C. was added pyridine (0.201 mL, 2.481 mmol). Ethyl 3-chloro-3-oxopropanoate (0.318 mL, 2.481 mmol) was then added dropwise followed by DMAP (40.4 mg, 0.331 mmol) and the mixture was then warmed to r.t. and then heated to 35° C. for 5 h. The reaction mixture was concentrated in vacuo and then taken up in EtOAc and water. The organic mixture was washed with 5% KHSO$_4$ and sat. NaHCO$_3$. The organic layer was dried over Na$_2$SO$_4$ and concentrated in vacuo to give an oil which was taken up in the minimum amount of DCM and chromatographed on a 40S column with a 10, 20, 30%, ethyl acetate/hexanes gradient elution to give 3 products, 2 of which were transesterification products and one was methyl 3-(N-(benzo[d]thiazol-2-ylmethyl)-3-ethoxy-3-oxopropanamido)bicyclo [2.2.1]hept-2-ene-2-carboxylate. All three were taken on to the next reaction together.

Step C: Ethyl 1-(benzo[d]thiazol-2-ylmethyl)-4-hydroxy-2-oxo-1,2,5,6,7,8-hexahydro-5,8-methanoquinoline-3-carboxylate To NaOEt (167 mg, 2.450 mmol) in ethanol (12 ml) was added Step B product (700 mg, 1.634 mmol). The reaction was heated in a sealed vial at 85° C. for 2 h. The reaction mixture was concentrated in vacuo and quenched with sat. aq NaH$_2$PO$_4$. EtOAc was added and the layers were separated. The aqueous layer was extracted with EtOAc. The combined organic extracts were washed with water and brine, dried over Na$_2$SO$_4$ and concentrated in vacuo to give an oil. The crude material was taken up in the minimum amount of DCM and chromatographed on a 40S column with a 10, 20, 30%, acetone/hexanes gradient elution to give ethyl 1-(benzo[d]thiazol-2-ylmethyl)-4-hydroxy-2-oxo-1,2,5,6,7,8-hexahydro-5,8-methanoquinoline-3-carboxylate as a solid.

Step D: tert-Butyl 2-(1-(benzo[d]thiazol-2-ylmethyl)-4-hydroxy-2-oxo-1,2,5,6,7,8-hexahydro-5,8-methanoquinoline-3-carboxamido)acetate To a solution of Step C product (50 mg, 0.126 mmol) in DME (1.0 mL) was added tert-butyl 2-aminoacetate (0.034 mL, 0.252 mmol). The reaction was heated in a microwave tube at 120° C. for 1 h. The mixture was concentrated in vacuo to give a brown oil which was taken up in the minimum amount of DCM and chromatographed on a 25S column with a 10, 20, 30%, ethyl acetate/hexanes gradient elution to give tert-butyl 2-(1-(benzo[d]thiazol-2-ylmethyl)-4-hydroxy-2-oxo-1,2,5,6,7,8-hexahydro-5,8-methanoquinoline-3-carboxamido) as an oil. LC/MS (m/z): 482 (M+H)$^+$.

Step E: 2-(1-(Benzo[d]thiazol-2-ylmethyl)-4-hydroxy-2-oxo-1,2,5,6,7,8-hexahydro-5,8-methanoquinoline-3-carboxamido)acetic acid The Step D product (40 mg, 0.083 mmol) was dissolved in DCM (1.0 mL) at rt and to it was added TFA (1.0 mL, 12.98 mmol). The reaction was stirred at room temperature for 3 h. The mixture was concentrated by vacuum. The residue was then azeotroped with dichloroethane to give a solid which was triturated with hexanes to give racemic 2-(1-(benzo[d]thiazol-2-ylmethyl)-4-hydroxy-2-oxo-1,2,5,6,7,8-hexahydro-5,8-methanoquinoline-3-carboxamido) acetic acid. $^1$HNMR (DMSO-d$_6$, 500 MHz) δ 12.80 (broad s, 1H), 10.21 (s, 1H), 8.05 (d, 1H), 7.98 (d, 1H), 7.52 (m, 1H), 7.43 (m, 1H), 5.73 (ab q, 2H), 4.02 (s, 2H), 1.85 (m, 2H), 1.68 (d, 1H), 1.43 (d, 1H), 1.23-1.05 (m, 4H). LC/MS (m/z): 426 (M+H)$^+$. Human HIF-PHD2 IC$_{50}$: 43 nM.

Examples 83-85 in Table 6 were prepared following the similar procedures described in Example 82 and using appropriate amine in Step A.

TABLE 6

| Examples | Name | Structure | MS m/z (M + 1)$^+$ and human HIF-PHD2 IC$_{50}$ |
|---|---|---|---|
| Example 83 | 2-(-4-hydroxy-2-oxo-1-(4-(trifluoromethyl)benzyl)-1,2,5,6,7,8-hexahydro-5,8-methanoquinoline-3-carboxamide)acetic acid | 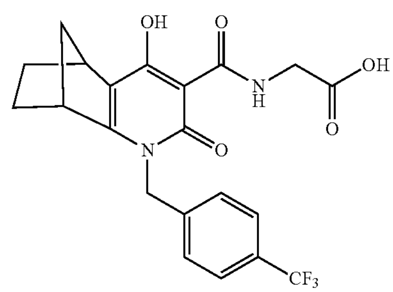 [SMILES: O=C(O)CNC(=O)c1c(O)c2c(n(Cc3ccc(C(F)(F)F)cc3)c1=O)C1CCC2C1] | (M + 1)$^+$ 437 IC$_{50}$ 46 nM |
| Example 84 | 2-(-4-hydroxy-2-oxo-1-((2-phenylthiazol-5-yl)methyl)-1,2,5,6,7,8-hexahydro-5,8-methanoquinoline-3-carboxamido)acetic acid | 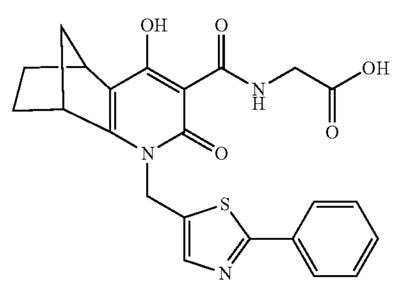 [SMILES: O=C(O)CNC(=O)c1c(O)c2c(n(Cc3cnc(-c4ccccc4)s3)c1=O)C1CCC2C1] | (M + 1)$^+$ 452 IC$_{50}$ 19 nM |
| Example 85 | 2-(-4-hydroxy-2-oxo-1-((4-phenylthiaozl-2-yl)methyl)-1,2,5,6,7,8-hexahydro-5,8-methanoquinoline-3-carboxamido)acetic acid | 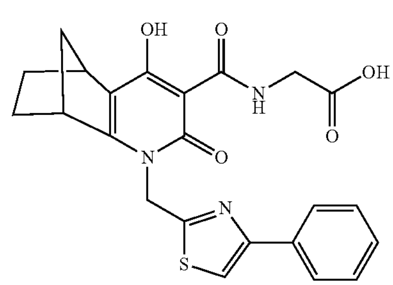 [SMILES: O=C(O)CNC(=O)c1c(O)c2c(n(Cc3nc(-c4ccccc4)cs3)c1=O)C1CCC2C1] | (M + 1)$^+$ 452 IC$_{50}$ 61 nM |

Biological Assays

The exemplified compounds of the present invention have been found to inhibit the hydroxylation of a HIF peptide by PHD2 and exhibit $IC_{50}$ values ranging between 0.1 nanomolar to 10 micromolar. Select examples of assays that may be used to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 275-280 (2005); and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below:

To each well of a 384-well plate, 1 μL of test compounds in DMSO (final concentration ranging from 0.3 nM to 10 uM) were added into 20 μl of assay buffer (50 mM Tris pH 7.4/0.01% Tween-20/0.1 mg/ml bovine serum albumin/10 μM ferrous sulfate/1 mM sodium ascorbate/20 μg/ml catalase) containing 0.15 μg/ml FLAG-tagged full length PHD2 expressed in and purified from baculovirus-infected Sf9 cells. After a 5 min preincubation at room temperature, the enzymatic reactions were initiated by the addition of 4 μL of substrates {final concentrations of 0.2 μM 2-oxoglutarate and 0.5 μM HIF-1α peptide biotinyl-DLDLEMLAPYIP-MDDDFQL (SEQ ID NO:1)}. After incubation for 45 minutes at room temperature, the reactions were terminated by the addition of a 25 μL quench/detection mix to a final concentration of 1 mM ortho-phenanthroline, 0.1 mM EDTA, 0.5 nM anti-(His)6 LANCE reagent (Perkin-Elmer Life Sciences), 100 nM AF647-labeled streptavidin (Invitrogen), and 2 μg/ml (His)6-VHL complex {S. Tan Protein Expr. Purif. 21, 224-234 (2001)} and the signals were developed for 30 minutes at room temperature. The ratio of time resolved fluorescence signals at 665 and 620 nm was determined, and percent inhibition was calculated relative to the high control samples (DMSO treated) run in parallel, after background substraction.

Inhibition of the catalytic activity of HIF-PHD1 and HIF-PHD3 can be determined similarly, except for HIF-PHD3, final concentrations of 4 μM 2-oxoglutarate is used during the reaction.

What is claimed is:

1. A compound of formula II or a pharmaceutically acceptable salt thereof:

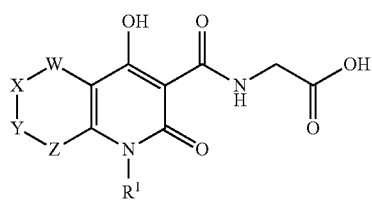

II wherein:
W is $CH_2$ or $NR^5$;
X is O, or $NR^5$;
Y is $CH_2$, O, (C=O), or $NR^5$;
Z is $CH_2$ or $NR^5$; wherein when W is $CH_2$ and Z is $CH_2$ then W and Z optionally combine with another carbon atom to form a bridge;
$R^1$ is selected from hydrogen, $C_{1-4}$ alkyl, $C_{3-8}$ cycloalkyl, aryl, heterocyclyl, Me-aryl, Me-heterocyclyl, Me-cycloalkyl, said cycloalkyl, aryl and heterocyclyl are optionally substituted with 1, 2, or 3 substituents chosen from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN;
$R^5$ is independently hydrogen, methyl or phenyl; and
$R^b$ is independently hydrogen or $C_{1-4}$ alkyl.

2. A compound which is:
2-(4-Hydroxy-2-oxo-1-(4-(trifluoromethyl)benzyl)-2,5,7,8-tetrahydro-1H-pyrano[4,3-b]pyridine-3-carboxamido)acetic acid;
2-(4-Hydroxy-2-oxo-1-(4-(trifluoromethyl)benzyl)-2,5,6,8-tetrahydro-1H-pyrano[3,4-b]pyridine-3-carboxamido)acetic acid;
2-(4-Hydroxy-7-methyl-2,6-dioxo-1-(4-(trifluoromethyl)benzyl)-1,2,5,6,7,8-hexahydro-1,7-naphthyridine-3-carboxamido)acetic acid;
2-(4-Hydroxy-2-oxo-2,5,7,8-tetrahydro-1H-pyrano[4,3-b]pyridine-3-carboxamido)acetic acid;
2-(1-(4-Cyanobenzyl)-4-hydroxy-2-oxo-2,5,7,8-tetrahydro-1H-pyrano[4,3-b]pyridine-3-carboxamido)acetic acid;
2-(4-hydroxy-1-(4-methoxybenzyl)-2-oxo-2,5,7,8-tetrahydro-1H-pyrano[4,3-b]pyridine-3-carboxamido)acetic acid;
2-(4-hydroxy-2-oxo-1-(4-(trifluoromethoxy)benzyl)-2,5,7,8-tetrahydro-1H-pyrano[4,3-b]pyridine-3-carboxamido)acetic acid;
2-(1-(4-(difluoromethoxy)benzyl)-4-hydroxy-2-oxo-2,5,7,8-tetrahydro-1H-pyrano[4,3-b]pyridine-3-carboxamido)acetic acid;
2-(1-(4-fluorobenzyl)-4-hydroxy-2-oxo-2,5,7,8-tetrahydro-1H-pyrano[4,3-b]pyridine-3-carboxamido)acetic acid;
2-(1-(4-chlorobenzyl)-4-hydroxy-2-oxo-2,5,7,8-tetrahydro-1H-pyrano[4,3-b]pyridine-3-carboxamido)acetic acid;
2-(4-hydroxy-1-(4-(methylsulfonyl)benzyl)-2-oxo-2,5,7,8-tetrahydro-1H-pyrano[4,3-b]pyridine-3-carboxamido)acetic acid;
2-(4-hydroxy-1-(4-isopropylbenzyl)-2-oxo-2,5,7,8-tetrahydro-1H-pyrano[4,3-b]pyridine-3-carboxamido)acetic acid;
2-(4-hydroxy-1-(4-isopropoxybenzyl)-2-oxo-2,5,7,8-tetrahydro-1H-pyrano[4,3-b]pyridine-3-carboxamido)acetic acid;
2-(1-(benzo[d]thiazol-2-ylmethyl)-4-hydroxy-2-oxo-2,5,7,8-tetrahydro-1H-pyrano[4,3-b]pyridine-3-carboxamido)acetic acid;
2-(1-(3,4-difluorobenzyl)-4-hydroxy-2-oxo-2,5,7,8-tetrahydro-1H-pyrano[4,3-b]pyridine-3-carboxamido)acetic acid;
2-(1-(2,4-difluorobenzyl)-4-hydroxy-2-oxo-2,5,7,8-tetrahydro-1H-pyrano[4,3-b]pyridine-3-carboxamido)acetic acid;
2-(1-(4-cyano-2-fluorobenzyl)-4-hydroxy-2-oxo-2,5,7,8-tetrahydro-1H-pyrano[4,3-b]pyridine-3-carboxamido)acetic acid;
2-(1-(4-chloro-2-fluorobenzyl)-4-hydroxy-2-oxo-2,5,7,8-tetrahydro-1H-pyrano[4,3-b]pyridine-3-carboxamido)acetic acid;
2-(1-ethyl-4-hydroxy-2-oxo-2,5,7,8-tetrahydro-1H-pyrano[4,3-b]pyridine-3-carboxamido)acetic acid;
2-(1-(cyclohexylmethyl)-4-hydroxy-2-oxo-2,5,7,8-tetrahydro-1H-pyrano[4,3-b]pyridine-3-carboxamido)acetic acid;

2-(4-hydroxy-1-(naphthalen-2-ylmethyl)-2-oxo-2,5,7,8-tetrahydro-1H-pyrano[4,3-b]pyridine-3-carboxamido)acetic acid;

2-(4-hydroxy-1-methyl-2-oxo-2,5,7,8-tetrahydro-1H-pyrano[4,3-b]pyridine-3-carboxamido)acetic acid;

2-(4-hydroxy-2-oxo-1-((5-(trifluoromethyl)pyrimidin-2-yl)methyl)-2,5,7,8-tetrahydro-1H-pyrano[4,3-b]pyridine-3-carboxamido)acetic acid;

2-(4-Hydroxy-2-oxo-1-(2,4,5-trifluorobenzyl)-2,5,7,8-tetrahydro-1H-pyrano[4,3-b]pyridine-3-carboxamido)acetic acid;

2-(4-Hydroxy-2-oxo-1-((6-(trifluoromethyl)pyridin-3-yl)methyl)-2,5,7,8-tetrahydro-1H-pyrano[4,3-b]pyridine-3-carboxamido)acetic acid;

2-(4-Hydroxy-1-(4-(methylcarbamoyl)benzyl)-2-oxo-2,5,7,8-tetrahydro-1H-pyrano[4,3-b]pyridine-3-carboxamido)acetic acid;

2-(4-Hydroxy-1-((1-methyl-1H-pyrazol-3-yl)methyl)-2-oxo-2,5,7,8-tetrahydro-1H-pyrano[4,3-b]pyridine-3-carboxamido)acetic acid;

2-(1-(4-Cyano-3-methylbenzyl)-4-hydroxy-2-oxo-2,5,7,8-tetrahydro-1H-pyrano[4,3-b]pyridine-3-carboxamido)acetic acid;

2-(1-(4-Cyano-3-fluorobenzyl)-4-hydroxy-2-oxo-2,5,7,8-tetrahydro-1H-pyrano[4,3-b]pyridine-3-carboxamido)acetic acid;

2-(4-Hydroxy-1-((6-methoxypyridin-3-yl)methyl)-2-oxo-2,5,7,8-tetrahydro-1H-pyrano[4,3-b]pyridine-3-carboxamido)acetic acid;

2-(4-Hydroxy-2-oxo-1-(thiazol-5-ylmethyl)-2,5,7,8-tetrahydro-1H-pyrano[4,3-b]pyridine-3-carboxamido)acetic acid;

2-(4-Hydroxy-2-oxo-1-((1-phenyl-1H-pyrazol-3-yl)methyl)-2,5,7,8-tetrahydro-1H-pyrano[4,3-b]pyridine-3-carboxamido)acetic acid;

2-(4-Hydroxy-1-(4-(2-hydroxypropan-2-yl)benzyl)-2-oxo-2,5,7,8-tetrahydro-1H-pyrano[4,3-b]pyridine-3-carboxamido)acetic acid;

2-(1-(4-carbamoylbenzyl)-4-hydroxy-2-oxo-2,5,7,8-tetrahydro-1H-pyrano[4,3-b]pyridine-3-carboxamido)acetic acid;

2-(4-Hydroxy-2-oxo-1-((2-(trifluoromethyl)thiazol-4-yl)methyl)-2,5,7,8-tetrahydro-1H-pyrano[4,3-b]pyridine-3-carboxamido)acetic acid;

2-(4-Hydroxy-2-oxo-1-(4-(trifluoromethoxy)phenyl)-2,5,7,8-tetrahydro-1H-pyrano[4,3-b]pyridine-3-carboxamido)acetic acid;

2-(1-(4-Chlorobenzyl)-4-hydroxy-2-oxo-2,5,6,8-tetrahydro-1H-pyrano[3,4-b]pyridine-3-carboxamido)acetic acid;

2-(1-(2,4-difluorobenzyl)-4-hydroxy-2-oxo-2,5,6,8-tetrahydro-1H-pyrano[3,4-b]pyridine-3-carboxamido)acetic acid;

2-(4-hydroxy-1-(4-isopropylbenzyl)-2-oxo-2,5,6,8-tetrahydro-1H-pyrano[3,4-b]pyridine-3-carboxamido)acetic acid;

2-(1-(4-cyanobenzyl)-4-hydroxy-2-oxo-2,5,6,8-tetrahydro-1H-pyrano[3,4-b]pyridine-3-carboxamido)acetic acid;

2-(4-hydroxy-1-(4-(methylsulfonyl)benzyl)-2-oxo-2,5,6,8-tetrahydro-1H-pyrano[3,4-b]pyridine-3-carboxamido)acetic acid;

2-(4-hydroxy-2-oxo-1-((6-(trifluoromethyl)pyridin-3-yl)methyl)-2,5,6,8-tetrahydro-1H-pyrano[3,4-b]pyridine-3-carboxamido)acetic acid;

2-(4-hydroxy-2-oxo-1-(2,4,5-trifluorobenzyl)-2,5,6,8-tetrahydro-1H-pyrano[3,4-b]pyridine-3-carboxamido)acetic acid;

2-(1-(4-cyano-2-fluorobenzyl)-4-hydroxy-2-oxo-2,5,6,8-tetrahydro-1H-pyrano[3,4-b]pyridine-3-carboxamido)acetic acid;

2-(1-(4-cyano-3-methylbenzyl)-4-hydroxy-2-oxo-2,5,6,8-tetrahydro-1H-pyrano[3,4-b]pyridine-3-carboxamido)acetic acid;

2-(4-hydroxy-2-oxo-1-((5-(trifluoromethyl)pyrimidin-2-yl)methyl)-2,5,6,8-tetrahydro-1H-pyrano[3,4-b]pyridine-3-carboxamido)acetic acid;

2-(1-(4-chloro-2-fluorobenzyl)-4-hydroxy-2-oxo-2,5,6,8-tetrahydro-1H-pyrano[3,4-b]pyridine-3-carboxamido)acetic acid;

2-(1-(benzo[d]thiazol-2-ylmethyl)-4-hydroxy-2-oxo-2,5,6,8-tetrahydro-1H-pyrano[3,4-b]pyridine-3-carboxamido)acetic acid;

2-(1-(4-(difluoromethoxy)benzyl)-4-hydroxy-2-oxo-2,5,6,8-tetrahydro-1H-pyrano[3,4-b]pyridine-3-carboxamido)acetic acid;

2-(4-hydroxy-1-((1-methyl-1H-pyrazol-3-yl)methyl)-2-oxo-2,5,6,8-tetrahydro-1H-pyrano[3,4-b]pyridine-3-carboxamido)acetic acid;

2-(4-hydroxy-1-(4-methoxybenzyl)-2-oxo-2,5,6,8-tetrahydro-1H-pyrano[3,4-b]pyridine-3-carboxamido)acetic acid;

2-(4-hydroxy-2-oxo-1-(4-(trifluoromethoxy)benzyl)-2,5,6,8-tetrahydro-1H-pyrano[3,4-b]pyridine-3-carboxamido)acetic acid;

2-(1-(4-fluorobenzyl)-4-hydroxy-2-oxo-2,5,6,8-tetrahydro-1H-pyrano[3,4-b]pyridine-3-carboxamido)acetic acid;

2-(1-(3,4-difluorobenzyl)-4-hydroxy-2-oxo-2,5,6,8-tetrahydro-1H-pyrano[3,4-b]pyridine-3-carboxamido)acetic acid;

2-(4-hydroxy-1-(4-(methylcarbamoyl)benzyl)-2-oxo-2,5,6,8-tetrahydro-1H-pyrano[3,4-b]pyridine-3-carboxamido)acetic acid;

2-(4-hydroxy-1-(4-isopropoxybenzyl)-2-oxo-2,5,6,8-tetrahydro-1H-pyrano[3,4-b]pyridine-3-carboxamido)acetic acid;

2-(1-(3-cyanobenzyl)-4-hydroxy-2-oxo-2,5,6,8-tetrahydro-1H-pyrano[3,4-b]pyridine-3-carboxamido)acetic acid;

2-(1-(2-chlorobenzyl)-4-hydroxy-2-oxo-2,5,6,8-tetrahydro-1H-pyrano[3,4-b]pyridine-3-carboxamido)acetic acid;

2-(4-hydroxy-2-oxo-1-(pyridin-2-ylmethyl)-2,5,6,8-tetrahydro-1H-pyrano[3,4-b]pyridine-3-carboxamido)acetic acid;

2-(4-hydroxy-2-oxo-1-(pyridin-4-ylmethyl)-2,5,6,8-tetrahydro-1H-pyrano[3,4-b]pyridine-3-carboxamido)acetic acid;

2-(1-(4-cyano-3-fluorobenzyl)-4-hydroxy-2-oxo-2,5,6,8-tetrahydro-1H-pyrano[3,4-b]pyridine-3-carboxamido)acetic acid;

2-(4-hydroxy-2-oxo-1-(thiazol-5-ylmethyl)-2,5,6,8-tetrahydro-1H-pyrano[3,4-b]pyridine-3-carboxamido)acetic acid;

2-(4-Hydroxy-1-(4-(2-hydroxypropan-2-yl)benzyl)-2-oxo-2,5,6,8-tetrahydro-1H-pyrano[3,4-b]pyridine-3-carboxamido)acetic acid;

2-(1-(4-Carbamoylbenzyl)-4-hydroxy-2-oxo-2,5,6,8-tetrahydro-1H-pyrano[3,4-b]pyridine-3-carboxamido)acetic acid;

2-(4-Hydroxy-2-oxo-1-((4'-(trifluoromethyl)-[1,1'-biphenyl]-4-yl)methyl)-2,5,6,8-tetrahydro-1H-pyrano[3,4-b]pyridine-3-carboxamido)acetic acid;

2-(4-hydroxy-2-oxo-1-((4'-(trifluoromethoxy)-[1,1'-biphenyl]-4-yl)methyl)-2,5,6,8-tetrahydro-1H-pyrano[3,4-b]pyridine-3-carboxamido)acetic acid;

2-(1-((4'-chloro-[1,1'-biphenyl]-4-yl)methyl)-4-hydroxy-2-oxo-2,5,6,8-tetrahydro-1H-pyrano[3,4-b]pyridine-3-carboxamido)acetic acid;

2-(1-((4'-carbamoyl-[1,1'-biphenyl]-4-yl)methyl)-4-hydroxy-2-oxo-2,5,6,8-tetrahydro-1H-pyrano[3,4-b]pyridine-3-carboxamido)acetic acid;

2-(1-((4'-cyano-[1,1'-biphenyl]-4-yl)methyl)-4-hydroxy-2-oxo-2,5,6,8-tetrahydro-1H-pyrano[3,4-b]pyridine-3-carboxamido)acetic acid;

2-(1-(4-Cyano-2-fluorobenzyl)-4-hydroxy-7-methyl-2,6-dioxo-1,2,5,6,7,8-hexahydro-1,7-naphthyridine-3-carboxamido)acetic acid;

2-(4-hydroxy-7-methyl-1-(4-(methylsulfonyl)benzyl)-2,6-dioxo-1,2,5,6,7,8-hexahydro-1,7-naphthyridine-3-carboxamido)acetic acid;

2-(1-(2,4-difluorobenzyl)-4-hydroxy-7-methyl-2,6-dioxo-1,2,5,6,7,8-hexahydro-1,7-naphthyridine-3-carboxamido)acetic acid;

2-(1-(3-cyanobenzyl)-4-hydroxy-7-methyl-2,6-dioxo-1,2,5,6,7,8-hexahydro-1,7-naphthyridine-3-carboxamido)acetic acid;

2-(1-(4-cyanobenzyl)-4-hydroxy-7-methyl-2,6-dioxo-1,2,5,6,7,8-hexahydro-1,7-naphthyridine-3-carboxamido)acetic acid;

2-(1-(4-chlorobenzyl)-4-hydroxy-7-methyl-2,6-dioxo-1,2,5,6,7,8-hexahydro-1,7-naphthyridine-3-carboxamido)acetic acid;

2-(1-(2-chlorobenzyl)-4-hydroxy-7-methyl-2,6-dioxo-1,2,5,6,7,8-hexahydro-1,7-naphthyridine-3-carboxamido)acetic acid;

2-(4-Hydroxy-2-oxo-1-(4-(trifluoromethyl)benzyl)-1,2,5,6,7,8-hexahydro-1,8-naphthyridine-3-carboxamido)acetic acid;

2-(4-Hydroxy-2-oxo-1-(4-(trifluoromethyl)benzyl)-1,2,5,6,7,8-hexahydro-1,6-naphthyridine-3-carboxamido)acetic acid;

2-(7-Benzyl-4-hydroxy-2-oxo-1-(4-(trifluoromethyl)benzyl)-1,2,5,6,7,8-hexahydro-1,7-naphthyridine-3-carboxamido)acetic acid;

2-(4-Hydroxy-6-methyl-2-oxo-1-(4-(trifluoromethyl)benzyl)-1,2,5,6,7,8-hexahydro-1,6-naphthyridine-3-carboxamido)acetic acid;

2-((5S,8R)-1-(benzo[d]thiazol-2-ylmethyl)-4-hydroxy-2-oxo-1,2,5,6,7,8-hexahydro-5,8-methanoquinoline-3-carboxamido)acetic acid;

2-(-4-hydroxy-2-oxo-1-(4-(trifluoromethyl)benzyl)-1,2,5,6,7,8-hexahydro-5,8-methanoquinoline-3-carboxamido)acetic acid;

2-(-4-hydroxy-2-oxo-1-((2-phenylthiazol-5-yl)methyl)-1,2,5,6,7,8-hexahydro-5,8-methanoquinoline-3-carboxamido)acetic acid; or 2-(-4-hydroxy-2-oxo-1-((4-phenylthiazol-2-yl)methyl)-1,2,5,6,7,8-hexahydro-5,8-methanoquinoline-3-carboxamido)acetic acid;

or a pharmaceutically acceptable salt thereof.

3. A pharmaceutical composition comprising a compound of formula II as recited in claim 1 and a pharmaceutically acceptable carrier.

4. A compound of formula II or a pharmaceutically acceptable salt thereof:

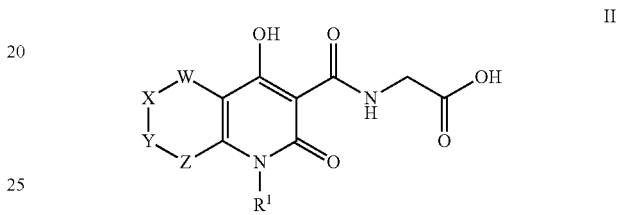

wherein:

W is $CH_2$ or $NR^5$;

X is $CH_2$, O, (C=O), or $NR^5$;

Y is O or $NR^5$;

Z is $CH_2$ or $NR^5$; wherein when W is $CH_2$ and Z is $CH_2$ then W and Z optionally combine with another carbon atom to form a bridge;

$R^1$ is selected from hydrogen, $C_{1-4}$ alkyl, $C_{3-8}$ cycloalkyl, aryl, heterocyclyl, Me-aryl, Me-heterocyclyl, Me-cycloalkyl, said cycloalkyl, aryl and heterocyclyl are optionally substituted with 1, 2, or 3 substituents chosen from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN;

$R^5$ is independently hydrogen, methyl or phenyl; and $R^b$ is independently hydrogen or $C_{1-4}$ alkyl.

5. A pharmaceutical composition comprising a compound of formula II as recited in claim 4 and a pharmaceutically acceptable carrier.

* * * * *